United States Patent
Keasling et al.

(10) Patent No.: US 10,844,406 B2
(45) Date of Patent: *Nov. 24, 2020

(54) PRODUCTION OF FATTY ACIDS AND DERIVATIVES THEREOF

(71) Applicant: Genomatica, Inc., San Diego, CA (US)

(72) Inventors: Jay D. Keasling, Berkeley, CA (US); Zhihao Hu, South San Francisco, CA (US); Chris Somerville, Tiburon, CA (US); George Church, Brookline, MA (US); David Berry, Cambridge, MA (US); Lisa C. Friedman, South San Francisco, CA (US); Andreas Schirmer, South San Francisco, CA (US); Shane Brubaker, El Cerrito, CA (US); Stephen B. Del Cardayre, South San Francisco, CA (US)

(73) Assignee: Genomatica, Inc., San Diego, CA (US)

(*) Notice: Subject to any disclaimer, the term of this patent is extended or adjusted under 35 U.S.C. 154(b) by 533 days.

This patent is subject to a terminal disclaimer.

(21) Appl. No.: 15/451,881

(22) Filed: Mar. 7, 2017

(65) Prior Publication Data
US 2017/0275651 A1   Sep. 28, 2017

Related U.S. Application Data

(63) Continuation of application No. 13/870,426, filed on Apr. 25, 2013, now Pat. No. 9,598,706, which is a continuation of application No. 13/302,957, filed on Nov. 22, 2011, now abandoned, which is a continuation of application No. 12/278,957, filed as application No. PCT/US2007/011923 on May 18, 2007, now abandoned.

(60) Provisional application No. 60/801,995, filed on May 19, 2006, provisional application No. 60/802,016, filed on May 19, 2006, provisional application No. 60/908,547, filed on Mar. 28, 2007.

(51) Int. Cl.
| | |
|---|---|
| *C12P 7/04* | (2006.01) |
| *C10L 1/02* | (2006.01) |
| *C10L 1/32* | (2006.01) |
| *C12P 7/64* | (2006.01) |
| *C07C 31/125* | (2006.01) |
| *C07C 33/02* | (2006.01) |

(52) U.S. Cl.
CPC .............. *C12P 7/04* (2013.01); *C07C 31/125* (2013.01); *C07C 33/02* (2013.01); *C10L 1/026* (2013.01); *C10L 1/328* (2013.01); *C12P 7/649* (2013.01); *C12P 7/6436* (2013.01); *C12P 7/6463* (2013.01); *Y02E 50/13* (2013.01)

(58) Field of Classification Search
CPC ............ C07C 31/125; C12P 7/04; C12N 1/15; C12N 1/21
See application file for complete search history.

(56) References Cited

U.S. PATENT DOCUMENTS

| | | |
|---|---|---|
| 5,000,000 A | 3/1991 | Ingram et al. |
| 5,028,539 A | 7/1991 | Ingram et al. |
| 5,233,109 A | 8/1993 | Chow |
| 5,424,202 A | 6/1995 | Ingram et al. |
| 5,441,742 A | 8/1995 | Autant et al. |
| 5,445,947 A | 8/1995 | Metz et al. |
| 5,482,846 A | 1/1996 | Ingram et al. |
| 5,530,186 A | 6/1996 | Hitz et al. |
| 5,536,659 A | 7/1996 | Fukuda et al. |
| 5,602,030 A | 2/1997 | Ingrahm et al. |
| 5,807,893 A | 9/1998 | Voelker et al. |
| 5,908,617 A | 6/1999 | Moore et al. |
| 5,939,250 A | 8/1999 | Short |
| 5,955,329 A | 9/1999 | Yuan et al. |
| 6,015,440 A | 1/2000 | Noureddini |
| 6,143,538 A | 11/2000 | Somerville et al. |
| 6,229,056 B1 | 5/2001 | Ansmann et al. |
| 6,491,927 B1 | 12/2002 | Arnaud et al. |
| 6,583,266 B1 | 6/2003 | Smith et al. |
| 6,596,538 B1 | 7/2003 | Lardizabal et al. |
| 6,750,048 B2 | 6/2004 | Ruecker et al. |
| 6,960,455 B2 | 11/2005 | Livshits et al. |
| 6,982,155 B1 | 1/2006 | Fukuda et al. |
| 7,056,714 B2 | 6/2006 | Rosazza et al. |
| 7,118,896 B2 | 10/2006 | Kalscheuer et al. |
| 7,169,588 B2 | 1/2007 | Burch et al. |
| 7,314,974 B2 | 1/2008 | Cao et al. |
| 7,425,433 B2 | 9/2008 | Rosazza et al. |
| 7,491,854 B2 | 2/2009 | Binder |
| 7,608,700 B2 | 10/2009 | Klaenhammer et al. |
| 7,691,159 B2 | 4/2010 | Li |
| 8,110,093 B2 | 2/2012 | Friedman et al. |
| 8,110,670 B2 | 2/2012 | Hu et al. |

(Continued)

FOREIGN PATENT DOCUMENTS

| | | |
|---|---|---|
| BR | PI0712205 A2 | 2/2012 |
| CN | 1491282 A | 4/2004 |

(Continued)

OTHER PUBLICATIONS

Rejection decision issued on Brazilian Application 1220170101145, dated Mar. 9, 2018.

Abbadi et al., "Knockout of the regulatory site of 3-ketoacyl-ACP synthase III enhances short-and medium-chain acyl-ACP synthesis", Plant Journal, 24(1): 1-9 (2000).

Abdel-Hamid et al., "Coordinate Expression of the Acetyl Coenzyme A Carboxylase Genes, accB and accC, is Necessary for Normal Regulation of Biotin Synthesis in *Escherichia coli*", J. Bacteriol., 189:369-376 (2007).

(Continued)

*Primary Examiner* — Maryam Monshipouri
(74) *Attorney, Agent, or Firm* — Harness, Dickey & Pierce, P.L.C.

(57) ABSTRACT

Compositions and methods for production of fatty alcohols using recombinant microorganisms are provided as well as fatty alcohol compositions produced by such methods.

5 Claims, 31 Drawing Sheets

Specification includes a Sequence Listing.

(56) References Cited

U.S. PATENT DOCUMENTS

| | | |
|---|---|---|
| 8,268,599 B2 | 9/2012 | Schirmer et al. |
| 8,283,143 B2 | 10/2012 | Hu et al. |
| 8,313,934 B2 | 11/2012 | Bhatia et al. |
| 8,323,924 B2 | 12/2012 | Schirmer et al. |
| 8,535,916 B2 | 9/2013 | Del Cardayre et al. |
| 9,017,984 B2 | 4/2015 | Hu et al. |
| 9,133,406 B2 | 9/2015 | Gaertner |
| 9,587,231 B2 | 3/2017 | Hom et al. |
| 10,017,455 B2 | 7/2018 | Hu et al. |
| 2003/0040474 A1 | 2/2003 | Kapeller-Libermann et al. |
| 2003/0064328 A1 | 4/2003 | Friedel |
| 2003/0097686 A1 | 5/2003 | Knauf et al. |
| 2003/0129601 A1 | 7/2003 | Cole |
| 2003/0233675 A1 | 12/2003 | Cao et al. |
| 2004/0005678 A1 | 1/2004 | Keasling et al. |
| 2004/0009576 A1 | 1/2004 | Kalscheuer et al. |
| 2004/0072323 A1 | 4/2004 | Matsuda et al. |
| 2004/0161833 A1 | 8/2004 | Shah |
| 2004/0180400 A1 | 9/2004 | Rosazza et al. |
| 2004/0197896 A1 | 10/2004 | Cole |
| 2005/0019863 A1 | 1/2005 | Sarmientos et al. |
| 2005/0130126 A1 | 6/2005 | Durmaz et al. |
| 2005/0250135 A1 | 11/2005 | Klaenhammer et al. |
| 2006/0014977 A1 | 1/2006 | Miller et al. |
| 2006/0037237 A1 | 2/2006 | Copeland et al. |
| 2006/0195947 A1 | 8/2006 | Davis et al. |
| 2006/0206963 A1 | 9/2006 | Voelker et al. |
| 2007/0003736 A1 | 1/2007 | Saarvali et al. |
| 2007/0192900 A1 | 8/2007 | Sticklen |
| 2007/0251141 A1 | 11/2007 | Bist et al. |
| 2007/0261138 A1 | 11/2007 | Graham et al. |
| 2007/0270319 A1 | 11/2007 | Seggelkow et al. |
| 2007/0281345 A1 | 12/2007 | Binder |
| 2008/0161595 A1 | 7/2008 | Huang et al. |
| 2008/0221310 A1 | 9/2008 | O'Sullivan et al. |
| 2008/0295388 A1 | 12/2008 | Bazzani et al. |
| 2009/0038211 A1 | 2/2009 | Sarin et al. |
| 2009/0047721 A1 | 2/2009 | Trimbur et al. |
| 2009/0075333 A1 | 3/2009 | Campbell et al. |
| 2009/0084025 A1 | 4/2009 | Bhatia et al. |
| 2009/0117629 A1 | 5/2009 | Schmidt-Dannert et al. |
| 2009/0136469 A1 | 5/2009 | Senin et al. |
| 2009/0215140 A1 | 8/2009 | Kurano et al. |
| 2009/0275097 A1 | 11/2009 | Sun et al. |
| 2010/0071259 A1 | 3/2010 | Hu et al. |
| 2010/0105955 A1 | 4/2010 | Alibhai et al. |
| 2010/0105963 A1 | 4/2010 | Hu |
| 2010/0185017 A1 | 7/2010 | Yoshikuni et al. |
| 2010/0221798 A1 | 9/2010 | Schirmer et al. |
| 2010/0242345 A1 | 9/2010 | Keasling et al. |
| 2010/0249470 A1 | 9/2010 | Schirmer et al. |
| 2010/0251601 A1 | 10/2010 | Hu et al. |
| 2010/0257777 A1 | 10/2010 | Sanchez-Riera et al. |
| 2010/0257778 A1 | 10/2010 | Gaertner et al. |
| 2010/0274033 A1 | 10/2010 | Sanchez-Riera et al. |
| 2011/0072714 A1 | 3/2011 | Gaertner |
| 2011/0097769 A1 | 4/2011 | Del Cardayre et al. |
| 2011/0146142 A1 | 6/2011 | Lee et al. |
| 2011/0162259 A1 | 7/2011 | Gaertner |
| 2012/0040426 A1 | 2/2012 | Sun et al. |
| 2013/0084608 A1 | 4/2013 | Szabo et al. |

FOREIGN PATENT DOCUMENTS

| | | |
|---|---|---|
| DE | 10 2004 052 115 | 4/2006 |
| EP | 1 241 262 A2 | 9/2002 |
| EP | 0 557 469 | 3/2004 |
| EP | 2 024 491 | 11/2014 |
| GB | 2 090 611 | 7/1982 |
| JP | 08-173165 | 7/1996 |
| JP | 2002-223788 A | 8/2002 |
| JP | 2009-511091 A | 3/2009 |
| JP | 2010-505388 A | 2/2010 |
| KR | 10200717428 | 2/2007 |
| WO | WO-99/18118 A1 | 4/1999 |
| WO | WO-00/12725 A2 | 3/2000 |
| WO | WO-00/61740 | 10/2000 |
| WO | WO-00/78782 A1 | 12/2000 |
| WO | WO-02/40690 | 5/2002 |
| WO | WO-03/074676 | 9/2003 |
| WO | WO-2004/000871 | 12/2003 |
| WO | WO-2004/031376 A2 | 4/2004 |
| WO | WO-2004/081226 | 9/2004 |
| WO | WO-2005/007845 | 1/2005 |
| WO | WO-2005/052163 A2 | 6/2005 |
| WO | WO 2005/077495 A1 | 8/2005 |
| WO | WO-2006/014837 A1 | 2/2006 |
| WO | WO-2006/037947 A1 | 4/2006 |
| WO | WO-2007/022169 | 2/2007 |
| WO | WO-2007/032538 A1 | 3/2007 |
| WO | WO-2007/136762 A2 | 11/2007 |
| WO | WO-2008/058788 | 5/2008 |
| WO | WO-2008/100251 | 8/2008 |
| WO | WO-2008/119082 A2 | 10/2008 |
| WO | WO-2009/042950 A1 | 4/2009 |
| WO | WO-2009/140695 A2 | 11/2009 |
| WO | WO-2009/140696 | 11/2009 |
| WO | WO-2010/021711 | 2/2010 |
| WO | WO-2010/022090 A1 | 2/2010 |
| WO | WO-2010/033921 | 3/2010 |
| WO | WO-2010/042664 A1 | 4/2010 |
| WO | WO-2010/062480 A2 | 6/2010 |
| WO | WO-2010/118409 A1 | 10/2010 |
| WO | WO-2010/118410 A1 | 10/2010 |
| WO | WO-2010/126891 A1 | 11/2010 |
| WO | WO-2010/127318 | 11/2010 |
| WO | WO-2011/038132 A1 | 3/2011 |
| WO | WO-2011/038134 A1 | 3/2011 |
| WO | WO-2011/062987 | 5/2011 |

OTHER PUBLICATIONS

Abdel-Hamid et al., "Pyruvate oxidase contributes to the aerobic growth efficiency of *Escherichia coli*," Microbiol. 147(6):1483-98 (2001).

Alper, et al., "Engineering for biofuels: exploiting innate microbial capacity or importing biosynthetic potential?", NRM 7: 715-723 (2009).

Alvarez, et al., "Triacylglycerols in prokaryotic microorganisms", Appl.Microbiol.Biotechnol., 60: 367-376 (2002).

Antoni, et al., "Biofuels from microbes," Appl. Microbial. Biotechnol., 77: 23-35 (2007).

Atsumi et al., "Metabolic engineering for advanced biofuels production from *Escherichia coli*", Current Opin.Biotech, 19:414-419 (2008).

Atsumi et al., "Metabolic engineering of *Escherichia coli* for 1-butanol production", Metabolic Engineering 10:305-311 (2008).

Atsumi et al., "Non-fermentative pathways for synthesis of branched-chain higher alcohols as biofuels", Nature, 451: 86-89 (2008).

Barnes, Jr. et al., "Studies on the Mechanism of Fatty Acid Synthesis. XIX. Preparation and General Properties of Palmityl Thioesterase", J. Biol. Chem., 243(11):2955-2962 (1968).

Beekwilder et al., "Functional Characterization of Enzymes Forming Volatile Esters from Strawberry and Banana", Plant Physiology, 135: 1865-1878 (2004).

Beinert, H., "Recent developments in the field of iron-sulfur proteins", FASEB J. 4: 2483-2491 (1990).

Benoist et al., "In vivo sequence requirements of the SV40 early promoter region," Nature 290(5804): 304-310 (1981).

Bergler et al., "Protein EnvM is the NADH-dependent Enoyl-ACP Reductase (FabI) of *Escherichia coli*," J. Biol. Chem., 269(8): 5943-5946 (1994).

Bergler et al., "The enoyl-[acyl-carrier-protein] reductase (FabI) of *Escherichia coli*, which catalyzes a key regulatory step in fatty acid biosynthesis, accepts NADH and NADPH as cofactors and is inhibited by palmitoyl-CoA", Eur. J. Biochem. 242: 689-694 (1996).

Berrios-Rivera et al., "The Effect of Increasing NADH Availability on the Redistribution of Metabolic Fluxes in *Escherichia coli* Chemostat Cultures", Metabolic Engineering 4: 230-237 (2002).

Birge et al., "Acyl Carrier Protein. XVI.Intermediate Reactions of Unsaturated Fatty Acid Synthesis in *Escerichia coli* and Studies of fab B Mutants", J.Biol.Chem. 247(16): 4921-4929 (1972).

(56) References Cited

OTHER PUBLICATIONS

Bitter et al., "Expression and Secretion Vectors for Yeast," Methods in Enzymology—Recombinant DNA, vol. 153, Part D, (1987), pp. 516-545.
Black et al., "Cloning, Sequencing and Expression of the fadD Gene of *Escherichia coli* Encoding Acyl Coenzyme A Synthetase," J. Biol. Chem. vol. 267, No. 35, Dec. 15, 1992, pp. 25513-25520.
Black et al., "Cloning, Sequencing, and Expression of the fadD Gene of *Escherichia coli* Encoding Acyl Coenzyme A Synthetase," J. Biol. Chem. 267(35): 25513-25520 (1992).
Black et al., "Long-Chain Acyl-CoA—Dependent Regulation of Gene Expression in Bacteria, Yeast and Mammals", J. Nutrition, 305S-309S (2000).
Black et al., "Mutational Analysis of a Fatty Acyl-Coenzyme A Synthetase Signature Motif Identifies Seven Amino Acid Residues That Modulate Fatty Acid Substrate Specificity", J. Biol. Chem. 272(8) 4896-4903 (1997).
Black, P., "Primary Sequence of the *Escherichia coli* fadL Gene Encoding an Outer Membrane Protein Required for Long-Chain Fatty Acid Transport", J. Bacteriololgy 173(2): 435-442 (1991).
Blanchard et al., "Overexpression and Kinetic Characterization of the Carboxyltransferase Component of Acetyl-CoA Carboxylase", J.Biol.Chem. 273(30): 19140-19145 (1998).
Bonamore et al., "The desaturase from Bacillus subtilis, a promising tool for the selective olefination of phospholipids", J.Biotechnology 121: 49-53 (2006).
Bond-Watts et al., "Enzyme mechanism as a kinetic control element for designing synthetic biofuel pathways", Nature Chem Bio 537: 1-6 (Suppl. S1-S28) (2011).
Bonner et al., "Purification and Properties of Fatty Acyl Thioesterase I from *Escherichia coli*", J.Biol.Chem. 247(10): 3123-3133 (1972).
Boonstra et al., "The udhA Gene of *Escherichia coli* Encodes a Soluble Pyridine Nucleotide Transhydrogenase", J. Bacteriol. 181(3): 1030-1034 (1999).
Boulanger et al., "Purification and Structrual and Functional Characterization of FhuA, a Transporter of the *Escherichia coli* Outer Membrane," Biochemistry, 35(45): 14216-14224 (1996).
Bredwell et al., "Reactor Design Issues for Synthesis-Gas Fermentations", Biotechnol. Prog. 15: 834-844 (1999).
Bunch et al., "The ldhA gene encoding the fermentative lactate dehydrogenase of *Escherichia coli*," Microbiol. 143(1):187-95 (1997).
Cahoon et al., "A Determinant of Substrate Specificity Predicted from the Acyl-Acyl Carrier Protein Desaturase of Developing Cat's Claw Seed," Plant Physiol 117: 593-598 (1998).
Cahoon et al., "Modification of the Fatty Acid Composition of *Escherichia coli* by Coexpression of a Plant Acyl-Acyl Carrier Protein Desaturase and Ferredoxin", J.Bacteriol. 178(3): 936-936 (1996).
Cahoon et al., "Redesign of soluble fatty acid desaturases from plants for altered substrate specificity and double bond position", Proc. Natl. Acad. Sci.94: 4872-4877 (1997).
Camilli, "Bacterial Small-Molecule Signaling Pathways," Science 311(5764): 1113-1116 (2006).
Campbell et al., "*Escherichia coli* FadR Positively Regulates Transcription of the fabB Fatty Acid Biosynthetic Gene", J.Bacteriol. 183(20): 5982-5990 (2001).
Campbell et al., "The Enigmatic *Escherichia coli* neu Gene is yafH" J. Bacteriol., 184(13): 3759-3764 (2002).
Cann et al., "Production of 2-methyl-1-butanol in engineered *Escherichia coli*", Appl Microbiol Biotechnol. 81: 89-98 (2008).
Canoira et al, "Biodiesel from Jojoba oil-wax: Transesterification with methanol and properties as a fuel", Biomass and Bioenergy 30:76-81 ((2006).
Canonaco et al., "Metabolic flux response to phosphoglucose isomerase knock-out in *Escherichia coli* and impact of overexpression of the soluble transhydrogenase UdhA," FEMS Microbiology Letters 204: 247-252 (2001).
Causey et al., "Engineering *Escherichia coli* for efficient conversion of glucose to pyruvate," PNAS, vol. 101, No. 8, Feb. 24, 2004, 2235-2240.

Caviglia et al., Rat Long Chain Acyl-CoA Synthetase 5, but Not 1, 2, 3, or 4, Complements *Escherichia coli* fadD*, The Journal of Biological Chemistry, 279(12): 1163-1169 (2004).
Chang et al., "Genetic and Biochemical Analyses of *Escherichia coli* Strains Having a Mutation in the Structural Gene (poxB) for Pyruvate Oxidase," J. Bacteriol. 154(2): 756-62 (1983).
Chassagnole et al., "Dynamic Modeling of the Central Carbon Metabolism of *Escherichia coli*", Biotech & Engineering 79(1): 59-73 (2002).
Chen et al., "Biosynthesis of Ansatrienin (mycotrienin) and naphthomycin, Identification and Analysis of Two Separate Biosynthetic Gene Clusters in Streptomyces Collinus Tu 1892," Eur. J. Biochem. 261: 98-107 (1999).
Chen, "Permeability issues in whole-cell bioprocesses and cellular membrane engineering", Appl Microbiol Biotechnol 74: 730-738 (2007).
Cheng et al., "Mammalian Wax Biosynthesis, II. Expression Cloning of a Wax Synthase cDNAs Encoding a Member of the Acyltransferase Enzyme Family*," J. Biol. Chem., 279(36): 37798-37807 (2004).
Cheng, J. et al., "Mammalian Wax Biosynthesis," J. Biol. Chem. 279(36):37798-37807, 2004.
Cho et al. "Defective Export of a Periplasmic Enzyme Disrupts Regulation of Fatty Acid Synthesis," J. Biol. Chem. vol. 270, No. 9, Mar. 3, 1995, pp. 4216-4219.
Cho et al., "Transcriptional regulation of the fad regulon genes of *Escherichia coli* by ArcA", Microbiology 152: 2207-2219 (2006).
Choi et al., ".beta.-Ketoacyl-acyl Carrier Protein Synthase III (FabH) is a Determining Factor in Branched-Chain Fatty Acid Biosynthesis" J. of Bacteriology 182(2): 365-370 (2000).
Coleman et al., "Enzymes of triacylglycerol synthesis and their regulation" Progress in Lipid Research 43:134-176 (2004).
Collister et al., "Modification of the petroleum system concept: Origins of alkanes and isoprenoids in crude oils" AAPG Bulletin 88(5):587-611 (2004).
Communication issued on EP Application 12194886.3 dated Jun. 8, 2016.
Communication issued on EP Application 14193614.6, dated Mar. 8, 2017.
Communication issued on EP Application 15179791.7, dated Dec. 16, 2016.
Conway et al., "Cloning and Sequencing of the Alcohol Dehydrogenase II Gene from Zymomonas mobilis" J. Bacteriol. 169(6): 2591-2597 (1987).
Costaglioli, p. et al., "Profiling candidate genes involved in wax biosynthesis in *Arabidopsis thaliana* by mircroarray analysis," Biochimica et Biophysica Acta. 2005, vol. 1734, pp. 247-258.
Cropp et al., "Identification of a Cyclohexylcarbonyl CoA Biosynthetic Gene Cluster and Application in the Production of Doramectin," Nature Biotech. 180: 980 (2000).
Database EMBL (Online), Jul. 1996, "Synechococcus, PCC7942 Ribosomal Protein 51 of 30S Ribosome (rpsl), ORF271, ORF231, ORF341, Carboxyltransferase alpha subunit (accA), ORF245, ORF227, and GTP cyclohydrolase I (folE) genes, complete cds, and ORF205 gene, partial cds.," XP002564232, 4 pages.
Database UniProt (Online), Nov. 1996, "SubName: Full=Putative uncharacterized Cl2 protein; SubName: Full=Putative uncharacterized protein SEC0028;" XP002564231, retrieved from EBI accession No. Uniprot: 054765, Database accession No. 054765, 1 page.
Database UniProt, Online, Nov. 1996, XP002545841, Retrieved from EBI Accession No. Uniprot:Q54764, 1 page.
Database UniProt, Online, Nov. 1996, XP002564231, Retrieved from EBI Accession No. Uniprot:Q54765, 1 page.
Database Uniprot, Online, Nov. 1996, XP002564232, Retrieved from EBI Accession No. Uniprot:Q54765, 4 pages.
Datsenko et al., "One-step Inactivation of Chromosomal Genes in *Escherichia coli* K-12 using PCR Products," Proc. Natl. Acad. Sci USA 97: 6640-6645 (2000).
Davis et al., "Inhibition of *Escherichia coli* Acetyl Coenzyme A Carboxylase by Acyl-Acyl Carrier Protein," (2001) Journal of Bacteriology 183(4):1499-1503.

(56) References Cited

OTHER PUBLICATIONS

Davis et al., "Overproduction of Acetyl-CoA Carboxylase Activity Increases the Rate of Fatty Acid Biosynthesis in *Escherichia coli*" J.Biol.Chem 275(37:15) 28593-28598 (2000).

Davis, J.B., "Microbial Incorporation of Fatty Acids Derived From n-Alkanes Into Glycerides and Waxes" Applied Microbiology 12(3): 210-214 (1964).

De Mendoza et al., "Thermal Regulation of Membrane Fluidity in *Escherichia coli*. Effects of Overproduction of P-Ketoacylacyl Carrier Protein Synthase 1," J. Biol. Chem. 258(4):2098-2101 (1983).

Dehesh et al., "KAS IV: A 3-ketoacyl-ACP synthase from *Cuphea* sp. is a medium chain specific condensing enzyme", The Plant Journal 15(3):383-390 (1998).

Dellomonaco et al., "Engineered Respiro-Fermentative Metabolism for the Production of Biofuels and Biochemicals from Fatty Acid-Rich Feedstocks", Applied & Environmental Microbiology 76(15): 5067-5078 (2010).

Denoya et al., "A Second Branded-Chain .alpha.-Keto Acid Dehydrogenase Gene Cluster (bkdFGH) from Streptomyces avermitilis: Its Relationship to Avermectin Biosynthesis and the Construction of a bkdF Mutant Suitable for the Production of Novel Antiparasitic Avermectins," J. Bacteriol. 177(12): 3504-3511 (1995).

Dermibras, A., "Relationships derived from physical properties of vegetable oil and biodiesel fuels", Fuel 87: 1743-1748 (2008).

Deveaux et al., "Genetic and Biochemical Characterization of a Mutation (fatA) That Allows trans Unsaturated Fatty Acids to Replace the Essential cis Unsaturated Fatty Acids of *Escherichia coli*" J.Bacteriol. 171(3):1562-1568 (1989).

Doan et al., "Functional expression of five *Arabidopsis* fatty acyl-CoA reductase genes in *Escherichia coli*" J. Plant Physiology 166:787-796 (2009).

Domka et al., "YliH (BssR) and YceP (BssS) Regulate *Escherichia coli* K-12 Biofilm Bormation by Influencing Cell Signaling" Appl. and Environ. Microbiol. 72(4):2449-2459 (2006).

Dormann et al., "Specificities of the Acyl-Acyl Carrier Protein (ACP) Thioesterase and Glycerol-3-Phosphate Acyltransferase for Octadecenoyl-ACP Isomers (Identification of a Petroselinoyl-ACP Thioesterase in Umbelliferae)," Plant Physiol.104: 839-844 (1994).

Duan et al., "De novo Biosynthesis of Biodiesel by *Escherichia coli* in Optimized Fed-Batch Cultivation", PLoS ONE 6(5): 1-7 (2011).

Durre, P., "Fermentative Butanol Production: Bulk Chemical and Biofuel" Ann. N. Y. Acad. Sci. 1125: 353-362 (2008).

Dworkin et al., "The PspA Protein of *Escherichia coli* is a Negative Regulator of sigma54-Dependent Transcription," J. Bacteriol. 182(2): 311-319 (2000).

Edwards et al., "The *Escherichia coli* MG1655 in silico metabolic genotype: Its definition, characteristics, and capabilities", PNAS 97(10): 5528-5533 (2000).

Elbahloul et al., "Pilot-Scale Production of Fatty Acid Ethyl Esters by an Engineered *Escherichia coli* Strain Harboring the p(Microdiesel) Plasmid", Appl. and Environ. Microbiol. 76(13):4560-4565 (2010).

Examination Report issued on Australian Application 2017203360, dated Jun. 14, 2018.

Examination Report issued on Australian Application2 015238773, dated Nov. 10, 2016.

Farewell et al., "Role of the *Escherichia coli* FadR Regulator in Stasis Survival and Growth Phase-Dependent Expression of the uspA, fad, and fab Genes", J. Bacteriol. 178(22): 6443-6450 (1996).

Fehler et al., "Biosynthesis of Hydrocarbons in Anabaena variabilis incorporation of Methyl Carbon-14 and Methyl Deuterium Metionine into 7 and 8 Methylhepta Decanes," Biochemistry, vol. 9, No. 2, Jan. 20, 1970, pp. 418-422.

Fehler, et al., Biosynthesis of Hydrocarbons in Anabaena variabilis. Incorporation of [methyl-14C]- and [methy/-2H2] Methionine into 7- and 8-Methylheptadecanes*, Biochemistry, vol. 9, No. 2, Jan. 1970, pp. 418-422.

Feng et al., "*Escherichia coli* Unsaturated Fatty Acid Synthesis: Complex Transcription of the fabA Gene and in Vivo Identification of the Essential Reaction Catalyzed by FabB", J.Biol.Chem. 284(43): 29526-29535 (2009).

Feng et al., "Overlapping Repressor Binding Sites Result in Additive Regulation of *Escherichia coli* FadH by FadR and ArcA" J. of Bacteriology 192(17):4289-4299 (2010).

Final Office Action on U.S. Appl. No. 12/278,957 dated May 1, 2017.

Final Office Action on U.S. Appl. No. 12/768,419 dated Jul. 14, 2016.

Final Office Action on U.S. Appl. No. 13/870,426 dated Jun. 29, 2016.

Fischer et al., "Selection and optimization of microbial hosts for biofuels production" Metabolic Engineering 10:295-304 (2008).

Flaman et al., "Site-directed Mutagenesis of Acyl Carrier Protein (ACP) Reveals Amino Acid Residues Involved in ACP Structure and Acyl-ACP Synthetase Activity," J.Biol.Chem. 276(38): 35934-35939 (2001).

Foecking et al., "Powerful and versatile enhancer-promoter unit for mammalian expression vectors," Gene 45: 101-105 (1986).

Fozo et al., "The fabM Gene Product of *Streptococcus* mutans is Responsible for the Synthesis of Monounsaturated Fatty Acids and is Necessary for Survival at Low pH", J. Bacteriol. 186(13): 4152-4158 (2004).

Fu et al. Oleylethanolamide regulates feeding and body weight through activation of the nuclear receptor PPAR-beta), (2003) Nature 425(6953): 90-93.

Fujita et al., "Regulation of fatty acid metabolism in bacteria", Mol. Microbiology 66(4): 829-839 (2007).

Ghisla et al., "Acyl-CoA dehydrogenases—A mechanistic overview," Eur. J. Biochem. 271: 494-508 (2004).

Glick, "Factors affecting the expression of foreign proteins in *Escherichia coli*," J Ind. Microbiol. and Biotech. 1(5): 277 (1987).

Hamer et al., "Regulation in vivo of a cloned mammalian gene: cadmium induces the transcription of a mouse metallothionein gene is SV40 vectors," J. Mol. Appl. Gen. 1:273, 1982.

Hamilton-Kemp et al., "Production of the Long-Chain Alcohols Octanol, Decanol, and Dodecanol by *Escherichia coli*", Current Microbiology 51: 82-86 (2005).

Han and Reynolds, "A novel alternate anaplerotic pathway to the glyoxylate cycle in sreptomycetes," J. Bacteriol. 179(16): 5157 (1997).

Han et al., "A Novel Alternate Anaplerotic Pathway to the Glyoxylate Cycle in Streptomycetes," J. Bacteriol. 179(16): 5157-5164 (1997).

Han, et al., "Biosynthesis of Alkanes in Nostoc Muscorum," Journal of the American Chemical Society, 91:18, Aug. 1969, pp. 5156-5159.

Hantke, K., "Ferrous iron transport mutants in *Escherichia coli* K12," FEMS Microbiology Letters 44: 53-57 (1987).

He et al., "*Nocardia* sp. Carboxylic Acid Reductase: Cloning, Expression, and Characterization of a New Aldehyde Oxidoreductase Family," Applied and Environmental Microbiology 70(3): 1874-1881 (2004).

Heath et al., "Lipid Biosynthesis as a Target for Antibacterial Agents," Progress in Lipid Research 40, 2001, pp. 467-497, 31 pages.

Heath et al., "Regulation of Fatty Acid Elongation and Initiation by Acyl-Acyl Carrier Protein in *Escherichia coli*", J.Biol.Chem. vol. 271(4): 1833-1836 (1996).

Heath et al., "Regulation of Malonyl-CoA Metabolism by Acyl-Acyl Carrier Protein and .beta.-Ketoacyl-Acyl Carrier Protein Synthases in *Escherichia coli*", J.Biol.Chem. 270 (26):15531-15538 (1995).

Henry et al., "*Escherichia coli* Transcription Factor That Both Activates Fatty Acid Synthesis and Represses Fatty Acid Degradation", J. Mol. Biol. 222: 843-849 (1991).

Hoffmeister, et al., "Mitochondrial trans-2-Enoyl-CoA Reductase of Wax Ester Fermentation from Euglena gracilis Defines a New Family of Enzymes Involved in Lipid Synthesis*," The Journal of Biological Chemistry, vol. 280, No. 6, Issue of Feb. 2005, pp. 4329-4338, 10 pages.

Hsieh. "Pool Size and Mean Age of Stable Soil Organic Carbon in Cropland," Soil Sci. Soc. Am. J., 56:460 (1992).

(56) References Cited

OTHER PUBLICATIONS

Huisman et al., "Towards novel processes for the fine-chemical and pharmaceutical industries," Curr. Opin. Biotechnol. 13: 352-358 (2002).
Hunt et al., "Characterization of an Acyl-CoA Thioesterase That Functions as a Major Regulator of Peroxisomal Lipid Metabolism" J.Biol.Chem. 277(2):1128-1138 (2002).
Imahara et al., "Thermodynamic study on cloud point of biodiesel with its fatty acid composition", Fuel 85: 1666-1670 (2006).
Inui, et al., "Fatty Acid Synthesis in Mitochondria of Euglena gracilis," Eur. J. Biochem. 142, 1984, pp. 121-126, 6 pages.
Ishige et al., "Long-Chain Aldehyde Dehydrogenase That Participates in n-Alkane Utilization and Wax Ester Synthesis in *Acinetobacter* sp. Strain M-1", Appl. Environ. Microbiol. 66(8): 3481-3486 (2000).
Ishige et al., "Wax Ester Production from n-Alkanes by *Acinetobacter* sp. Strain M-1: Ultrastructure of Cellular Inclusions and Role of Acyl Coenzyme A Reductase", Appl. Environ. Microbiol. 68(3): 1192-1195 (2002).
James et al., "Expression of Two *Escherichia coli* Acetyl-CoA Caroxylase Subunits is Autoregulated," The Journal of Biological Chemistry, vol. 279, No. 4, Jan. 23, 2004, pp. 2520-2527.
Jarboe, L.R. et al., "Development of Ethanologenic Bacteria," Adv. Biochem. Enqin./Biotechnol. 108:237-261 (2007).
Jayakumar et al., "Cloning and expression of the multifunctional human fatty acid synthase and its subdomains in *Escherichia coli*",PNAS 93: 14509-14514 (1996).
Jiang et al., "Inhibition of Fatty Acid Synthesis in *Escherichia coli* in the Absence of Phospholipid Synthesis and Release of Inhibition by Thioesterase Action," Journal of Bacteriology, vol. 176, No. 10, May 1994, pp. 2814-2821.
Johnson, et al., "Genetic Analysis of the Role of *Saccharomyces cerevisiae* Acyl-CoA Synthetase Genes in Regulating Protein N-Myristoylation*," The Journal of Biological Chemistry, vol. 269, No. 27, Issue of Jul. 1994, pp. 18037-18046, 10 pages.
Johnston et al., "Isolation of the yeast regulatory gene GAL4 and analysis of its dosage effects on the galactose/melibiose regulon," Proc. Natl. Acad. Sci. USA 79(22): 6971 (1982).
Jones et al., "Palmitoyl-Acyl Carrier Protein (ACP) Thioesterase and the Evolutionary-Origin of Plant Acyl-ACP Thioesterases", Plant Cell, vol. 7:359-371 (1995).
Joshi et al., "Flow properties of biodiesel fuel blends at low temperatures", Fuel 86: 143-151 (2007).
Juttner et al., "The reducing capacities of cyanobacteria for aldehydes and ketones," Appl. Microbiol. Biotechnol. 25, pp. 52-54, 1986.
Kalscheuer et al., "A Novel Bifunctional Wax Ester Synthase/Acyl-CoA:Diacylglycerol Acyltransferase Mediates Wax Ester and Triacylglycerol Biosynthesis in Acinetobacter alcoaceticus ADPI," J. Biol. Chem. 278:8075-8082, 2003.
Kalscheuer et al., "A Novel Bifunctional Wax Ester Synthase/Acyl-CoA:Diacylglycerol Acyltransferase Mediates Wax Ester and Triacylglycerol Biosynthesis in Acinetobacter calcoacetius ADPI," J. Biol. Chem. 278(10): 8076-8082 (2003).
Kalscheuer et al., "Analysis of Storage Lipid Accumulation in Alcanivorax borkumensis:Evidence for Alternative Triacylglycerol Biosynthesis Routes in Bacteria," J. Bacteriol. 189(3): 918-923 (2007).
Kalscheuer et al., "Microdiesel: *Escherichia coli* Engineered for Fuel Production," Microbiology 152: 2529-2536 (2006).
Kalscheuer et al., "Neutral Lipid Biosynthesis in Engineered *Escherichia coli*: Jojoba Oil-like Wax Esters and Fatty Acid Butyl Esters," Applied and Environmental Microbiology, vol. 72, No. 2, Feb. 1, 2006, pp. 1373-1379.
Kalscheuer et al., "Synthesis of Novel Lipids in *Saccharomyces cerevisiae* by Heterologous Expression of an Unspecific Bacterial Acyltransferase" Appl. Environ. Microbiol., 70(12):7119-7125 (2004).
Kameda et al., "Further purification, characterization and salt activation of acyl-CoA synthetase from *Escherichia coli*", Biochimica et Biophysica Acta 840: 29-36(1985).
Kaneda. "Iso- and anteiso-fatty acids in bacteria: biosynthesis, function, and taxonomic significance." Microbiol. Rev. 55(2): 288 (1991).
Keasling et al., "Metabolic engineering delivers next-generation biofuels", Nature Biotechnology 26(3):298-299 (2008).
Knoll et al., "Biochemical Studies of Three *Saccharomyces cerevisiae* Acyl-CoA Synthetases, Faa1p, Faa2p, and Faa3p," J. Biol. Chem. 269(23): 16348-16356 (1994).
Knoll et al., "Use of *Escherichia coli* Strains Containing fad Mutations plus a Triple Plasmid Expression System to Study the Import of Myristate, Its Activation by *Saccharomyces cerevisiae* Acyl-CoA Synthetase, and Its Utilization by *S. cerevisiae* Myristoyl-Coa:Protein N-Myristoyltransferase," The Journal of Biological Chemistry, vol. 268, No. 6, Feb. 25, 1993, pp. 4281-4290.
Knoll, et al., "Biochemical Studies of Three *Saccharomyces cerevisiae* Acyl-CoA Synthetases, Faa1p, Faa2p, and Faa3p," J. Biol. Chem. 269(23): 16348-16356 (1994).
Knothe et al., "Kinematic viscosity of biodiesel components (fatty acid alkyl esters) and related compounds at low temperatures," Fuel 86: 2560-2567 (2007).
Knothe et al., "Kinematic viscosity of biodiesel fuel components and related compounds. Influence of compound structure and comparison to petrodiesel fuel components", Fuel 84:1059-1065 (2005).
Knothe, "Dependence of Biodiesel Fuel Properties on the Structure of Fatty Acid Alkyl Esters," Fuel Process. Technol., 86: 1059-1070 (2005).
Knothe, "Designer Biodiesel: Optimizing Fatty Ester Composition to Improve Fuel Properties," Energy & Fuels, 22: 1358-1364 (2008).
Knudsen et al,. "Transacylation as a chain-termination mechanism in fatty acid synthesis by mammalian fatty acid synthetase. Synthesis of medium-chain-length (C8-C12) acyl-CoA esters by goat mammary-gland fatty acid synthetase", Biochem. J. 202: 139-143 (1982).
Koffas, M.A.G., "Expanding the repertoire of biofuel alternatives through metabolic pathway evolution", PNAS 106(4): 965-966 (2009).
Kolkman et al., "Directed evolution of proteins by exon shuffling," Nat Biotechnol. 19:423-428 (2001).
Kumari et al., "Regulation of Acetyl Coenzyme A Synthetase in *Escherichia coli*", J. Bacteriol. 182(15): 4173-4179 (2000).
Ladyinga et al., "A review on microbial synthesis of hydrocarbons," Process Biochemistry, vol. 41, 2006, pp. 1001-1014.
Lang et al., "Preparation and characterization of bio-diesels from various bio-oils", Bioresource Tech. 80: 53-62 (2001).
Lee et al., "Enhanced preference for .pi.-bond containing substrates is correlated to Pro110 in the substrate-binding tunnel of *Escherichia coli* thioesterase I/protease I/*lysophospholipase* L.sub.1" Biochim. Et Biophys. Acta, 1774: 959-967 (2007).
Lee et al., "Metabolic engineering of microorganisms for biofuels production: from bugs to synthetic biology to fuels", Current Opinion in Biotechnology 19: 556-563 (2008).
Lee et al., "Prospects for Biodiesel as a Byproduct of Wood Pulping—A review," Peer-reviewed Review Article, ncsu.edu. bioresources,vol. 1, No. 1, 2006, pp. 150-171.
Lennen et al., "A Process for Microbial Hydrocarbon Synthesis: Overproduction of Fatty Acids in *Escherichia coli* and Catalytic Conversion to Alkane", Biotech.Bioengineering 106 (2):193-202 (2010).
Leonard et al., "A Cuphea .beta.-ketoacyl-ACP synthase shifts the synthesis of fatty acids towards shorter chains in *Arabidopsis* seeds expressing Cuphea FatB thioesterases", Plant Journal 13(5): 621-628 (1998).
Li et al., "Alteration of the Fatty Acid Profile of Streptomyces Coelicolor by Replacement of the Initiation Enzyme 3-Ketoacyl Acyl Carrier Protein Synthase III (FabH)," J. Bacteriol. 187(11): 3795-3799 (2005).
Li et al., "Conversion of Fatty Aldehydes to Alka(e)nes and Formate by a Cyanobacterial Aldehyde Decarbonylase: Cryptic Redox by an Unusual Dimetal Oxygenase", J. Am. Chem. Soc. 133: 6158-6161 (2011).

(56) References Cited

OTHER PUBLICATIONS

Li et al., "Growth Rate Regulation of *Escherichia coli* Acetyl Coenzyme a Carboxylase, Which Catalyzes the First Committed Step of Lipid Biosynthesis", J. Bacteriol. 175(2): 332-340 (1993).
Li et al., "Purification, Characterization, and Properties of an Aryl Aldehyde Oxidoreductase from *Nocardia* Sp. Strain NRRL 5646," Journal of Bacteriology, Jun. 1997, pp. 3482-3487, 6 pages.
Li et al., "The carboxylic acid reduction pathway in Nocardia. Purification and characterization of the aldehyde reductase", J. of Industrial Microbiology & Biotechnology 25: 328-332 (2000).
Li et al., "The Gene Encoding the Biotin Carboxylase Subunit of *Escherichia coli* Acetyl-CoA carboxylase", J.Biol.Chem. 267(2): 855-863 (1992).
Liao et al., "Production of 2-methyl-1-butanol in engineered *Escherichia coli*," Appl. Microbiol Biotechnol. 81(2): 89-98 (2008).
Link et al., "Methods for Generating Precise Deletions and Insertions in the Genome of Wild-Type *Escherichia coli*: Application to Open Reading Frame Characterization," J. Bacteriol. 179(20): 6228-6237 (1997).
Liu, et al., "Production and secretion of fatty acids in genetically engineered cyanobacteria" PNAS Early Edition: 1-6 (2010).
Lu et al., "Overproduction of free fatty acids in *E. coli*: Implications for biodiesel production," Metabolic Engineering 10: 333-339 (2008).
Lykidis et al., "Genomic Prospecting for Microbial Biodiesel Production," NN, Jun. 2008, 41 pages.
Mackey et al., "Detection of Rhythmic Bioluminescence from Luciferase Reporters in Cyanobacteria," Methods in Molecular Biology, Bol. 362, 2007, 16 pages.
Magnuson et al., "Regulation of Fatty Acid Biosynthesis in *Escherichia coli*," Microbiological Review, Sep. 1993, pp. 522-542, vol. 57, No. 3.
Marrakchi, et al., "A New Mechanism for Anaerobic Unsaturated Fatty Acid Formation in *Streptococcus pneumoniae*\*," The Journal of Biological Chemistry, vol. 277, No. 47, Issue of Nov. 2002, pp. 44809-44816, 6 pages.
Marrakchi, et al., "Mechanistic Diversity and Regulation of Type II Fatty Acid Synthesis," Biochem. Soc. Trans. 30(6): 1050-1055 (2002).
Massengo-Tiasse et al., "Vibrio cholerae FabV Defines a New Class of Enoyl-Acyl Carrier Protein Reductase", J. Biol. Chem. 283(3): 1308-1316 (2008).
Mat-Jan et al., "Mutants of *Escherichia coli* Deficient in the Fermentative Lactate Dehydroaenase," J. Bacterial. 171 (1):342-8 (1989).
Matsumoto et al., "Yeast whole-cell biocatalyst contructed by intracellular overproduction of Rhizopus oryzae lipase is applicable to biodiesel fuel production," Appl Microbiol Biotechnol, 57(4): 515-520 (2001).
Mayer et al., "Identification of amino acid residues involved in substrate specificity of plant acyl-ACP thioesterases using a bioinformatics-guided approach" BMC Plant Biology 7: 1-11 (2007).
McCue, L. et al., "hylogenetic footprinting of transcription factor binding sites in proteobacterial genomes," Nucleic Acids Res., 29(3):774-82(2001).
McCue, L. et al., "Phylogenetic footprinting of transcription factor binding sites in oroteobacterial aenomes," Nucleic Acids Res., 29(3):774-82 (2001).
McKnight. "Functional relationships between transcriptional control signals of the thymidine kinase gene of herpes simplex virus," Cell 31:355, 1982.
Metz et al., "Purification of a Jojoba Embryo Fatty Acyl-Coenzyme A Reductase and Expression of Its cDNA in High Erucic Acid Rapeseed", Plant Physiol. 122: 635-644 (2000).
Metzgar et al., "*Acinetobacter* sp. ADP1: an ideal model organism for genetic analysis and genome engineering", Nucleic Acid Res. 32(19):5780-5790 (2004).
Miller et al., "A Highly Catalytic and Selective Conversion of Carboxylic Acids to 1-Alkenes of One Less Carbon Atom," J. Org. Chem, 58(1): 18-20 (1993).

Mohan et al., "An *Escherichia coli* Gene (FabZ) Encoding (3R)-Hydroxymyristoyl Acyl Carrier Protein Dehydrase. Relation to fubA and Suppression of Mutations in Lipid A Biosynthesis", J.Biol.Chem 269(52): 32896-32903 (1994).
Morgan-Kiss et al., "The *Escherichia coli* fadK (ydiD) Gene Encodes an Anerobically Regulated Short Chain Acyl-CoA Synthetase\*," The Journal of Biological Chemistry, vol. 279, No. 36, Sep. 2004, pp. 37324-37333.
Morgan-Kiss et al., "The Lactococcus lactis FabF Fatty Acid Synthetic Enzyme can Functionally Replace both the FabB and FabF Proteins of *Escherichia coli* and the FabH Protein of Lactococcus lactis," Arch. Microbiol. 190: 427-437 (2008).
Mudge, "Fatty Alcohols—a review of their natural synthesis and environmental distribution," School of Ocean Sciences, University of Wales Bangor(Nov. 2005), pp. 1-151.
Murli et al., "A Role for the umuDC Gene Products of *Escherichia coli* in Increasing Resistance to DNA Damage in Stationary Phase by Inhibiting the Transition to Exponential Growth," J. Bacteriol. 182(4): 1127-1135 (2000).
Naccarato et al., "In Vivo and In Vitro Biosynthesis of Free Fatty Alcohols in *Escherichia coli* K-12," Lipids 9(6): 419-428 (1973).
NCBI Reference Sequence YP.sub.—889972.1, Putative Long-Chain Fatty-Acid-CoA Ligase [Microbacterium Smegmatis Str. MC2 155], retrieved from http://www.ncbi.nlm.nih.gov/protein/118469671, 4 pages.
NCBI Reference, Putative Alcohol Dehydrogenase [*Acinetobacter* sp. ADP1], 2010, retrieved from http://ncbi.nlm.nih.gov/protein/49532534.
NCBI Reference, Putative Alcohol Dehydrogenase [*Acinetobacter* sp. ADP1], 2010, retrieved from http://ncbi.nlm.nih.gov/protein/49532534, pp. 1-3.
Ness et al., "Molecular breeding: The natural approach to protein design," Adv Protein Chem. 55: 261-292 (2000).
Non-Final Office Action on U.S. Appl. No. 12/278,957 dated Nov. 16, 2016.
Non-Final Office Action on U.S. Appl. No. 12/768,419, dated Feb. 19, 2016.
Non-Final Office Action on U.S. Appl. No. 13/870,426, dated Oct. 13, 2015.
Notice of Allowance on U.S. Appl. No. 13/870,426 dated Nov. 16, 2016.
Nunn et al., "Role for fadR in Unsaturated Fatty Acid Biosynthesis in *Escherichia coli*", J.Bacteriol. 154(2):554-560 (1983).
Nunn et al., "Transport of long-chain fatty acids by *Escherichia coli*: Mapping and characterization of mutants in the fadL gene" PNAS 75(7): 3377-3381 (1978).
Office Action issued on Canadian Application 2678915, dated Mar. 8, 2017.
Office Action issued on Canadian Application 2722441, dated Sep. 24, 2015.
Office Action issued on Chinese Application 200880009283.9, dated May 10, 2016 English translation provided.
Office Action issued on Japanese application 2016-126210, dated Jun. 5, 2017, English translation.
Office Action issued on Mexican Application MX/a/2014/001863, dated Aug. 1, 2016.
Omelchenko et al., "Non-homologous isofunctinal enzymes: A systematic analysis of alterntive solutions in enzyme evolution," (2010) Biol. Direct 5, 20 pages.
Orlandi et al., "Cloning Immunoglobulin Variable Domains for Expression by the Polymerase Chain Reaction," Proc. Natl. Acad. Sci. USA 86(10): 3833-3837 (1989).
Palaniappan et al., "Enhancement and Selective Production of Phoslactomycin B, a Protein Phosphatase IIa Inhibitor, through Identification and Engineering of the Corresponding Biosynthetic Gene Cluster'," The Journal of Biological Chemistry 278(37): 35552-35557 (2003).
Patton, et al., "A Novel Il3, Il2-Enoyl-CoA Isomerase Involved in the Biosynthesis of the Cyclohexanecarboxylic Acid-Derived Moiety of the Polyketide Ansatrienin A,," Biochemistry 2000, 39, pp. 7595-7604, 10 pages.
Peng et al., "Effect of fadR gene knockout on the metabolism of *Escherichia coli* based on analyses of protein expressions, enzyme

(56) References Cited

OTHER PUBLICATIONS activities and intracellular metabolite concentrations" Enzyme and Microbial Tech. 38: 512-520 (2006).
Perez et al., "*Escherichia coli* YqhD Exhibits Aldehyde Reductase Activity and Protects from the Harmful Effect of Lipid Peroxidation-derived Aldehydes" J. Biol. Chem. 283(12): 7346-7353 (2008).
Peterson & Ingram, "Anaerobic Respiration in Engineered *Escherichia coli* with an Internal Electron Acceptor to Produce Fuel Ethanol," Ann. N. Y. Acad. Sci. 1125:363-372 (2008).
Phung et al., "Genes for Fatty Acids Biosynthesis in the Cyanobacterium *Synechococcus* sp. Strain PCC 7942," Jan. 1995, Abstracts of the General Meeting of the American Society of Microbiology, The Society, Washington, DC, p. 524, 1 page.
Pillai et al., "Functional characterization of .beta.-ketoacyl-ACP reductase (FabG) from Plasmodium falciparum" Biochem. and Biophysical Research Comm. 303: 387-392 (2003).
Qiu et al., "Crystal structure and substrate specificity of the .beta.-ketoacyl-acyl carrier protein synthase III (FabH) from *Staphylococcus aureus*," Protein Science 14: 2087-2094 (2005).
Rafi et al., "Structure of Acyl Carrier Protein Bound to FabI, the FASII Enoyl Reductase from *Escherichia coli*" J. Biol. Chem. 281(51): 39285-39293 (2006).
Rawlings et al., "Biosynthesis of fatty acids and related metabolites", Natural Product Reports 15: 275-308 (1998).
Rawlings et al., "The Gene Encoding *Escherichia coli* Acyl Carrier Protein Lies within a Cluster of Fatty Acid Biosynthetic Genes", J.Biol.Chem. 267(9):5751-5754 (1992).
Ray et al., "Activation of long chain fatty acids with acyl carrier protein: Demonstration of a new enzyme, acyl-acyl carrier protein synthetase, in *Escherichia coli*" PNAS 73(12):4374-4378 (1976).
Reading et al., "Quorum sensing: the many languages of bacteria," FEMS Microbiol Lett 254(1):1-11, 2006.
Rehm et al., "Heterologous expression of the acyl-acyl carrier protein thioesterase gene from the plant Umbellularia californica mediates polyhydroxyalkanoate biosynthesis in recombinant *Escherichia coli*", Appl. Microbiol. And Biotech. 55: 205-209 (2001).
Reiser et al., "Isolation of Mutants of Acinetobacter calcoaceticus Deficient in Wax Ester Synthesis of Complementation of One Mutation with a Gene Encoding a Fatty Acyl Coenzyme A Reductase," J. Bacteriol. 179(9): 2969-2975 (1997).
Ren et al., "FabG, an NADPH-Dependent 3-Ketoacyl Reductase of Pseudomonas aeruginosa, Provides Precursors for Medium-Chain-Length Poly-3-Hydroxyalkanoate Biosynthesis in *Escherichia coli*", J. Bacteriol.182(10):2978-2981 (2000).
Rock et al., "Acyl-Acyl Carrier Protein Synthetase from *Escherichia coli*", Meth.Enzymol. 71: 163-168 (1981).
Romero et al., "Metabolic Engineering of Bacillus Subtilis for Ethanol Production: Lactate Dehydrogenase Plays a Key Role in Fermentative Metabolism", Applied & Environmental Microbiology, 73(16): 5190-5198 (2007).
Rude et al., "New microbial fuels: a biotech perspective", Current Opinion in Microbiology 12: 274-281 (2009).
Rude et al., "Terminal Olefin (1-Alkene) Biosynthesis by a Novel P450 Fatty Acid Decarboxylase from *Jeotgalicoccus* Species", Appl. Environ. Microbiol. 77(5): 1718-1727 (2011).
Sabirova et al., "Mutation in a "tesB-Like" Hydroxyacyl-Coenzyme A-Specific Thioesterase Gene Causes Hyperproduction of Extracellular Polyhydroxyalkanoates by Alcanivorax borkumensis SK2," J. Bacteriol. 188(23): 8452-8459 (2006).
Saito et al., "Crystal structure of enoyl-acyl carrier protein reductase (FabK) from *Streptococcus neumonia* reveals the binding mode of an inhibitor", Protein Science 17: 691-699 ((2008).
Salas et al., "Characterization of substrate specificity of plant FatA and FatB acyl-ACP thioesterases," Archives of Biochem. and Biophysics 403: 25-34 (2002).
Sanchez et al., "Effect of Overexpression of a Soluble Pyridine Nucleotide Transhydrogenase (UdhA) on the Production of Poly(3-hydroxybutyrate) in *Escherichia coli*", Biotechnol.Prog. 22: 420-425 (2006).

Schujman et al., "A malonyl-CoA-dependent switch in the bacterial response to a dysfunction of lipid metabolism," Molecular Microbiology, 68(4): 987-996 (2008).
Schweizer et al., "Microbial Type I Fatty Acid Synthases (FAS): Major Players in a Network of Cellular FAS Systems", Microbiol. Mol.Biol.Rev. 68(3): 501-517 (2004).
Shahid et al., "A review of biodiesel as vehicular fuel", Renew. Sustain.Ener.Reviews 12: 2484-2494 (2008).
Shockey et al., "*Arabidopsis* Contains Nine Long-Chain Acyl-Coenzyme A Synthetase Genes that Participate in Fatty Acid and Glycerolipid Metabolism," Plant Physiology, Aug. 2002, vol. 129, pp. 1710-1722, 13 pages.
Shockey et al., "*Arabidopsis* Contains Nine Long-Chain Acyl-Coenzyme A Synthetase Genes that Participate in Fatty Acid and Glycerolipid Metabolism," Plant. Physiol. 29:1710-1722 (2002).
Silver et al., "Amino terminus of the yeast GAL4 gene product is sufficient for nuclear localization," Proc. Natl. Acad. Sci. USA 81(19): 5951 (1984).
Spencer et al., "Thioesterases I and II of *Escherichia coli*," J. Biol. Chem. 253(17): 5922-5926 (1978).
Stemmer "DNA shuffling by random fragmentation and reassembly: In vitro recombination for molecular evolution," (1994) Proc. Natl. Acad. Sci. U.S.A. 91:10747-10751.
Stephens et al., "The Pyruvate Dehydrogenase Complex of *Escherichia coli* K12," Eur. J. Biochem. 133:155-162, 1983.
Stoveken et al., "The Wax Ester Synthase/Acyl Coenzyme A:Diacylglycerol Acyltransferase from *Acinetobacter* sp. Strain ADP1: Characterization of a Novel Type of Acyltransferase", J. Bacteriology 187(4)1369-1376 (2005).
Subrahmanyam et al., "Overproduction of a Functional Fatty Acid Biosynthetic Enzyme Blocks Fatty Acid Synthesis in *Escherichia coli*," J. Bacteriol. 180(17): 4596-4602 (1998).
Sulzenbacher et al., "Crystal Structure of *E. coli* Alcohol Dehydrogenase YqhD: Evidence of a Covalently Modified NADP Coenzyme," J. Mol. Biol. 342: 489-502 (2004).
Ta et al., "Cloning, Sequencing, and Overexpression oaf [2Fe-2S] Ferredoxin Gene from *Escherichia coli*", J. Biol. Chem. 267(16): 11120-11125 (1992).
Technical Opinion issued on Brazilian Application PI0712205.5, dated Mar. 22, 2017.
Teerawanichpan et al., "Fatty Acyl-CoA Reductase and Wax Synthase from Euglena gracilis in the Biosynthesis of Medium-Chain Wax Esters", Lipids 45: 263-273 (2010).
Thomason et al., "Identification of the *Escherichia coli* K-12 ybhE Gene as pgl, Encoding 6-Phosphogluconolactonase" J.Bacteriol. 186(24): 8248-8253 (2004).
Thorpe et al., "Structure and mechanism of action of the Acyl-CoA dehydrogenases," FASEB J. 9: 718-725 (1995).
Tong et al., "Acetyl-Coenzyme A Carboxylases: Versatile Targets for Drug Discovery," J. Cellular Biochem. 99: 1476-1488 (2006).
Toomey et al., "Studies on the Mechanism of Fatty Acid Synthesis XVI. Preparation and General Properties of Acyl-Malonyl Acyl Carrier Proteincondensing Enzyme From *Escherichia coli*," J. Biol. Chem. 241(5)1159-1165 (1996).
Tsay et al., "Isolation and Characterization of the .beta.-Ketoacyl-acyl Carrier Protein Synthase I11 Gene (fabH) from *Escherichia coli* K-12", J.Biol.Chem. 267(10): 6807-6814 (1992).
Tucci et al., "A Novel Prokaryotic trans-2-enoyl-CoA reductase from the Spirochete Treponema denticola," FEBS Letters 581, 2007, pp. 1561-1566, 6 pages.
UniProt accession No. Q325A2 "Subname: Full=Acyl-CoA thioesterase I" (2005).
Vadali et al., "Cofactor engineering of intracellular CoA/acetyl-CoA and its effect on metabolic flux redistribution in *Escherichia coli*," Metabolic Engineering 6: 133-139 (2004).
Van Den Berg et al., "The FadL family: unusual transporters for unusual substrates", Curr. Opin. Struct. Biol. 15: 401-407 (2005).
Venkitasubramanian et al., "Reduction of Carboxylic Acids by Nocardia Aldehyde Oxidoreductase Requires a Phosphopantetheinylated Enzyme*," The Journal of Biological Chemistry, vol. 282, No. 1, pp. 478-485, Jan. 2007, 8 pages.

(56) References Cited

OTHER PUBLICATIONS

Vicente et al., Integrated biodiesel production: a comparison of different homogeneous catalysts systems, Bioresource Technology, vol. 92, No. 3, Jan. 1, 2004, pp. 295-305.
Voelker et al. "Alteration of the Specificity and Regulation of Fatty Acid Synthesis of *Escherichia coli* by Expression of a Plant Medium-Chain Acyl-Acyl Carrier Protein Thioesterase," J. Bacteriol. 176(23): 7320-7327 (1994).
Wang et al., "Functional Replacement of the FabA and FabB Proteins of *Escherichia coli* Fatty Acid Synthesis by Enterococcus faecalis FabZ and FabF Homologues," J. Biol. Chem. 279(33): 34489-34495 (2004).
Wang, (Biosynthetic pathway for poly(3-hydroxypropionate) in recombinant *Escherichia coli*., J Microbiol. (2012), vol. 50(4), pp. 693-697.
White et al., "Carboxylic acid reductase: a new tungsten enzyme catalyzes the reduction of non-activated carboxylic acids to aldehydes," Eur. J. Biochem. 184: 89-96 (1989).
Xu et al., "The FadRzDNA Complex. Transcriptional Control of Fatty Acid Metabolism in *Escherichia coli*", J.Biol.Chem.276(20): 17373-17379, 2001.
Yomano, L.P. et al., "Re-Engineering *Escherichia coli* for ethanol production," Biotechnol. Lett.30:2097-2103 (2008).
Yoo et al., "Determination of the native form of FadD, the *Escherichia coli* fatty acyl-CoA synthetase, and characterization of limited proteolysis by outer membrane protease OmpT", Biochem. J. 360: 699-706 (2001).
Yuan-Zheng, et al., Metabolic Engineering of Aeromonas hydrophila for the Enhanced Production of poly(3-hydroxybutyrate-co-3-hydroxyhexanoate), Appl. Microbial. Biotechnol., 2006,69, pp. 537-532.
Zang, et al., "Optimum Conditions for Transformation of *Synechocystis* sp. PCC 6803," The Journal of Microbiology, Jun. 2007, vol. 45, No. 3, DD. 241-245.
Zhang et al., "Inhibiting Bacterial Fatty Acid Synthesis", J.Biol. Chem. 281(26): 17541-17544 (2006).
Zhang et al., "Molecular Effect of FadD on the Regulation and Metabolism of Fatty Acid in *Escherichia coli*," FEMS Microbiol Lett, 259, 2006, pp. 249-253.
Zhang et al., "Structural Basis for Catalytic and Inhibitory Mechanisms of β-Hydroxpcyl-acyl Carrier Protein Dehydratase (FabZ)", J.Biol.Chem. 283(9):5370-5379 (2008).
Zhang et al., "The FabR (YijC) Transcription Factor Regulates Unsaturated Fatty Acid Biosynthesis in *Escherichia coli*\*," J. Biol. Chem. 277(18): 15558-15565 (2002).
Zhang, et al. "Molecular effect of FadD on the regulation and metabolism of fatty acid in *Escherichia coli*," FEMS Microbiol. Lett., 259(2): 249-253 (2006).
Zheng et al., "Thioesterase II of *Escherichia coli* Plays an Important Role in 3-Hydroxydecanoic Acid Production," Applied and Environmental Microbiology, vol. 70, No. 7, Jul. 2004, pp. 3807-3813, 7 pages.
Zhu et al., "Functions of the Clostridium acetobutylicium FabF and FabZ proteins in unsaturated fatty acid biosynthesis", BMC Microbiology 9:119 (2009).
Zimhony et al., "Characterization of Mycobacterium smegmatis Expressing the *Mycobacterium tuberculosis* Fatty Acid Synthase I (fas1) Gene", J.Bacteriology 186(13): 4051-4055 (2004).
Kizer et al., "Application of Functional Genomics to Pathway Optimization for Increased Isoprenoid Production," Applied and Environmental Microbiology, May 2008, pp. 3229-3241.
Non-Final Office Action on U.S. Appl. No. 14/661,219 dated Oct. 16, 2017.
Prather et al., "De novo biosynthentic pathways: rational design of microbial chemical factories," Current Opinion in Biotechnology 2008, vol. 19, pp. 468-474.
Office Action issued on Brazilian Application 0712205-5, dated Mar. 26, 2018.
Office Action issued on Canadian Application 2678915, dated Feb. 2, 2018.
Office Action issued on Chinese Application 201510244069.3, dated Jan. 29, 2018.
Office Action issued on Chinese Application 201610085050.3, dated Jul. 26, 2017.
Notification of Reexamination issued on Chinese Application 201080027865.7, dated Jul. 10, 2017.
Office Action issued on Japanese Application 2015-211435, dated Aug. 2, 2017 English translation only.
Allen, E.E. et al., "Structure and regulation of the omega-3 polyunsaturated fatty acid synthase genes from the deep-sea bacterium Photobacterium profundum strain SS9", Microbiology 148(6): 1903-1913 (2002).
Altschul et al., "Basic Local Alignment Search Tool," Journal of Molecular Biology 215(3): 403-410 (1990).
Benson, et al., "Development of a Heterogeneous Catalytic Cracking Reactor Utilizing Online Mass Spectrometry Analysis", J.Chromatography, vol. 1172(2): 204-208 (2007).
Brenda—Information on EC 3.1.2.14—oleoyl-[acyl-carrier-protein] hydrolase, Aug. 6, 2019.
Campbell et al., "A New *Escherichia coli* metabolic competency: growth on fatty acids by a novel anaerobic .beta.-oxidation pathway", Mol. Microbiol., 47(3): 793-805 (2003).
Chica, et al., "Semi-rational approaches to engineering enzyme activity: combining the benefits of directed evolution and rational design," Current Opinion in Biotechnology, 2005, vol. 16, pp. 378-384.
Cho et al., "*Escherichia coli* thioesterase I, molecular cloning and sequencing of the structural gene and identifications a periplasmic enzyme", J.Biol. Chem., vol. 268, No. 13, pp. 9238-9245, 1993.
Corpet, "Multiple sequence alignment with hierarchical clustering," Nucleic Acids Research 16(220: 10881-10890 (1988).
Costantino et al., "Enhanced levels of .lambda. Red-mediated recombinants in mismatch repair mutants," Proc. Natl. Acad. Sci. USA 100(26): 15748-15753 (2003).
Currie, "Source Apportionment of Atmospheric particles," Characterization of Environmental Particles, vol. 1 of the IUPAC Environmental Analytical Chemistry Series, pp. 3-74 (1992).
Da Silva et al., "Comparison of the Genomes of Two Xanthomonas Pathogens with Differing Host Specificities", Nature, 417: 459-463 (2002).
De Lay et al., "In Vivo Functional Analyses of the Type II Acyl Carrier Proteins of Fatty Acid Biosynthesis", J. Biol. Chem. 282: 20319-20328 (2007).
Dehesh et al., "Production of high levels of 8:0 and 10:0 fatty acids in transgenic canola by overexpression of Ch FatB2, a thioesterase cDNA from Cuphea hookeriana" The Plant Journal 9(2): 167-172 (1996).
Demirbas, A., "Progress and recent trends in biofuels", Progress in Energy and Combustion Science 33: 1-18 (2007).
Domergue et al., "Acyl Carriers Used as Substrates by the Desaturases and Elongases Involved in Very Long-chain Polyunsaturated Fatty Acids Biosynthesis Reconstituted in Yeast" J.Biol.Chem 278(37):35115-35126 (2003).
Doss, R.P., "Composition and Enzymatic Activity of the Extracellular Matrix Secreted by Germlings of Botrytis cinerea," Appl. and Environ. Microbiol., 65(2): 404-408 (1999).
European Search Report on EP Application 09013640.9, dated Jan. 25, 2010, 7 pages.
European Search report on EP Application 09013650.8, dated Aug. 23, 2010, 9 pages.
European Search Report on EP Application 11005423.6, dated Nov. 15, 2011, 7 pages.
European Search Report on EP Application 12194886.3, dated Apr. 24, 2013, 6 pages.
European Search Report on EP Application 12194886.3, dated Sep. 17, 2015, 7 pages.
European Search Report on EP Application 14193614.6, dated Mar. 5, 2015, 5 pages.
European Search Report on EP Application 18153966.9, dated Jun. 29, 2018, 13 pages.
Extended European Search Report on EP Application 14193614.6, dated Mar. 5, 2015, 6 pages.

(56) References Cited

OTHER PUBLICATIONS

Feng et al., "A New Member of the *Escherichia coli* fad Regulon: Transcriptional Regulation of fadM (ybaW)", J. Bacteriol. 191(20): 6320-6328 (2009).
Final Office Action on U.S. Appl. No. 12/278,957, dated Mar. 13, 2016, 22 pages.
Final Office Action on U.S. Appl. No. 12/278,957, dated May 1, 2017, 29 pages.
Final Office Action on U.S. Appl. No. 12/278,957, dated Nov. 8, 2011, 15 pages.
Final Office Action on U.S. Appl. No. 12/278,957, dated Sep. 15, 2014, 23 pages.
Final Office Action on U.S. Appl. No. 12/768,419, dated Aug. 19, 2015, 33 pages.
Final Office Action on U.S. Appl. No. 12/768,419, dated Jul. 14, 2016 11 pages.
Final Office Action on U.S. Appl. No. 12/768,419, dated Mar. 21, 2013, 31 pages.
Final Office Action on U.S. Appl. No. 13/099,986, dated Jul. 11, 2012, 9 pages.
Final Office Action on U.S. Appl. No. 13/529,990, dated May 23, 2014, 15 pages.
Fleischman et al., Putative long-chain fatty-acid—CoA ligase [*Mycobactcterium smegmatis* str. MC2 155], GenBank71854.1(2006).
Guo et al., Protein tolerance to random amino acid change, 2004, Proc. Natl. Acad. Sci. USA 101: 9205-9210.
Hancock et al., "SIMPLE34: an improved and enhanced implementation for VAX and Sun computers of the Simple algorithm for analysis of clustered repetitive motifs in nucleotide sequences," Comput. Appl. Biosci. 10: 67-70 (1994).
Heath et al., "Inhibition of .beta.-Ketoacyl-Acyl Carrier Protein Synthase III (FabH) by Acyl-Acyl Carrier Protein in *Escherichia coli*", J.Biol. Chem.271(18):10996-11000 (1996).
Heath et al., "Roles of the FabA and FabZ .beta.-Hydroxyacyl-Acyl Carrier Protein Dehydratases in *Escherichia coli* Fatty Acid Biosynthesis", J.Biol.Chem. 271(44): 27795-27801 (1996).
Higgins et al. "Using CLUSTAL for Multiple Sequence Alignments," Meth. Enzymol. 266: 383-402 (1988).
Higgins et al., "CLUSTAL: a package for performing multiple sequence alignment on a microcomputer," Gene 73(1): 237-244 (1988).
Higgins et al., "Fast and sensitive multiple sequence alignments on a microcomputer," CABIOS Comms. 5(2): 151-153 (1989).
Hill et al., Functional Analysis of conserved Histidines in ADP-Glucose Pyrophosphorylase from *Escherichia coli*, 1998, Biochem. Biophys. Res. Comm. 244:573-577.
Hoffmann et al., "Heat-Induced Aggregation of β-Lactoglobulin: Role of the Free Thiol Group and Disulfide Bonds," J. Agric. Food Chem., 45(8):2942 (1997).
Holtzapple et al., "Biosynthesis of Isoprenoid Wax Ester in Marinobacter hydrocarbonoclasticus DSM 8798: Identification and Characterization of Isoprenoid Coenzyme A Synthetase and Wax Ester Synthases," J. Bacteriology 189(10): 3804-3812 (2007).
Horton, Ce et al. Heterologous expression of the *Saccharomyces cerevisiae* alcohol acetyltransferase genes in Clostridium acetobutylicum and *Escherichia coli* for the production of isoamyl acetate. 2003. Journal of Industrial Microbiology and Biotechnology. 30:427-432.
Howell et al., "(R)-Citramalate Synthase in Methanogenic Archaea," J. Bacteriol. 181(1): 331-333 (1999).
Huang et al., "Parallelization of a local similarity algorithm," CABIOS 8(2):155-165 (1992).
Huber et al., "Branched-Chain Fatty Acids Produced by Mutants of Streptomyces fradiae, Putative Precursors of the Lactone Ring of Tylosin," Antimicrob. Agents Chemother. 34(8): 1535-1541 (1990).
International Preliminary Report on Patentability for PCT/US2007/011923, dated Nov. 21, 2008, 12 pages.
International Preliminary Report on Patentability for PCT/US2010/032580, dated Nov. 1, 2011, 5 pages.
International Preliminary Report on Patentability on PCT/US2007/003736, dated Aug. 2009, 6 pages.
International Preliminary Report on Patentability on PCT/US2008/057127, dated Sep. 15, 2009, 6 pages.
International Preliminary Report on Patentability on PCT/US2008/058788, dated Sep. 29, 2009, 12 pages.
International Search Report and Written Opinion on PCT/US2007/003736, dated Aug. 24, 2007, 8 pages.
International Search Report and Written Opinion on PCT/US2007/011923, dated Feb. 22, 2008, 18 pages.
International Search Report and Written Opinion on PCT/US2008/057127, dated Sep. 5, 2008, 9 pages.
International Search Report and Written Opinion on PCT/US2008/058788, dated Jan. 27, 2009, 21 pages.
International Search Report and Written Opinion on PCT/US2009/004734, dated Nov. 17, 2009, 9 pages.
International Search Report and Written Opinion on PCT/US2009/044403, dated Sep. 25, 2009, 10 pages.
International Search Report and Written Opinion on PCT/US2009/044409, dated Jan. 29, 2010, 10 pages.
International Search Report and Written Opinion on PCT/US2009/59903, dated Jun. 2, 2010, 18 pages.
International Search Report and Written Opinion on PCT/US2009/59904, dated Apr. 5, 2010, 11 pages.
International Search Report and Written Opinion on PCT/US2010/032580, dated Jul. 6, 2010, 8 pages.
International Search Report and Written Opinion on PCT/US2010/050024, dated Jan. 27, 2011. 13 pages.
International Search Report and Written Opinion on PCT/US2010/050026, dated Jan. 6, 2011, 9 pages.
IPER—PCT/US2007/003736 (2007).
IUBMB Enzyme Nomenclature. EC 1.2.1.50. 1986. p. 1.
IUBMB Enzyme Nomenclature. EC 2.3.1.75. 1984. p. 1.
IUBMB Enzyme Nomenclature. EC 2.3.1.84. 1984. p. 1.
IUBMB Enzyme Nomenclature. EC 6.4.1.2. 1961. p. 1.
Jahreis et al., "Adaptation of sucrose Metabolism in the *Escherichia coli* Wild-Type Strain EC3132," J. Bacteriol. 184(19): 5307-5316 (2002).
Juttner et al., "Environmental Factors Affecting the Formation of Mesityloxide, Dimethylallylic Alcohol and Other Volatile Compounds Excreted by Anabaena cylindrica," Journal of General Microbiology, 1983, 129, pp. 407-412.
Kameda et al., "Purification and Characterization of Acyl Coenzyme A Synthetase from *Escherichia coli*," J. Bacteriol. Chem. 256(11): 5702-5707.
Kazan et al., "Effect of Glucose Concentration on the Growth Rate and Some Intracellular Components of a Recombinant *E. coli* Culture," Process Biochem. 30(3): 269-273 (1995).
Koksharova et al., "Genetic tools for cyanobacteria," Appl. Microbiol. Biotechnol. 58(2): 123-137 (2002).
Kornberg et al., "Routes for Fructose Utilization by *Escherichia coli*," J. Mol. Microbiol. Biotechnol. 3(3): 355-359 (2001).
Kroumova et al., "A pathway for the biosynthesis of straight and branched, odd- and even-length, medium-chain fatty acids in plants," Proc. Natl. Acad. Sci. USA 91: 11437-11441 (1994).
Lardizabal et al., "Purification of a Jojoba Embryo Wax Synthase, Cloning of its cDNA. & Production of High Levels of Wax in Seeds of Transgenic *Arabidopsis*," Plant Physiol. 122(3): 645-655 (2000).
Lazar et al., "Transforming Growth Factor a: Mutation of Aspartic Acid 47 and Leucine 48 Results in Different Biological Activity", 1988, Mol. Cell. Biol. 8:1247-1252.
Lerner et al., "Low copy number plasmids for regulated low-level expression of cloned genes in *Escherichia coli* with blue/white insert screening capability," Nucleic Acids Research 18(15): 4631 (1990).
Li et al., "Overexpression of a bacterial branched-chain a-keto acid dehydrogenase complex in *Arabidopsis* results in accumulation of branched-chain acyl-CoAs and alteration of free amino acid composition in seeds", Plant Science (Dec. 2003), vol. 165, Issue 6, , pp. 1213-1219.
Lin, "Fed-Batch Culture of a Metabolically Engineered *Escherichia coli* Strain Designed for High-Level Succinate Production and Yield Under Aerobic Conditions," Biotech. Engineering 90: 1-5 (2005).

(56) References Cited

OTHER PUBLICATIONS

Lynd et al., "Microbial Cellulose Utilization: Fundamentals and Biotechnology," Microbiol. Mol. Biol. Rev. 66(3): 506-577 (2002).
Lytle, "Involvement of Both Dockerin Subdomains in Assembly of the Clostridium thermocellum Cellulosome," J. Bacteriol. 180(24): 6581-6585 (1998).
Maniatis et al., "Regulation of Inducible and Tissue-Specific Gene Expression," Science 236: 1237-1245 (1987).
Marr et al., "Effect of Temperature on the Composition of Fatty Acids in *Escherichia coli*", J. Bacteriol. 84: 1260-1267 (1962).
McDaniel, C.A., et al., Mandibular Gland Secretions of the Male Beewolves *Philanthus crabroniformis*, *P. barbatus*, and *P. pulcher* (Hymenoptera: Sphecidea), 1992, Journal of Chemical Ecology, vol. 18, No. 1, pp. 27-37 (Year: 1992).
Metz, et al., "Purification of a Jojoba Embryo Fatty Acyl-Coenzyme A Reductase and Expression of Its cDNA in High Eruic Acid Rapeseed," Plant Physiology, Mar. 200, vol. 122, pp. 635-644.
Minshull et al., "Protein evolution by molecular breeding," Curr. Opin. Chem. Biol. 3: 284-290 (1999).
Moore, "Biosynthetic Studies of .omega.-Cycloheptyl Fatty Acids in Alicyclobacillus cycloheptanicus. Formation of Cycloheptanecarboxylic Acid from Phenylacetic Acid," J. Org. Chem. 62: 2173-2185 (1997).
Murata, "Modes of Fatty-Acid Desaturation in Cyanobacteria," Plant Cell Physiol. 33: 933-941 (1992).
Myong-Ok, J., "New Pathway for Long-Chain n-Alkane Synthesis via 1-Alcohol in Vibrio furnissii M1", Journal of Bateriology, 187:1426-1429, 2005.
Needleman and Wunsch, "A General Method Applicable to the Search for Similarities in the Amino Acid Sequence of Two Proteins," J. Mol. Biol. 48:443-453 (1970).
Nomura et al., "Coexpression of Genetically Engineered 3-Ketoacyl-ACP Synthase III (fabH) and Polyhydroxyalkanoate Synthase (phaC) Genes Leads to Short-Chain-Length-Medium-Chain-Length Polyhydroxyalkanoate Copolymer Production from Glucose in *Escherichia coli* JM109", Appl Environ. Microbiol. Feb. 2004, vol. 70(2), pp. 999-1007.
Non Final Office Action on U.S. Appl. No. 12/278,961, dated Nov. 10, 2010, 6 pages.
Non-Final Office Action on U.S. Appl. No. 14/952,720, dated Jul. 14, 2017, 18 pages.
Non-Final Office Action on U.S. Appl. No. 15/954,451 dated Oct. 11, 2019.
Non-Final Office Action on U.S. Appl. No. 12/278,957, dated Apr. 15, 2011, 11 pages.
Non-Final Office Action on U.S. Appl. No. 12/278,957, dated Dec. 24, 2014, 26 pages.
Non-Final Office Action on U.S. Appl. No. 12/278,957, dated May 30, 2015, 20 pages.
Non-Final Office Action on U.S. Appl. No. 12/278,960, dated Jun. 30, 2011, 11 pages.
Non-Final Office Action on U.S. Appl. No. 12/278,960, dated Oct. 15, 2010, 14 pages.
Non-Final Office Action on U.S. Appl. No. 12/768,419, dated Dec. 26, 2014, 32 pages.
Non-Final Office Action on U.S. Appl. No. 12/768,419, dated Mar. 30, 2017, 40 pages.
Non-Final Office Action on U.S. Appl. No. 12/768,419, dated Nov. 18, 2011, 31 pages.
Non-Final Office Action on U.S. Appl. No. 13/099,986, dated Dec. 6, 2011, 12 pages.
Non-Final Office Action on U.S. Appl. No. 13/529,990, dated Aug. 21, 2013, 12 pages.
Non-Final Office Action on U.S. Appl. No. 15/619,290, dated Oct. 27, 2017, 7 pages.
Notice of Acceptance on AU Application 2014200805, dated Sep. 4, 2015, 3 pages.
Notice of Allowance on U.S. Appl. No. 12/526,209, dated Jul. 26, 2013, 8 pages.
Notice of Allowance on U.S. Appl. No. 12/278,960, dated Nov. 23, 2011, 11 pages.
Notice of Allowance on U.S. Appl. No. 12/278,961, dated Dec. 12, 2011, 5 pages.
Notice of Allowance on U.S. Appl. No. 12/278,961, dated Jul. 14, 2011, 6 pages.
Notice of Allowance on U.S. Appl. No. 13/099,986, dated Aug. 21, 2012, 8 pages.
Notice of Allowance on U.S. Appl. No. 13/529,990, dated Jan. 28, 2015, 9 pages.
Notice of Allowance on U.S. Appl. No. 15/619,290, dated Mar. 14, 2018, 8 pages.
Nunn, W., "A Molecular View of Fatty Acid Catabolism in *Escherichia coli*", Microbiol.Rev.50(2): 179-192 (1986).
Office Action on AU Application 2007254151, dated May 22, 2012, 2 pages.
Office Action on AU Application 2008230735, dated Aug. 16, 2012, 4 pages.
Office Action on AU Application 2014200805, dated Mar. 26, 2015, 5 pages.
Office Action on BR Application PI0809345-8, dated Dec. 12, 2017, 12 pages, English language version of relevant parts only.
Office Action on BR Application PI0809345-8, dated Jun. 2, 2017, 24 pages with summary translation.
Office Action on CA Application 2678915, dated Dec. 7, 2015, 5 pages.
Office Action on CA Application 2759273, dated Mar. 31, 2016, 5 pages.
Office Action on CA Application 2759273, dated Nov. 23, 2016, 3 pages.
Office Action on CN 201610085050.3, dated Sep. 12, 2019.
Office Action on CN Application 200780025145.5, dated Nov. 17, 2015, 9 pages.
Office Action on CN Application 201080027865. 7, dated Jan. 30, 2015, 13 pages with translation.
Office Action on CN Application 201080027865. 7, dated May 15, 2014, 12 pages with translation.
Office Action on CN Application 201080027865.7, dated Dec. 14, 2016, 13 pages with translation.
Office Action on CN Application 201080027865.7, dated Mar. 16, 2016, 15 pages with translation.
Office Action on CN Application 201080027865.7, dated Sep. 22, 2015, 7 pages with translation.
Office Action on CN Application 201080027865.7, dated Sep. 30, 2018, 7 pages with translation.
Office Action on CN Application 201510244069.3, dated May 25, 2017, 16 pages.
Office Action on CN Application 201610085050.3, dated Feb. 1, 2019, 16 pages with translation.
Office Action on CN Application 201610085050.3, dated Nov. 3, 2016, 8 pages with translation.
Office Action on EP Application 07809 099.0, dated Mar. 2, 2014, 6 pages.
Office Action on EP Application 07809099.0, dated Apr. 26, 2010, 5 pages.
Office Action on EP Application 07809099.0, dated Feb. 6, 2013, 8 pages.
Office Action on EP Application 07809099.0, dated Jan. 7, 2011, 7 pages.
Office Action on EP Application 07809099.0, dated Jun. 22, 2009, 3 pages.
Office Action on EP Application 07809099.0, dated Nov. 18, 2009, 4 pages.
Office Action on EP Application 08744695.1, dated Apr. 20, 2012, 7 pages.
Office Action on EP Application 08744695.1, dated Feb. 17, 2010, 5 pages.
Office Action on EP Application 08744695.1, dated May 28, 2013, 7 pages.
Office Action on EP Application 08744695.1, dated Nov. 19, 2010, 4 pages.
Office Action on EP Application 09013640.9, dated May 7, 2012, 5 pages.

(56) References Cited

OTHER PUBLICATIONS

Office Action on EP Application 09013640.9, dated Sep. 20, 2010, 1 page.
Office Action on EP Application 09013650.8, dated Jul. 11, 2012, 6 pages.
Office Action on EP Application 09013650.8, dated Jun. 11, 2013, 5 pages.
Office Action on EP Application 09747776.4, dated Aug. 28, 2015 3 pages.
Office Action on EP Application 11005423.6, dated Jul. 5, 2012, 6 pages.
Office Action on EP Application 11005423.6, dated Nov. 11, 2013, 5 pages.
Office Action on EP Application 12194886.3, dated May 16, 2014, 7 pages.
Office Action on EP Application 14193614.6, dated Jan. 9, 2018, 4 pages.
Office Action on in Application 6112/DELNP/2009, dated May 1, 2015, 7 pages.
Office Action on in Application 734/DELNP/2014, dated Nov. 20, 2018, 5 pages.
Office Action on in Application 9257/DELNP/2011, dated Oct. 6, 2017, 7 pages.
Office Action on in Application 9659/DELNP/2008, dated Nov. 1, 2013, 4 pages.
Office Action on JP 2015-211435, dated Aug. 26, 2019, 12 pages with translation.
Office Action on JP 2018-207088, dated Sep. 2, 2019, 8 pages with translation.
Office Action on JP Application 2009-511091, dated Aug. 2, 2012, 6 pages with translation.
Office Action on JP Application 2009-511091, dated Feb. 4, 2014, 5 pages with translation.
Office Action on JP Application 2009-511091, dated Jan. 29, 2013, 7 pages with translation.
Office Action on JP Application 2009-511091, dated Sep. 28, 2015, 11 pages with translation.
Office Action on JP Application 2010-501269, dated Apr. 1, 2014, 5 pages with translation.
Office Action on JP Application 2010-501269, dated May 21, 2013, 10 pages with translation.
Office Action on JP Application 2010-501269, dated Sep. 9, 2015, 7 pages with translation.
Office Action on JP Application 2014-115874, dated Aug. 5, 2015, 8 pages with translation.
Office Action on JP Application 2014-249577, dated Nov. 28, 2016, 5 pages with translation.
Office Action on JP Application 2015-211435, dated Aug. 22, 2016, 6 pages with translation.
Office Action on JP Application 2015-211435, dated Feb. 14, 2019, 6 pages with translation.
Office Action on JP Application 2016-126210, dated Sep. 12, 2016, 13 pages with translation.
Office Action on JP Application 2105-211435, dated Jul. 5, 2018, 6 pages with translation.
Office Action on MX MX/a/2016/017013, dated Sep. 5, 2017, 3 pages
Office Action on U.S. Appl. No. 12/526,209, dated Dec. 14, 2012, 8 pages.
Office Action on U.S. Appl. No. 12/526,209, dated Oct. 17, 2012, 9 pages.
Office Action on U.S. Appl. No. 12/768,419, dated Mar. 6, 2014, 27 pages.
Ohmiya, K. et al., "Application of Microbial Genes to Recalcitrant Biomass Utilization and Environmental Conservation", J. Bioscience and Bioengineering, vol. 95(6): 549-561 (2003).
Ovebath et al., "Fatty Acid Degradation in *Escherichia coli*," European J. Biochem, 7 1969, pp. 559-574.
Pages et al., "Interaction between the Endoglucanase CelA and the Scaffolding Protein CipC of the Clostridium cellulolyticum Cellulosome," J. Bacteriol. 178(8): 2279-2286 (1996).
Park, "New Pathway for Long-Chain n-Alkane Synthesis via 1-Alcohol in Vibrio furnissii M1," J. Bacteriol. 187: 1426-1429 (2005).
Partial International Search Report on PCT/US2008/058788, dated May 11, 2008, 4 pages.
Patton et al., "A Novel .DELTA..sup.3, .DELTA..sup.2-Enoyl-CoA Isomerase Involved in the Biosynthesis of the Cyclohexanecarbosylic Acid-Derived Moiety of the Polyketide Ansatrienin A," Biochemistry 39: 7595-7604 (2000).
Pearson et al., "Improved tools for biological sequence comparison," Proc. Natl. Acad. Sci. USA 85(8): 2444-2448 (1988).
Pearson et al., "Using the FASTA program to search protein and DNA sequence database," Methods Mol. Biol. 24:307-331 (1994).
Qiu et al., "Metabolic Engineering of Aeromonas hydrophilia for the Enhanced Production of Poly(3-hydroxybutyrate-co-3-hydroxyhexanoate)," Applied Microbiology & Biotechnology, 69(5): 537-542 (2006).
Rock et al., "Increased unsaturated fatty acid production associated with a suppressor of the fabA6(Ts) mutation in *Escherichia coli*," J. Bacteriol. 178(18): 5382-5387 (1996).
Rock et al., "Pathways for the incorporation of exogenous fatty acids into phosphatidylethanolamine in *Escherichia coli*.", The Journal of Biological Chemistry, vol. 260, No. 23, Oct. 15, 1985, pp. 12720-12724.
Ruyter et al., "Controlled Gene Expression Systems for Lactococcus lactis with the Food-Grade Inducer Nisin", Applied and Environmental Microbiology, vol. 62, No. 10, Oct. 1996, pp. 3662-3667.
Sambrook et al., "Molecular Cloning: A Laboratory Manual," 1989, 2nd Ed., Cold Spring Harbor Laboratory Press, Cold Spring Harbor, NY.
Schirmer et al., "Microbial iosynthesis of Alkanes", Science 329:559•562 (2010).
Schneider-Belhaddad et al., "Solubilization, Partial Purification, and Characterization of a Fatty Aldehyde Decarbonylase from a Higher Plant, Pisum sativum," Archives Biochem. Biophys. 377(2): 341-349 (2002).
Shockey et al., "*Arabidopsis* Contains a Large Superfamily of Acyl-Activating Enzymes. Phylogenetic and Biochemical Analysis Reveals a New Class of Acyl-Coenzyme A Synthetases," Plant Physiol. 132(2): 1065-1076 (2003).
Singh, et al., "Protein Engineering Approaches in the Post-Genomic Era," Current Protein Peptide Science 2017, vol. 18, pp. 1-11.
Smith et al., "Comparison of Biosequences," Advances in Applied Mathematics 2(4):482-489 (1981).
Soriano et al., "Crystallization behavior of neat biodiesel and biodiesel treated with ozonized vegetable oil", European Journal of Lipid Science and Technology, vol. 107, No. 9, Sep. 2005, pp. 689-696.
Steen et al., "Microbial production of fatty-acid-derived fuels and chemicals from plant biomass", Nature, vol. 463, No. 7280, Jan. 28, 2010, pp. 559-562.
Sukovich, Thesis, Hydrocarbon Biosynthesis by Bacteria: Genes and Hydrocarbon Products, 2010, 190 pages.
Supplementary European Search Report on EP Application 10762559.2, dated Oct. 5, 2015, 9 pages.
Supplementary European Search Report on EP Application 10770203.7, dated Dec. 3, 2012, 19 pages.
Thelen et al., Metabolic Engineering of Fatty Acid Biosynthesis in Plants, Metabolic Engineering 4, 12-21, 2002.
Thiel, "Genetic Analysis of cyanobacteria," in the Molecular Biology of Cyanobacteria, Advances in Photosynthesis and Respiration, Kluwer Academic Publishers, 581-611 (1994).
Twaig, Farouq A.A et al., "Performance of Composite Catalysts in Palm Oil Cracking for the Production of Liquid Fuels and Chemicals", Fuel Processing Technology, vol. 85: 1283-1300 (2004).
Valle et al., "Overexpression of Chromosomal Genes in *Escherichia coli*," Methods Mol. Biol. 267: 113-122 (2006).
Vanderhoeven et al., "Biosynthesis and Elongation of Short- and Medium-Chain-Length Fatty Acids," Plant Physiol. 122: 275-282 (2000).

(56) References Cited

OTHER PUBLICATIONS

Venturi, "Regulation of quorum sensing in Pseudomonas," FEMS Microbiol. Rev. 30: 274-291 (2006).
Voelker, et al., "Alteration of the Specificity and Regulation of Fatty Acid Synthesis of *Escherichia coli* by Expression of a Plant Medium-Chain Acyl-Acyl Carrier Protein Thioesterase," Journal of Bacteriology, Dec. 1994, vol. 176, No. 23, pp. 7320-7327.
Voss et al., "The role of enhancers in the regulation of cell-type-specific transcriptional control," Trends Biochem Sci., 11(7): 287-289 (1986).
Wacey et al., Disentangling the perturbational effects of amino acid substitutions in the DNA-binding domain of p53., Hum Genet, 1999, vol. 104, pp. 15-22.
Watson et al., "Molecular Biology of the Gene," 4th Ed., Benjamin Cummins (1987).
Weber et al., "13C-pattern of glycerol: Origin and practical importance", Journal of Agricultural and Food Chemistry, vol. 45, No. 6, 1997, pp. 2042-2046.
Wootton et al., "Statistics of local complexity in amino acid sequences and sequence databases," Computers in Chemistry 17: 149-163 (1993).
Wu et al., "Studies of Biosynthesis of Waxes by Developing Jojoba Seed: III. Biosynthesis of Wax Esters of Acyl CoA and Long Chain Alcohols," Lipids 16(12): 897-902 (1981).
Non-Final Office Action in U.S. Appl. No. 16/234,315 dated Jun. 4, 2020.
Final Office Action in U.S. Appl. No. 15/954,451 dated Apr. 20, 2020.
Preliminary Office Action in BR Patent Application No. PI1015313-6 dated Mar. 31, 2020 (with English translation) (6 pages).
Office Action on IN Application 201618015610, dated Dec. 16, 2019, 6 pages with translation.
White et al., "Production of Long-chain Alcohols by Yeasts". J. Gen. Microbio., 1987, vol. 133, Issue 8, pp. 2181-2090.
Partial Search Report in EP Patent Application No. 19192374.7 dated Feb. 18, 2020 (10 pages).
Office Action in CA Patent Application No. 3035878 dated Jan. 28, 2020 (4 pages).
Office Action in CN 201710052351.0 dated Feb. 3, 2020, 17 pages (with translation).
Final Office Action on U.S. Appl. No. 12/768,419 dated Dec. 1, 2017.
Fulda et al., "Two long-chain acyl-CoA synthetases from *Arabidopsis taliana* involved in peroxisomal fatty acid beta-oxidation," The Plant Journal, vol. 32, 2002, pp. 93-103.
GenBank Accession No. AAA34215, Mar. 2000, 2 pages (Year:2000).
Office Action issued on Chinese Appl. 201610085050.3, dated Jan. 29, 2018.
Foreign Search Report in EP Patent Application No. 19192374.7, dated Jun. 24, 2020 (11 pages).
Notice of Reasons for Rejection in JP Patent Application No. 2018-207088 dated Aug. 17, 2020 (with English Translation) (6 pages).
Office Action in BR Patent Application No. PI1015313-6 dated Jul. 14, 2020 (with English translation) (26 pages).

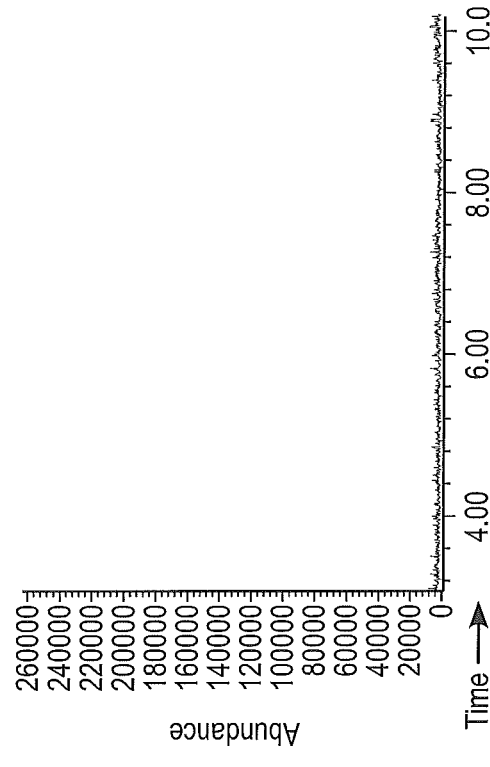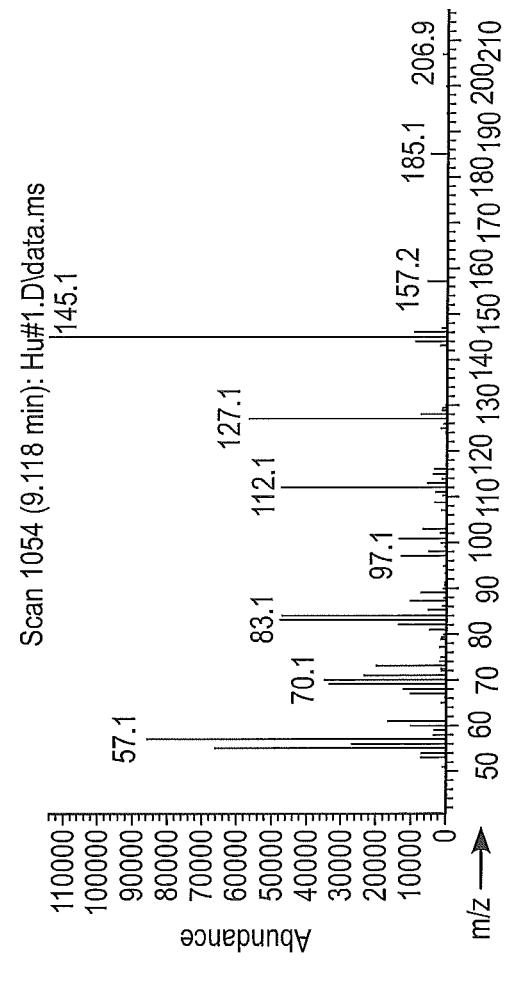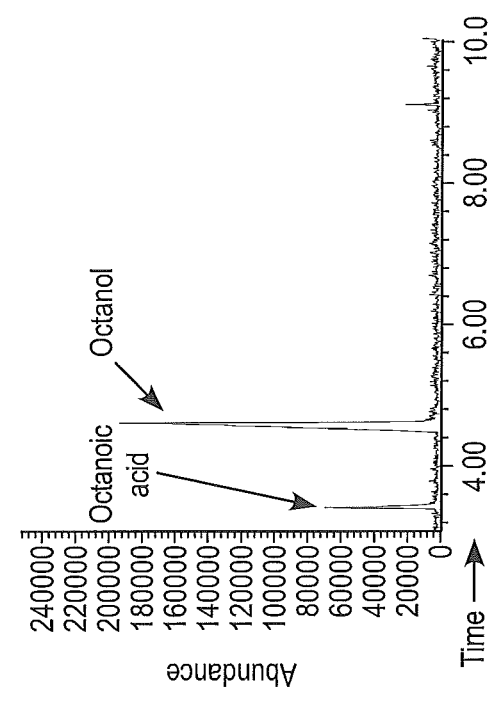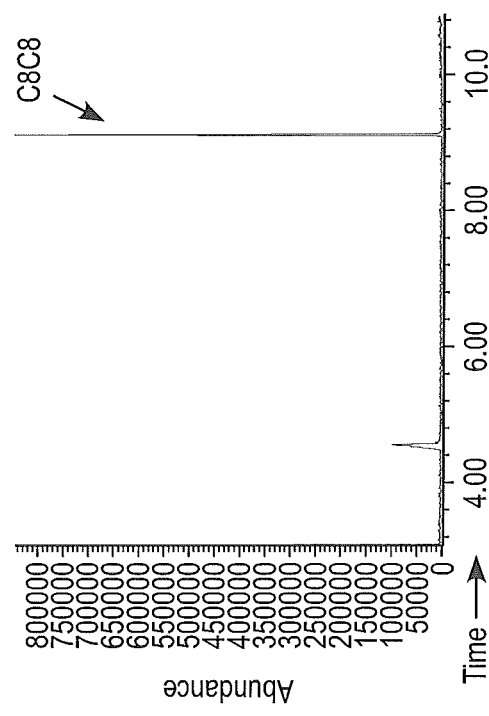

FIG. 10

*Accession Numbers are from NCBI, GenBank, Release 159.0 as of April 15 2007*
*EC Numbers are from KEGG, Release 42.0 as of April 2007 (plus daily updates up to and including the date of this patent)*

| CATEGORY | GENE | NAME | ACCESSION | EC NUMBER | MODIFICATION | USE | ORGANISM |
|---|---|---|---|---|---|---|---|
| 1. Fatty Acid Production Increase / Product Production Increase | | | | | | | |
| *increase acyl-CoA* | | | | | | | |
| *reduce catabolism of derivatives and intermediates* | | | | | | | |
| *reduce feedback inhibition* | | | | | | | |
| *attenuate other pathways that consume fatty acids* | | | | | | | |
| | accA | Acetyl-CoA carboxylase, subunit | AAC73296, NP_414727 | 6.4.1.2 | Over-express | increase Malonyl-CoA production | *Escherichia coli* |
| | accB | Acetyl-CoA carboxylase, subunit | NP_417721 | 6.4.1.2 | Over-express | increase Malonyl-CoA production | *Escherichia coli* |
| | accC | Acetyl-CoA carboxylase, subunit | NP_417722 | 6.4.1.2 | Over-express | increase Malonyl-CoA production | *Escherichia coli* |
| | accD | Acetyl-CoA carboxylase, subunit | NP_416819 | 6.4.1.2 | Over-express | increase Malonyl-CoA production | *Escherichia coli* |
| | aceE | pyruvate dehydrogenase, subunit E1 | NP_414656, AAC73226 | 1.2.4.1, 2.3.1.61, 2.3.1.12 | Over-express | increase Acetyl-CoA production | *Escherichia coli* |

FIG. 10 Cont.

| | | | | | |
|---|---|---|---|---|---|
| aceF | pyruvate dehydrogenase, subunit E2 | NP_414657, AAC73227 | 2.3.1.61, 2.3.1.12 | Over-express | increase Acetyl-CoA production | Escherichia coli |
| ackA | acetate kinase | AAC75356, NP_416799 | 2.7.2.1 | Delete or reduce | increase Acetyl-CoA production | Escherichia coli |
| ackB | acetate kinase AckB | BAB81430 | 2.7.2.1 | Delete or reduce | increase Acetyl-CoA production | Escherichia coli |
| acpP | acyl carrier protein | AAC74178 | NONE | Over-express | increase Acetyl-CoA production | Escherichia coli |
| fadD | acyl-CoA synthase | AP_002424 | 2.3.1.86 | Over-express | increase Fatty acid production | Escherichia coli W3110 |
| adhE | alcohol dehydrogenase | AAC74323, CAA47743 | 1.1.1.1, 1.2.1.10 | Delete or reduce | increase Acetyl-CoA production | Escherichia coli W3111 |
| cer1 | Aldehyde decarbonylase | BAA11024 | 4.1.99.5 | Over-express | increase Acetyl-CoA production | Arabidopsis thaliana |
| fabA | beta-hydroxydecanoyl thioester dehydrase | NP_415474 | 4.2.1.60 | express | fatty acyl-CoA production | E. coli K12 |
| fabD | [acyl-carrier-protein] S-malonyltransferase | AAC74176 | 2.3.1.39 | Over-express | increase Acetyl-CoA production | E. coli K12 |
| fabF | 3-oxoacyl-[acyl-carrier protein] synthase II | AAC74179 | 2.3.1.179 | Delete or OverExpress | increase Acetyl-CoA production | E. coli K12 |
| fabG | 3-oxoacyl-[acyl-carrier protein] reductase | AAC74177 | 1.1.1.100 | Over-express | increase Acetyl-CoA production | E. coli K12 |

FIG. 10 Cont.

| | | | | | |
|---|---|---|---|---|---|
| fabH | 3-oxoacyl-[acyl-carrier-protein] synthase III | AAC74175 | 2.3.1.180 | Over-express | increase Acetyl-CoA production | E. coli K12 |
| fabI | enoyl-[acyl-carrier-protein] reductase, NADH-dependent | NP_415804 | 1.3.1.9 | express | fatty acyl-CoA production | E. coli K12 |
| fabR | Transcriptional Repressor | NP_418398 | NONE | Delete or reduce | modulate unsaturated fatty acid production | E. coli K12 |
| fabZ | (3R)-hydroxymyristol acyl carrier protein dehydratase | NP_414722 | 4.2.1.- | | | E. coli K12 |
| fadE | acyl-CoA dehydrogenase | AAC73325 | 1.3.99.3, 1.3.99.- | Delete or reduce | increase Acetyl-CoA production | E. coli K12 |
| acr1 | Fatty Acyl-CoA reductase | AAC45217 | 1.2.1.- | Over-express | for fatty alcohol production | E. coli K12 |
| GST | Glutathione synthase | P04425 | 6.3.2.3 | Delete or reduce | increase Acyl-CoA | E. coli K12 |
| gpsA | biosynthetic sn-glycerol 3-phosphate dehydrogenase | AAC76632, NP_418065 | EC: 1.1.1.94 | Delete or reduce | increase Acetyl-CoA production | E. coli K12 |
| ldhA | lactate dehydrogenase | AAC74462, NP_415898 | EC: 1.1.1.28 | Delete or reduce | increase Acetyl-CoA production | E. coli K12 |
| Lipase | Triglyceride Lipase | CAA89087, CAA98876 | 3.1.1.3 | express | increase Fatty acid production | Saccharomyces cerevisiae |

FIG. 10 Cont.

| gene | enzyme | accession | EC | action | purpose | organism |
|---|---|---|---|---|---|---|
| | Malonyl-CoA decarboxylase | AAA26500 | 4.1.1.9, 4.1.1.41 | Over-express | | Saccharopolyspora erythraea |
| panD | aspartate 1-decarboxylase | BAB96708 | 4.1.1.11 | Over-express | increase Acyl-CoA | Escherichia coli W3110 |
| panK a.k.a. coaA | pantothenate kinase | AAC76952 | 2.7.1.33 | Over-express | increase Acetyl-CoA production | |
| pdh | Pyruvate dehydrogenase | BAB34380, AAC73226, NP_415392 | 1.2.4.1 | Over-express | increase Acetyl-CoA production | |
| pflB | formate acetyltransferase | AAC73989, P09373 | EC: 2.3.1.54 | Delete or reduce | increase Acetyl-CoA production | |
| plsB | acyltransferase | AAC77011 | 2.3.1.15 | D311E mutation | reduce limits on Acyl-CoA pool | E. coli K12 |
| poxB | pyruvate oxidase | AAC73958, NP_415392 | 1.2.2.2 | Delete or reduce | increase Acetyl-CoA production | |
| pta | phosphotransacetylase | AAC75357, NP_416800 | 2.3.1.8 | Delete or reduce | increase Acetyl-CoA production | |
| udhA | pyridine nucleotide transhydrogenase | CAA46822 | 1.6.1.1 | Over-express | convert NADH to NADPH or vice versa | |

FIG. 10 Cont.

| | | | | | | |
|---|---|---|---|---|---|---|
| fadB | fused 3-hydroxybutyryl-CoA epimerase/delta(3)-cis-delta(2)-trans-enoyl-CoA isomerase/enoyl-CoA hydratase & 3-hydroxyacyl-CoA dehydrogenase | AP_003956 | 4.2.1.17, 5.1.2.3, 5.3.3.8, 1.1.1.35 | Delete or reduce | Block fatty acid degradation | E. coli |
| fadJ | 3-hydroxyacyl-CoA dehydrogenase; K01692 enoyl-CoA hydratase; K01782 3-hydroxybutyryl-CoA epimerase | AAC75401 | 1.1.1.35, 4.2.1.17, 5.1.2.3 | Delete or reduce | Block fatty acid degradation | E. coli |
| fadA | 3-ketoacyl-CoA thiolase | BAE77458 | 2.3.1.16 | Delete or reduce | Block fatty acid degradation | E. coli |
| fadI | beta-ketoacyl-CoA thiolase | AAC75402 | 1.5.1.29, 1.16. | Delete or reduce | Block fatty acid degradation | E. coli |
| YdiO | acyl-coA dehydrogenase | YP_852786 | 1.3.99.- | Delete or reduce | Block fatty acid degradation | E. coli |

2. Structure Control

2A. Chain Length Control

| | | | | | | |
|---|---|---|---|---|---|---|
| 2 tesA | thioesterase | P0ADA1 | 3.1.2.- | Delete 1 and/or express | C18 Chain Length | |

FIG. 10 Cont.

| | | | | |
|---|---|---|---|---|
| tesA without leader sequence | thioesterase | AAC73596, NP_415027 | 3.1.1.- | express or overexpress | C18:1 | E.coli |
| fatB1 (umbellularia) | thioesterase | Q41635 | 3.1.1.- | express or overexpress | C12:0 | Umbellularia californica |
| fatB2 (umbellularia) | thioesterase | AAC49269 | 3.1.1.- | express or overexpress | C8:0 - C10:0 | Cuphea hookeriana |
| fatB3 | thioesterase | AAC72881 | 3.1.1.- | express or overexpress | C14:0 - C16:0 | Cuphea hookeriana |
| fatB (cinnamonum) | thioesterase | Q39473 | 3.1.1.- | express or overexpress | C14:0 | Cinnamomum camphora |
| fatB[M141T]* | thioesterase | CAA85388 | 3.1.1.- | express or overexpress | C16:1 | Arabidopsis thaliana |
| fatA1 (Helianthus) | thioesterase | AAL79361 | 3.1.1.- | express or overexpress | C18:1 | Helianthus annuus |
| atfata | thioesterase | NP_189147, NP_193041 | 3.1.1.- | express or overexpress | C18:1 | Arabidopsis thaliana |
| fatA | thioesterase | CAC39106 | 3.1.1.- | express or overexpress | C18:1 | Brassica juncea |
| fatA (cuphea) | thioesterase | AAC72883 | 3.1.1.- | express or overexpress | C18:1 | Cuphea hookeriana |

FIG.10 Cont.

2B. Branching Control

| | | | | |
|---|---|---|---|---|
| attenuate FabH | | | | |
| express FabH from S. glaucescens or S. coelicolor and knock out endogenouse FabH | | | increase branched chain fatty acid derivatives | |
| express FabH from B. subtilis and knock out endogenouse FabH | | | | |
| bdk-E3 –dihydro plipoyldehyrodgena se subunit | | EC 1.2.4.4 | | |
| bkd-E1-alpha /beta subunit | | EC 1.2.4.4 | | |
| bkd-E2 - dihydrolipoyl transacylase subunit | | EC 1.2.4.4 | | |
| bkdA1 | branched-chain α-ketoacid dehydrogenase a-subunit (E1a) | NP_628006 | EC 1.2.4.4 | express or Over-Express | make branched-chain acyl-CoA precursors | Streptomyces coelicolor |

FIG.10 Cont.

| | | | | | |
|---|---|---|---|---|---|
| bkdB1 | branched-chain α-ketoacid dehydrogenase a-subunit (E1b) | NP_628005 | EC 1.2.4.4 | express or Over-Express | make branched-chain acyl-CoA precursors | Streptomyces coelicolor |
| bkdC1 | dihydrolipoyl transacetylase (E2) | NP_638004 | EC 1.2.4.4 | express or Over-Express | make branched-chain acyl-CoA precursors | Streptomyces coelicolor |
| bkdA2 | branched-chain α-ketoacid dehydrogenase a-subunit (E1a) | NP_733618 | EC 1.2.4.4 | express or Over-Express | make branched-chain acyl-CoA precursors | Streptomyces coelicolor |
| bkdB2 | branched-chain α-ketoacid dehydrogenase b-subunit (E1b) | NP_628019 | EC 1.2.4.4 | express or Over-Express | make branched-chain acyl-CoA precursors | Streptomyces coelicolor |
| bkdC2 | dihydrolipoyl transacetylase (E2) | NP_628018 | EC 1.2.4.4 | express or Over-Express | make branched-chain acyl-CoA precursors | Streptomyces coelicolor |
| bkdA | branched-chain α-ketoacid dehydrogenase a-subunit (E1a) | BAC72074 | EC 1.2.4.4 | express or Over-Express | make branched-chain acyl-CoA precursors | Streptomyces avermitilis |
| bkdB | branched-chain α-ketoacid dehydrogenase b-subunit (E1b) | BAC72075 | EC 1.2.4.4 | express or Over-Express | make branched-chain acyl-CoA precursors | Streptomyces avermitilis |

FIG. 10 Cont.

| | | | | | |
|---|---|---|---|---|---|
| bkdC | dihydrolipoyl transacetylase (E2) | BAC72076 | EC 1.2.4.4 | express or Over-Express | make branched-chain acyl-CoA precursors | *Streptomyces avermitilis* |
| bkdF | branched-chain α-ketoacid dehydrogenase a-subunit (E1a) | BAC72088 | EC 1.2.4.4 | express or Over-Express | make branched-chain acyl-CoA precursors | *Streptomyces avermitilis* |
| bkdG | branched-chain α-ketoacid dehydrogenase b-subunit (E1b) | BAC72089 | EC 1.2.4.4 | express or Over-Express | make branched-chain acyl-CoA precursors | *Streptomyces avermitilis* |
| bkdH | dihydrolipoyl transacetylase (E2) | BAC72090 | EC 1.2.4.4 | express or Over-Express | make branched-chain acyl-CoA precursors | *Streptomyces avermitilis* |
| bkdAA | branched-chain α-ketoacid dehydrogenase a-subunit (E1a) | NP_390285 | EC 1.2.4.4 | express or Over-Express | make branched-chain acyl-CoA precursors | *Bacillus subtilis* |
| bkdAB | branched-chain α-ketoacid dehydrogenase b-subunit (E1b) | NP_390284 | EC 1.2.4.4 | express or Over-Express | make branched-chain acyl-CoA precursors | *Bacillus subtilis* |
| bkdB | dihydrolipoyl transacetylase (E2) | NP_390283 | EC 1.2.4.4 | express or Over-Express | make branched-chain acyl-CoA precursors | *Bacillus subtilis* |

FIG. 10 Cont.

| | | | | | |
|---|---|---|---|---|---|
| bkdA1 | branched-chain α-ketoacid dehydrogenase a-subunit (E1a) | AAA65614 | EC 1.2.4.4 | express or Over-Express | make branched-chain acyl-CoA precursors | *Pseudomonas putida* |
| bkdA2 | branched-chain α-ketoacid dehydrogenase b-subunit (E1b) | AAA65615 | EC 1.2.4.4 | express or Over-Express | make branched-chain acyl-CoA precursors | *Pseudomonas putida* |
| bkdC | dihydrolipoyl transacetylase (E2) | AAA65617 | EC 1.2.4.4 | express or Over-Express | make branched-chain acyl-CoA precursors | *Pseudomonas putida* |
| lpd | dihydrolipoamide dehydrogenase (E3) | NP_414658 | 1.8.1.4 | express or Over-Express | make branched-chain acyl-CoA precursors | *Escherichia coli* |
| IlvE | branched-chain amino acid aminotransferase | YP_026247 | 2.6.1.42 | express or Over-Express | make branched α-ketoacids | *Escherichia coli* |
| IlvE | branched-chain amino acid aminotransferase | AAF34406 | 2.6.1.43 | express or Over-Express | make branched α-ketoacids | *Lactococcus lactis* |
| IlvE | branched-chain amino acid aminotransferase | NP_745648 | 2.6.1.42 | express or Over-Express | make branched α-ketoacids | *Pseudomonas putida* |
| IlvE | branched-chain amino acid aminotransferase | NP_629657 | 2.6.1.42 | express or Over-Express | make branched α-ketoacids | *Streptomyces coelicolor* |

FIG.10 Cont.

| | | | | | |
|---|---|---|---|---|---|
| ccr | crotonyl-CoA reductase | NP_630556 | 1.1.1.9 | express or Over-Express | Converting crotonyl-CoA to butyryl-CoA | Streptomyces coelicolor |
| ccr | crotonyl-CoA reductase | AAD53915 | 1.1.1.9 | express or Over-Express | Converting crotonyl-CoA to butyryl-CoA | Streptomyces cinnamonensis |
| IcmA, isobutyryl-CoA mutase | isobutyryl-CoA mutase, subunit A | NP_629554 | 5.4.99.2 | express or Over-Express | converting butyryl-CoA to isobutyryl-CoA | Streptomyces coelicolor |
| IcmA, isobutyryl-CoA mutase | isobutyryl-CoA mutase, subunit A | AAC08713 | 5.4.99.2 | express or Over-Express | converting butyryl-CoA to isobutyryl-CoA | Streptomyces cinnamonensis |
| IcmB, isobutyryl-CoA mutase | isobutyryl-CoA mutase, subunit B | NP_630904 | 5.4.99.13 | express or Over-Express | converting butyryl-CoA to isobutyryl-CoA | Streptomyces coelicolor |
| IcmB, isobutyryl-CoA mutase | isobutyryl-CoA mutase, subunit B | AJ246005 | 5.4.99.13 | express or Over-Express | converting butyryl-CoA to isobutyryl-CoA | Streptomyces cinnamonensis |
| FabH, ACPs and fabF genes with specificity for branched chain acyl-CoAs | | | | | | |
| IlvE | | CAC12788 | EC2.6.1.42 | over express | branched chain amino acid amino transferase | S. carnosus |

FIG.10 Cont.

| FabH1 | beta-ketoacyl-ACP synthase III | NP_626634 | 2.3.1.180 | express or Over-Express | initiation of branched-chain fatty acid biosynthesis | Streptomyces coelicolor |
|---|---|---|---|---|---|---|
| ACP | acyl-carrier protein | NP_626635 | NONE | express or Over-Express | initiation and elongation of branched-chain fatty acid biosynthesis | Streptomyces coelicolor |
| FabF | beta-ketoacyl-ACP synthase II | NP_626636 | 2.3.1.179 | express or Over-Express | elongation of branched-chain fatty acid biosynthesis | Streptomyces coelicolor |
| FabH3 | beta-ketoacyl-ACP synthase III | NP_823466 | 2.3.1.180 | express or Over-Express | initiation of branched-chain fatty acid biosynthesis | Streptomyces avermitilis |
| FabC3 (ACP) | acyl-carrier protein | NP_823467 | NONE | express or Over-Express | initiation and elongation of branched-chain fatty acid biosynthesis | Streptomyces avermitilis |
| FabF | beta-ketoacyl-ACP synthase II | NP_823468 | 2.3.1.179 | express or Over-Express | elongation of branched-chain fatty acid biosynthesis | Streptomyces avermitilis |

FIG.10 Cont.

| | | | | | |
|---|---|---|---|---|---|
| FabH_A | beta-ketoacyl-ACP synthase III | NP_389015 | 2.3.1.180 | express or Over-Express | initiation of branched-chain fatty acid biosynthesis | *Bacillus subtilis* |
| FabH_B | beta-ketoacyl-ACP synthase III | NP_388898 | 2.3.1.180 | express or Over-Express | initiation of branched-chain fatty acid biosynthesis | *Bacillus subtilis* |
| ACP | acyl-carrier protein | NP_389474 | NONE | express or Over-Express | initiation and elongation of branched-chain fatty acid biosynthesis | *Bacillus subtilis* |
| FabF | beta-ketoacyl-ACP synthase II | NP_389016 | 2.3.1.179 | express or Over-Express | elongation of branched-chain fatty acid biosynthesis | *Bacillus subtilis* |
| SmalDRAFT_0818 | beta-ketoacyl-ACP synthase III | ZP_01643059 | 2.3.1.180 | express or Over-Express | initiation of branched-chain fatty acid biosynthesis | *Stenotrophomonas maltophilia* |
| SmalDRAFT_0821 | acyl-carrier protein | ZP_01643063 | NONE | express or Over-Express | initiation and elongation of branched-chain fatty acid biosynthesis | *Stenotrophomonas maltophilia* |

FIG. 10 Cont.

| | | | | | |
|---|---|---|---|---|---|
| SmalDRAFT_0822 | beta-ketoacyl-ACP synthase II | ZP_01643064 | 2.3.1.179 | express or Over-Express | elongation of branched-chain fatty acid biosynthesis | Stenotrophomonas maltophilia |
| FabH | beta-ketoacyl-ACP synthase III | YP_123672 | 2.3.1.180 | express or Over-Express | initiation of branched-chain fatty acid biosynthesis | Legionella pneumophila |
| ACP | acyl-carrier protein | YP_123675 | NONE | express or Over-Express | initiation and elongation of

FIG.10 Cont.

*To Produce Cyclic Fatty Acids*

| | | | | | |
|---|---|---|---|---|---|
| AnsJ | dehydratase (putative) | not available | not available | express or Over-Express | cyclohexylcarbonyl-CoA boiosynthesis | Streptomyces collinus |
| AnsK | CoA ligase (putative) | not available | not available | express or Over-Express | cyclohexylcarbonyl-CoA boiosynthesis | Streptomyces collinus |
| AnsL | dehydrogenase (putative) | not available | not available | express or Over-Express | cyclohexylcarbonyl-CoA boiosynthesis | Streptomyces collinus |
| ChcA | enoyl-CoA reductase | U72144 | EC 1.3.1.34 | express or Over-Express | cyclohexylcarbonyl-CoA boiosynthesis | Streptomyces collinus |
| AnsM | oxidorecutase (putative) | not available | not available | express or Over-Express | cyclohexylcarbonyl-CoA boiosynthesis | Streptomyces collinus |
| PlmJ | dehydratase (putative) | AAQ84158 | not available | express or Over-Express | cyclohexylcarbonyl-CoA boiosynthesis | Streptomyces sp. HK803 |
| PlmK | CoA ligase (putative) | AAQ84158 | not available | express or Over-Express | cyclohexylcarbonyl-CoA boiosynthesis | Streptomyces sp. HK803 |
| PlmL | dehydrogenase (putative) | AAQ84159 | not available | express or Over-Express | cyclohexylcarbonyl-CoA boiosynthesis | Streptomyces sp. HK803 |
| ChcA | enoyl-CoA reductase | AAQ84160 | EC 1.3.1.34 | express or Over-Express | cyclohexylcarbonyl-CoA boiosynthesis | Streptomyces sp. HK803 |

FIG. 10 Cont.

| | | | | | |
|---|---|---|---|---|---|
| PlmM | oxidorecutase (putative) | AAQ84161 | not available | express or Over-Express | cyclohexylcarbonyl-CoA boiosynthesis | Streptomyces sp. HK803 |
| ChcB | enoyl-CoA isomerase | AF268489 | not available | express or Over-Express | cyclohexylcarbonyl-CoA boiosynthesis | Streptomyces collinus |
| ChcB/CaiD | enoyl-CoA isomerase | NP_629292 | 4.2.1.- | express or Over-Express | cyclohexylcarbonyl-CoA boiosynthesis | Streptomyces coelicolor |
| ChcB/CaiD | enoyl-CoA isomerase | NP_824296 | 4.2.1.- | express or Over-Express | cyclohexylcarbonyl-CoA boiosynthesis | Streptomyces avermitilis |

2C. Saturation Level Control

| | | | | | |
|---|---|---|---|---|---|
| Sfa | Suppressor of FabA | AAN79592, AAC44390 | not available | Over-express | increase monounsaturated fatty acids | E.coli |
| also see FabA in sec. 1 | | | | express | produce unsaturated fatty acids | |
| GnsA | suppressors of the secG null mutation | ABD18647.1 | NONE | Over-express | increase unsaturated fatty acid esters | E.coli |
| GnsB | suppressors of the secG null mutation | AAC74076.1 | NONE | Over-express | increase unsaturated fatty acid esters | E.coli |

FIG.10 Cont.

| | | | | | |
|---|---|---|---|---|---|
| also see section 2A<br>- items with :0 are unsaturated (no double bonds) and with :1 are saturated (1 double bond) | | | | | |
| | fabB | 3-oxoacyl-[acyl-carrier-protein] synthase I | BAA16180 | EC:2.3.1.41 | overexpress | modulate unsaturated fatty acid production | Escherichia coli |
| | fabK | trans-2-enoyl-ACP reductase II | AAF98273 | 1.3.1.9 | express | modulate unsaturated fatty acid production | Streptococcus pneumoniae |
| | fabL | enoyl-(acyl carrier protein) reductase | AAU39821 | 1.3.1.9 | express | modulate unsaturated fatty acid production | Bacillus licheniformis DSM 13 |
| | fabM | trans-2, cis-3-decenoyl-ACP isomerase | DAA05501 | 5.3.3.14 | Over-express | modulate unsaturated fatty acid production | Streptococcus mutans |

3. Final Product Output

3A. Wax Output

| | | | | | |
|---|---|---|---|---|---|
| AT3G51970 | long-chain-alcohol O-fatty-acyltransferase | NP_190765 | 2.3.1.75 | express | wax production | Arabidopsis thaliana |

FIG.10 Cont.

| | | | | |
|---|---|---|---|---|
| | thioesterase (see chain length control section) | | 3.1.2.14 | express | increase fatty acid production |
| acr1 | fatty alcohol forming acyl-CoA reductase | | 1.1.1.* | express | convert Acyl-CoA to fatty alcohol |
| | acyl-CoA reductase (ACR1) | YP_047869 | 1.2.1.50 | express | convert Acyl-CoA to fatty alcohol | *Acinetobacter sp.* ADP1 |
| yqhD | alcohol dehydrogenase | AP_003562 | 1.1.1.1 | express | increase | *E. coli* W3110 |
| ELO1 | Fatty acid elongase | BAD98251 | 2.3.1.74 | express | produce very long chain length fatty acids | *Pichia angusta* |
| plsC | acyltransferase | AAA16514 | 2.3.1.- | express | | *Saccharomyces cerevisiae* |
| DAGAT | diacylglycerol acyltransferase | AAF19262 | 2.3.1.20 | express | wax production | *Arabidopsis thaliana* |
| hWS | acyl-CoA wax alcohol acyltransferase | AAX48018 | not available | express | wax production | *Homo sapiens* |
| aft1 | bifunctional wax ester synthase/acyl-CoA:diacylglycerol acyltransferase | AAO17391 | 2.3.1.20 | express | wax production | *Acinetobacter sp.* ADP1 |
| mWS | wax ester synthase (simmondsia) | AAD38041 | 2.3.1.75 | express | wax production | *Simmondsia chinensis* |

FIG. 10 Cont.

3B. Fatty Alcohol Output

| | | | | | |
|---|---|---|---|---|---|
| | various thioesterases (refer to Sec. 2A) | | 3.1.2.14 | express | produce |
| acr1 | Acyl-CoA reductase | YP_047869 | 1.2.1.50 | express | produce | Acinetobacter sp. ADP1 |
| yqhD | alcohol dehydrogenase | AP_003562 | 1.1.1.1 | express | produce | Escherichia coli W3110 |
| BmFAR | FAR (fatty alcohol forming acyl-CoA reductase) | BAC79425 | 1.1.1.* | express | reduce fatty acyl-CoA to fatty alcohol | Bombyx mori |
| Akr1a4 | Mammalian microsomal aldehyde reductase | NP_067448 | 1.1.1.21 | express | produce | Mus musculus |
| GTNG_1865 | Long-chain aldehyde dehydrogenase | YP_001125970 | 1.2.1.48 | express | produce | Geobacillus thermodenitrificans NG80-2 |
| FadD | Acyl-CoA synthetase | NP_416319 | EC 6.2.1.3 | express | produce more | E. Coli K12 |

To make Butanol

| atoB | acetyl-CoA acetyltransferase | YP_049388 | 2.3.1.9 | express | produce | Erwinia carotovora |
| hbd | Beta-hydroxybutyryl-CoA dehydrogenase | BAD51424 | 1.1.1.157 | express | produce | Butyrivibrio fibrisolvens |

FIG. 10 Cont.

| | | | | | |
|---|---|---|---|---|---|
| CPE0095 | crotonase | BAB79801 | 4.2.1.17 | express | produce | *Clostridium perfringens* |
| bcd | butyryl-CoA dehydrogenase | AAM14583 | not available | express | produce | *Clostridium beijerinckii* |
| ALDH | coenzyme A-acylating aldehyde dehydrogenase | AAT66436 | not available | express | produce | *Clostridium beijerinckii* |
| AdhE | aldehyde-alcohol dehydrogenase | AAN80172 | 1.1.1.1 1.2.1.10 | express | produce | *Escherichia coli* CFT073 |

3C. Fatty Acid Ester Output

| | | | | | |
|---|---|---|---|---|---|
| thioesterase | see chain length control section | | 3.1.2.14 | express | produce | |
| acr1 | Acyl-CoA reductase | YP_047869 | 1.2.1.50 | express | produce | *Acinetobacter sp.* ADP1 |
| yqhD | alcohol dehydrogenase | AP_003562 | 1.1.1.1 | express | produce | *E. Coli K12* |
| AAT | alcohol O-acetyltransferase | AAG13130 | 2.3.1.84 | express | produce | *Fragaria x ananassa* |

4. Export

FIG.10 Cont.

| | | | | | |
|---|---|---|---|---|---|
| Wax ester exporter (FATP family, Fatty Acid (long chain) Transport Protein) | | NP_524723 | NONE | express | export wax | Drosophila melanogaster |
| ABC transporter | putative alkane transporter | AAN73268 | NONE | express | export products | Rhodococcus erythropolis |
| CER5 | wax transporter | At1g51500, AY734542, At3g21090, At1g51460 | NONE | express | export products | Arabidopsis thaliana |
| AtMRP5 | Arabidopsis thaliana multidrug resistance-associated | NP_171908 | NONE | express | export products | Arabidopsis thaliana |
| AmiS2 | ABC transporter AmiS2 | JC5491 | NONE | express | export products | Rhodococcus sp. |
| AtPGP1 | ARABIDOPSIS THALIANA P GLYCOPROTEIN1 | NP_181228 | NONE | express | export products | Arabidopsis thaliana |
| AcrA | putative multidrug-efflux transport protein acrA | CAF23274 | NONE | express | export products | Candidatus Protochlamydia amoebophila UWE25 |

FIG.10 Cont.

| | | | | | | |
|---|---|---|---|---|---|---|
| AcrB | probable multidrug-efflux transport protein, acrB | CAF23275 | NONE | express | export products | *Candidatus Protochlamydia amoebophila UWE25* |
| TolC | Outer membrane protein [Cell envelope biogenesis, | ABD59001 | NONE | express | export products | *Francisella tularensis subsp. novicida* |
| AcrE | transmembrane protein affects septum formation and cell membrane permeability | YP_312213 | NONE | express | export products | *Shigella sonnei Ss046* |
| AcrF | Acriflavine resistance protein F | P24181 | NONE | express | export products | *Escherichia coli* |
| tll1618 | multidrug efflux transporter | NP_682408.1 | | express | export products | *Thermosynechococcus elongatus BP-1]* |
| tll1619 | multidrug efflux transporter | NP_682409.1 | | express | export products | *Thermosynechococcus elongatus BP-1]* |
| tll0139 | multidrug efflux transporter | NP_680930.1 | | express | export products | *Thermosynechococcus elongatus BP-1]* |
| | | | | | | |
| 5. Fermentation | | | | | | |

FIG. 10 Cont.

| replication checkpoint genes | | | | | |
|---|---|---|---|---|---|
| | | | | | increase output efficiency |
| umuD | DNA polymerase V, subunit | YP_310132 | 3.4.21.- | Over-express | increase output efficiency | Shigella sonnei Ss046 |
| umuC | DNA polymerase V, subunit | ABC42261 | 3.4.21.- | Over-express | increase output efficiency | Escherichia coli |
| NADH:NADPH transhydrogenase (alpha and beta subunits) | | P07001 P0AB70 | 1.6.1.1, 1.6.1.2 | express | increase output efficiency | Shigella flexneri |

SEQUENCE LISTING

```
<160> NUMBER OF SEQ ID NOS: 32

<210> SEQ ID NO 1
<211> LENGTH: 498
<212> TYPE: DNA
<213> ORGANISM: Vibrio furnisii

<400> SEQUENCE: 1
gtagatgagc ctaaattttc tagaatttag aaaaacctat tgtagaactg gaagctaaaa     60
ttcaggcgct tcgtgacgtg tctcgtcatg gcggtggaac ttccgtagat cttgaaaaag    120
agatcgaaca gctagaaaag aaaagcctag agcttaaaaa gaaaattttc ggtgatttag    180
gggcatggca agtggcacag atggctcgcc atccacaacg tccttacacc ttagattaca    240
tcaacaacat gtttacggag ttcgatgaac tagccggtga ccgtgcattt gctgacgaca    300
aagcgatcgt gggcggcatg gcccgcttag atggtcgccc tgtgatggtg attggtcatc    360
agaaaggccg tgaaacccgt gaaaaagtaa aacgtaactt tgggatgcca aagccagaag    420
```

```
gttaccgtaa agccctgcgt ttgatggaaa tggctgagcg tttcaacatg ccaatcatta      480
ccttcatcga cacggcgg                                                   498

<210> SEQ ID NO 2
<211> LENGTH: 564
<212> TYPE: DNA
<213> ORGANISM: Vibrio furnisii

<400> SEQUENCE: 2
atgaattcgc tttgtcggca gccgttcgcg cgctgcaagc aaagtaaacc caaacactct       60
gcagctcaat tgagctgtct tattcacaag ataaaagaga agaaacaat ggatattcgt      120 aaaatcaaga agcttatcga attggttgaa gagtcaggca ttgctgagct agaaatttct      180
gaaggtgaag aatcggtacg catcagtcgt cacggtgtcg ccccagttgc acctatccag      240
tatgcagcac ctgcaccaat ggcagcgcca gtagcagcac ctgcagcagc gccagtcgct      300
gaagcaccag cagcagccaa aacgcctgcg ggccacatgg ttctttctcc aatggtgggt      360
acgttctacc gttcaccaag tccagatgca aaatcattca tcgaagtggg tcaaactgtg      420
aaagcgggtg acacattgtg catcgttgaa gcgatgaaaa tgatgaacca aatcgaagca      480
gacaagtctg gtgtagtgac cgagatcctt gttgaagacg tcaggccgt agaattcgac       540 cagccacttg ttgtcatcga ataa                                            564

<210> SEQ ID NO 3
<211> LENGTH: 1344
<212> TYPE: DNA
<213> ORGANISM: Vibrio furnisii

<400> SEQUENCE: 3
atgctagata agttagtcat cgcgaaccga ggcgaaattg cgcttcgtat tcttcgtgca       60
tgtaaagagt tgggcatcaa aactgttgcc gttcactcca cagcagaccg cgatctaaaa      120
cacgtcctgc tggcggatga aaccgtatgt atcggccctg caaaaggcat cgatagctac      180
ttgaacattc cacgcatcat ttcagccgct gaagtgaccg gcgcagtggc catccacccg      240 ggttacgggct tcctgtctga aaatgcggac tttgctgaac aagttgagcg cagcggcttt      300
atcttcgtgg gtccaaaagc cgacaccatc cgcctgatgg gcgataaagt gtcagccatc      360
accgcgatga agaaagcagg cgttccttgt gtaccgggtt ctgacggtcc tctggacaac      420
gatgaagtga aaaaccgtgc acacgcgaaa cgcattggtt acccagtgat catcaaagcc      480
tctggtggcg gcgcggtcg cggtatgcgt gtggttcgca gcgaagcgga actggtcaat      540
gccatcagca tgacccgtgc agaagcgaaa gcggcgttca caacgacat ggtttacatg       600 gagaaatacc tcgaaaaccc acgtcacgtt gaagtccaag ttctggccga tggtcagggc      660
agcgcgatcc acttgggtga acgcgactgt tccatgcagc gtcgtcacca gaaagtagtg      720
gaagaagcgc cagcaccagg cattactgaa gagatgcgta agtacatcgg tgaacgctgt      780
acccgtgcgt gtatcgaaat cggttaccgc ggcgcaggta cgtttgagtt cctgtacgaa      840
aacggcgaat tctacttcat cgaaatgaac acacgtattc aggttgaaca cccagtgact      900
gaaatggtca caggcgttga cttgatcaaa gaacagctgc gcatcgcagc aggccaaccg      960
ctgtcgttca cacaagacga catcaaaatt cgtggccatg cgatggaatg ccgtatcaac     1020
gcggaagacc cagaacgctt cctacccttgc ccaggcaaga tcaccgtttt ccactcacca     1080
ggtggcatgg gcgtgcgttg ggaatcacac atctactcag cctacaccgt accggcgtac     1140
tacgactcga tgatcggcaa actgatcacc tttggtgaga accgtgacgt cgcgattgca     1200
```

| | |
|---|---:|
| cggatgcgta acgcgctcga tgagatgatt gtggaaggta tcaaaaccaa cattccactg | 1260 |
| cagcaagtaa tcatgaaaga tgagaacttc caacacggtg gcaccaacat ccactatctg | 1320 |
| gagaaaaagc tggggctgca ataa | 1344 |

<210> SEQ ID NO 4
<211> LENGTH: 927
<212> TYPE: DNA
<213> ORGANISM: Vibrio furnisii

<400> SEQUENCE: 4

| | |
|---|---:|
| atgagctggc ttgagaagat tttagaaaaa agcaacatcg aagttcacg taaagcgtct | 60 |
| atccctgaag gggtttggac caaatgtaca tcgtgtgaac aggtgctta ttacgctgaa | 120 |
| ctagagcgca atcttgaagt ttgtccgaag tgtaatcatc acatgcgtat gaaggcgcgc | 180 |
| cgtcgtcttg aaacgttctt ggacgaagca aaccgttacg aaatcgcgga cgaactcgaa | 240 |
| ccgcaagata aactgaaatt taagactcc aaacgttaca aagagcgtct tgcgactgcg | 300 |
| cagaagagca gtggcgaaaa agatgcgctg attgtgatga aggcgagtt gatgacgatt | 360 |
| ccagtcgtgg cgtgtgcgtt tgaattctcg ttcatgggcg gttcaatggg gtcggttgtc | 420 |
| ggtgcgcgtt tcgtgcgtgc agttgaagcg gcgattgaag cgaactgtgg tctggtctgt | 480 |
| ttctctgcca gtggtggcgc acgtatgcaa gaagcgctga tgtcgctgat gcagatggcc | 540 |
| aaaaccagtg cagcgctcga gcgtctaacg gcgaaaggtc tcccgtttat ctccgtgatg | 600 |
| acagacccaa ccatgggtgg ggtgtctgcg agtctggcaa tgctgggcga catcaacatc | 660 |
| ggtgagccga agcactgat cggtttcgcg ggtcgtcgcg tgatcgagca gaccgtgcgc | 720 |
| gaagagctgc cggaaggttt ccaacgcagc gaattcctgc tggagcacgg tgcgattgat | 780 |
| atgatcgttg accgtcgtga aatgcgtcag cgtgtggctg gcctgctggc gaaaatgaca | 840 |
| cgtcaggagt cgccgctggt ggtttctgtg aacgatgcgc caaatgaagc cgcatattct | 900 |
| gtaccagaag cgaacaaaaa agggtaa | 927 |

<210> SEQ ID NO 5
<211> LENGTH: 2445
<212> TYPE: DNA
<213> ORGANISM: Vibrio furnisii

<400> SEQUENCE: 5

| | |
|---|---:|
| atggacatct tgctctcaat cttagggttc gtggtcgtgt taagcggctg cctgtaccac | 60 |
| agaacctcat taatgactgc cttagccgca ctgaccgtga ccatgttggt cctgtcgttg | 120 |
| tttggcccag tgggtatcat cagctggggcg ctgtacttag ccgctatcgc ggtattggca | 180 |
| gtcccgtcaa tccgtcaaag tctcatcagc ggtaagacac taaaggtatt caaaaaagta | 240 |
| ctgcctgcga tgtcgcagac agaaaaagaa gcgcttgatg ctggcaccgt gtggtgggaa | 300 |
| gccgaactgt tcaaaggcaa accggactgg caacagctga ccatatcaa agcgcccaca | 360 |
| ctttctgccg aagaacaggc gttcctcgat ggcccagtga acgaagtgtg cgccatggtg | 420 |
| aacgactatc aggtgactca cgaattggcg gatttgcctc cggaagtgtg gcaatacctg | 480 |
| aaagaccaca aatttttcgc catgatcatt aagaagcagt acggcggctt ggaattttcc | 540 |
| gcgtacgcgc aatcgctggt gctacaaaag ctgacgggcg tatcgggcgt gctctcttcc | 600 |
| accgtcggcg tgccgaactc tctcggcccg ggcgaactgc tgcaacatta cggcaccgac | 660 |
| gatcagaaag attactacct ccctcgtttg gcggaaggca aagagattcc atgtttcgcg | 720 |

```
ctgaccagcc cagaagcggg ctctgatgcg ggctcgattc cggattacgg catcgtgtgc      780
aaagacgaat gggaaggcaa agaagtgctg ggcatgcgcc tgacatggaa caaacgctac      840
atcacgctgg cgccagttgc gacggttctt ggtttggcct ttaaactgcg cgaccctgac      900
gggctattgg gcgaccaaaa agagattggc atcacgtgtg ctttgatccc gacacacctc      960
aaaggggtgg aaatcggcaa tcgtcacttc ccattgaacg tgccgttcca aaatggcccg     1020
acgcgcgcga acgatctatt tgtgccgctg gacttcatca tcggtggccc atcgatggcc     1080
ggccaaggtt ggcgcatgct ggtggaatgt ttatcagtgg gtcgcggtat tacgctgcca     1140
tcgaactcaa ctggcggcat caaagcggcg gcaatggcaa cgggcgctta tgcgcgcatt     1200
cgtcgtcagt tcaagcaacc cattggtcac atggaaggga ttgaagaacc tttggcgcgc     1260
cttgcaggga acgcttacgt gatggatgca gcgagcaacc tcactgtcgc ggggattgat     1320
gccggcgaaa aaccatcggt tatttctgcg attgtgaagt atcactgtac ccaccgcggc     1380
caacgctcaa tcatcgatgc aatggacatc gtcggcggca aaggcatctg tttgggccca     1440
tcgaacttcc ttgcgcgagg ttaccaaggt tcccctatcg cgatcaccgt ggaaggcgcc     1500
aacattctga cccgctccat gatcatcttt ggtcagggtg ctattcgctg ccatccgtac     1560
gttttgaaag agatggaagc agcgtattca gacagcgcca atgcggtcga acaatttgac     1620
gccgcgctgg ctggccatgt cagctttacc atgagtaact tggtgcgctg catctggttt     1680
ggtctgaccg acgggttagg ctctgccgca ccaaccaaag atgccaccaa acgttactat     1740
cagcaactca accgttacag tgcaaacctt gccctgctgg ccgatatttc catggccgta     1800
ctgggtggct ccctgaaacg taaagagcgc ctgtccgcgc gtttgggtga tattttaagc     1860
caactttatc tcagctcagc aacgctgaag cgctttgaga atgatggtcg cccagcagaa     1920
gatttggcct tggtacactg ggggctgcaa gacagcttga aacagaccga agtggcgatt     1980
gatgagttct tggcgaactt cccgaacaag gtgatcggca aagccctgcg tgtcttgatc     2040
atgccatttg gccgcgtgcg caaagcacca acgacaagc tcgacagcaa agtggcgcag     2100
atcattcaaa cgccaagtgc gacccgctca cgcatcggtc gtcatcagta cctcgaaccg     2160
actgcacata acgcggtcgg caagattgaa ctggcgttga atgtgattct tcaagcagaa     2220
ccggtgttcg acaaggtatg caaagcgctg aacgaacgtc gcccattcac gcaattggat     2280
caagtggcac aatgtggcct tgagcaaaag ctgatcaccg agcaagaagc cgaactgctg     2340
atcgaagccg agcaacaccg cttatacacc atcaatgtgg atgactttgc gccgcaggag     2400
ttagcagcaa aaaagtcaca acccaagctg gtcgaggtcg cgtga                    2445

<210> SEQ ID NO 6
<211> LENGTH: 2424
<212> TYPE: DNA
<213> ORGANISM: Vibrio furnisii

<400> SEQUENCE: 6
atgtcttctg acactcatt tcgcgttcc ttgttgaaat taccactgtc tgttctggta        60
aaaggtacgg tcattccatc caatccgatc gatgatctcg agattgatat taacaagccg      120
atcgtctatg cactaccctt cgctccaat gtcgacctgt tgacgctgca aacgcatgcg       180
ttacaagccg gcctgccgga tccgttagaa ccgctgacca ttcatagtca cacgctgaaa      240
cgttacgtgt tcatctcgtc gcgccccacg ctgctgcaag atgacaatca ggtgccgacc      300
gattctatcg ccacattcag cgaaatgctc agcctgcatc aagaagattc ggagttggat      360
gtgcaggtca ttcctgccac cgtcctgtgg ggacgcaaac cgggcaaaga aggtcgggaa      420
```

```
cgtccatatt tgcaagcctt gaatggcccg caaaaagcca agcggtctt tgccgccgga      480 cgggactgtt tggtgcgctt tagccccgtg gtctcgctgc gttatatggc cgactcgcac      540
ggcaccgatg cctcgattgc ccacaagctg gcacgtgtgg cgcgcattca cttctcacgt      600
cagaagctgg cggcgtctgg gccgaacctg ccacaacgcc accagttgtt ccaacgcttg      660
atgaattccc cagcgatcga aaaagcgatt gctgatgaag cggccgcgaa gaacatctcg      720
ctggagaaag cgcgtaaaga agcgcacgac atgcttgatg aaatcgccgc agatttctct      780
tactcgttgg tgcgcaaagg cgatcgcatt ctgggttggt tatggaaccg catctatcaa      840
ggcttgaaca tcaataacgc cgcgacggtg cgccgcttgg cacaagatgg tcacgagatt      900
gtgtatgtgc cctgtcaccg cagccacatg gattacctgt tgctgtcata cgtgttgtat      960
cacgaaggca tggtgccccc gcacattgca gcaggtatta acctcaactt cttcccggcc     1020
ggaccgattt tccgccgtgg tggcgcattc tttattcgtc gcagctttaa aggcaacaaa     1080
ctctattcaa ccatcttccg cgagtatctg cagagctgtt tgccaaagg ctactcggtg     1140 gagtacttca gtgaaggggg ccgctcacgc acaggtcgcc tgctgcaagc caaaaccggc     1200
atgctggcga tgaccattca agccatgttg cgcggtctca accgcccggt cacactggtg     1260
cccgtgtaca tcggctatga acatgtgatg gaagtgggta cttacgccaa agagctgcgc     1320
ggtaaacgca agagaaaga gaatgccagc ctagtgctgc gcaccattcg taaactgcgc     1380
aacttcggtc aaggctacgt gaactttggt gagccgattc cattgaacca gttcttgaat     1440
gagcaagtgc ccgagtggac acaagacatc gatgccatgg gcgccagcaa accccagtgg     1500
atgacaccgg tggtgaacaa gctcgcgacg aagatgatga cgcacattaa cgatgcagcg     1560
gccgccaatg ccatgaccct atgtgcgacg gcgcttttgg catcgcgtca gcgcgcgctg     1620
gcccgtgaca atctggtgaa gcagatcgat tgctacctgc aactgctgcg caacgtgccc     1680
tattccaaca cctataccgt gccaagcgac agcgcggaaa gtttggtgca gcacgccgaa     1740
tcactggata gtttgtggt ggaaaccgac accatgggcg acatcatttc gctcgatcgc     1800
aatcagtcga ttctgatgac ctactaccgc aacaacatca ttcacctgct ggcgttgcca     1860
tcactgattg cgcagatgct gatccgtcag caacaaatgc cggtgaaaca gattcagacc     1920
tgtgttgcga aggtgtaccc attcctcaaa caagagctgt tcctcagcca tgatgaaacg     1980
caactcgatg aggtggtgat gcattatctc gctgagctgc aacgccaaca actggtgacg     2040
ctggacgatg gcattgccac catcaaccaa gcgcagacgc aggtgctgat gcttctgggt     2100
cgcaccatct ctgagacgct gcaacgctac gcgatcacgc tcaacctgtt ggtggctaac     2160
cctgagctgg gcaaatccga tctggaaagc aagagccaag aaattgcgca gcgtctgggt     2220
cgactgcacg gcatcaacgc ccccgagttt ttcgacaaag gcgtgttctc atcgatgttt     2280
gtcacgctca acagcaagg ttacctcgac agcgatggca actgccacct cgaccagacc     2340
aagcacttct cgcgcatgct ctacaccatg ctttaccctg aagtgcgcct gactattcag     2400
gaaagtatct gtcaggtgga ataa                                            2424

<210> SEQ ID NO 7
<211> LENGTH: 2661
<212> TYPE: DNA
<213> ORGANISM: Vibrio furnisii

<400> SEQUENCE: 7
atgtctgaca tgaagcatga cgtagatgca ctggaaactc aggagtggtt agccgcactt       60
```

```
gagtcagttg tacgtgaaga aggcgtagag cgtgcccagt atctactaga agaagtactg    120
gaaaaagcac gtctagacgg cgttgatatg ccaactggta ttacaactaa ctacatcaac    180
acgattcctg cggcgcaaga accggcatac ccaggcgaca cgaccattga acgtcgtatt    240
cgttcgatca ttcgttggaa cgcgatcatg atcgttctgc gtgcatcgaa gaaagacctg    300
gatctgggcg gccacatggc atcattccag tcttcagctg cgttctatga acatgtttc    360 aaccacttct tccgtgcacc aaacgagaag gacggtggtg acctggttta ctaccaaggt    420
catatttctc cagggattta cgcgcgtgca ttcgttgaag gccgcctgac agaagaacaa    480
ctggataact tccgtcaaga agtggatggc aaaggtattc cttcctaccc acacccgaaa    540
ctgatgcctg aattctggca attcccaact gtatcgatgg gtctgggtcc tatcgcatcg    600
atctaccaag ctcgcttcct gaaatacctg gaaggccgtg gcatgaaaga cactgctgag    660
cagcgcgttt acgcgttctt gggcgacggt gagatggatg agccagaatc acgtggtgcc    720
atttctttcg cggcgcgtga gaaactggac aacctgtgct tcctgatcaa ctgtaacctg    780
caacgtctgg atgcccagt aatgggtaac ggcaagatca tccaagagct agaaggcctg    840
ttcaaaggcg ctggctggaa cgtggtgaaa gtgatctggg gtaacaactg ggattctctg    900
ctggcaaaag acacttcagg taaattgctg caactgatga acgaaaccat cgacggcgac    960
taccaaacgt tcaaagcgaa agatggcgcg tacgttcgtg agcatttctt cggtaaatac   1020
ccagagacag cagcgctggt tgctgacatg actgacgacg aagtgttcgc cctgaaacgt   1080
ggtggtcacg agtcttctaa actgtacgca gcgttcaaga acgcacaaga caccaaaggc   1140
cgtccaaccg ttatcctcgc gaagactgta aaaggttacg gcatgggtga tgcggctcaa   1200
ggtaagaaca ttgcacacca agtgaagaag atggacatga cgcacgtgat cgcgatgcgt   1260
aaccgtctgg gtctgcaaga cataatttct gatgaagaag tgaacaacct gccttacctg   1320
aaactggaag aaggttcaaa agaattcgaa tacctgcacg ctcgtcgtaa agcgctgcac   1380
ggttacacgc cacagcgtct gcctaagttc acacaagagc ttgtgattcc tgaactggaa   1440
gagttcaaac cgcttctgga agaacagaaa cgtgaaatct cttcaaccat ggcttacgtg   1500
cgtgcactga acattctgtt gaaagacaaa aatattggta agaacatcgt tcctatcatt   1560
gctgacgaag cacgtacttt cggtatggaa ggtctgttcc gtcaaatcgg tatctacaac   1620
ccacacggcc agacgtacac gcctgaagac cgtggcgtgg tgtcttacta caaagaagac   1680
actgcaggtc aggtactgca agaagggatc aacgaactgg gtgcaatgtc atcttgggtt   1740
gcggctgcga catcttacag caccaacaac ctgccaatga ttccgttcta catctactac   1800
tcaatgttcg gtttccaacg cgttggcgac atggcatgga tggcaggtga ccaacaagcg   1860
cgtggtttcc tactgggcgc aacggctggc cgtacaaccc tgaacggtga aggcctgcag   1920
cacgaagatg gtcactcaca cattcaagcc gcgacaattc gaactgtat ctcttacgac   1980 ccaacattcg cttacgaagt tgcggtgatc atgcaagacg gtatccgtcg tatgtatggc   2040
gatcaagaga acgtgttcta ctacatgacg ctgatgaacg agaactacgc tcacccagcg   2100
atgccagaag gcgcagaaga aggtatccgt aaaggtatct acaaactgga aacgctgtct   2160
ggttctaaag gtaaggttca actgatgagc tcaggtacta tcatgaatga agtacgcaaa   2220
gcggcagtga tcctgagcga agaatacggc atcgcgtctg atgtttactc tgtaacctca   2280
ttcaacgaac tggctcgtga tggtcagaac gtcgagcgtt acaacatgct tcacccagaa   2340
gccgaagcgc aagtacctta catcgcttca gtgatgggaa ctgaaccagc aatcgctgca   2400
accgactaca tgaagaacta cgctgaccaa gttcgcgcgt tcattcctgc agagtcttac   2460
```

```
aaagtgctgg gtactgacgg cttcggtcgt tcagacagcc gtgagaacct acgtcgtcac   2520
ttcgaagtga acgcaggcta cgtcgttgtt gctgcgctaa acgaactagc gaaacgtggt   2580
gaagttgaga atctgtggt ggcggaagct atcaagaaat tcgacatcga cactgaaaaa    2640
actaacccgc tatacgctta a                                              2661

<210> SEQ ID NO 8
<211> LENGTH: 1893
<212> TYPE: DNA
<213> ORGANISM: Vibrio furnisii

<400> SEQUENCE: 8
atggctatcg aaatttacgt accagatatc ggtgcagatg aggttgaagt gactgagatt     60
cttgtcagcg taggcgacaa ggttgaagaa gaacaatctc tgattactgt tgaaggcgac    120
aaagcttcta tggaagttcc tgcgtctcag gccggtattg tcaaagaaat caaagttgtg    180
actggtgata aagtcacaac tggctcactg atcatggtgt ttgaagcgga aggtgcagca    240
gcggctgcac cagcacctgc ggcggaagca gcaccagttg cggcagcacc agcagccgtt    300
gaactgaaag aagttaacgt accggacatc ggcggtgacg aagttgaagt gactgaaatc    360
atggttgcgg tgggtgacac cgtgtctgaa gagcagtcgc tgatcaccgt tgaaggcgac    420
aaagcgtcaa tggaagtgcc tgcgccattc gcgggtaccg tgaaagagat caagatcgca    480
tcgggtgaca aagtgaccac aggctcactg atcatggtct tcgaagtggc cggttctggt    540
gcgccagcag cggcagcgcc agctcaggca gcggctccag cagcagcgcc agcggtagca    600
gcagataaag aagttaacgt gccagatatc ggcggcgatg aagttgaagt gactgaaatc    660
atggttgcag ttggcgacat ggtgagcgaa gagcaatctc tgatcactgt ggaaggcgac    720
aaagcgtcga tggaagttcc tgcaccattc gcgggtaaag tgaaagcgat caagtcgcg     780 gctggcgaca aagtgtcgac tggctcactg atcatggtgt ttgaagtggc aggcgcagcg    840
ccggcagctg tttcagcacc agctcaagcc gcagcacctg cagcagcggc accgaaagct    900
gaagcgccag cggcagcagc acctgcagcg gcaaccggcg acttccaaga gaacaatgaa    960
tacgcacacg cgtcgccagt ggttcgtcgc ttagcgcgtg aattcggtgt gaacctgtct   1020
aaagtgaaag gttcaggtcg taagagccgc attctgaaag aagatgttca gaactacgtg   1080
aaagaagcgc tgaaacgcct agaatcaggc gcagcatcag ccgcatctgg caaaggcgac   1140
ggcgcagcac ttggcctgct accttggcca aaagtggact tcagcaagtt cggtgacact   1200
gaaattcagc cactgtctcg cattaagaag atctctggcg cgaacctgca ccgtaactgg   1260
gtgatgatcc cgcacgtgac ccagtgggat aacgcagaca tcacagaact agaagctttc   1320
cgtaaagaac agaacgcgat cgaagcgaag aaagacactg gcatgaagat cacgccactg   1380
gtgtttatca tgaaagcggc tgcgaaagcg ctggaagcat tccctgcgtt caactcgtct   1440
ctgtctgaag atggtgaaag cctgattctg aagaaatacg tgaacatcgg tatcgcggtt   1500
gataccccaa acggtctggt tgttcctgtg ttcaaagacg tgaacaagaa aggcatttac   1560
gagctgtctg aagagttggc agtcgtatcg aagaaagcac gtgcaggtaa actgacggcg   1620
tctgacatgc aaggcggctg tttcaccatc tctagtctgg gtggtatcgg cggtacagca   1680
ttcacaccaa tcgtgaatgc accagaagta ggtattctgg gtgtgtctaa gtctgaaatg   1740
aagccagtgt ggaacggcaa agaatttgcg ccacgtctgc aactgcctct gtctctgtca   1800
tacgaccacc gtgtgatcga tggcgcggaa ggtgcacgct tcatcactta cttgaacggt   1860
```

```
tgcctgagcg acattcgtcg tctggttctg taa                          1893
```

<210> SEQ ID NO 9
<211> LENGTH: 951
<212> TYPE: DNA
<213> ORGANISM: Vibrio furnisii

<400> SEQUENCE: 9

```
atgtatagca aaattttagg tacaggcagc tacctgccat ctcaggtgcg tactaacgcg    60
gatttagaga aaatggtaga tacaagtgat gagtggattg tcacgcgtac tggtattcgc   120
gagcgtcgta ttgccgcaga taatgaaacc gttgccgata tgggctttta cgcggcgcaa   180
aacgctattg agatggcggg cattgataaa aacgacatcg atttaatcat ccttgccacg   240
accagtagca gtcacacgtt cccttcgtct gcctgtcagg tgcaagcgaa actgggcatt   300
aaaggttgcc cagcgtttga ccttgcggca gcgtgttctg gttttatcta cggattgtca   360
gtcgcggatc aacacatcaa atcgggcatg tgtaaaaacg tgctggtgat tggtgccgat   420
gcgttgtcaa aaacgtgtga cccaaccgat cgctcaacca ttatcctgtt tggtgatggt   480
gcgggtgcgg ttgtggttgg tgccagtgaa gaacctggca ttttgtcgac tcatgtttac   540
gctgatggtc aattcggcga cctgctcagc ctggaagtac agagcgtgg cggtgatgtg   600
gacaaatggc tatatatggc cggcaacgaa gtgttcaaag tggcggtgac gcagctttca   660
aaactggtca agacacgct ggcagccaac aatatgcaca agtctgaact agactggttg   720
gtaccgcatc aagcgaacta tcgcattatt tctgcgacgg cgaaaaaatt gtcgatgtcg   780
ctggatcaag tggtgatcac gttggaccgt catgggaaca cgtctgctgc aacggtgccg   840
acggcactgg acgaagcggt acgtgatggc cggatcaaac ggggtcagac gctacttta   900
gaagcctttg tggtggttt cacctggggt tctgcgttag tgaagttcta a             951
```

<210> SEQ ID NO 10
<211> LENGTH: 924
<212> TYPE: DNA
<213> ORGANISM: Vibrio furnisii

<400> SEQUENCE: 10

```
atgagcaagt ttgctatcgt atttccaggt caaggttctc aagcggttgg tatgcttgcc    60
gagcttggcg aacagtatga cgtagttaaa caaactttcg cagaagcgtc tgacgcactg   120
ggttacgacc tatgggcatt ggttcagaac ggtcctgttg aagatctcaa ccagactttc   180
cgtacgcaac ctgcactgct ggcgtcttct gtggcgattt ggcgtgtatg caagcgctg   240
ggtcttgagc agccagaagt gctggcaggc acagccttg gtgaatactc tgcactggtt   300
tgtgccggtg tgattgattt taaagccgcg atcaaattgg tcgaactgcg tggtcaactg   360
atgcaagaag cagtacctgc aggaaccggc gcaatgtacg cgatcatcgg tttggatgat   420
gcggcgattg ccaaagcgtg tgaagacgct gcgcaaggcg acgtggtgtc tccggtgaac   480
ttcaactcac caggccaagt ggtcattgcc ggtcagaaag atgcggtaga acgcgcgggc   540
gcactgtgta agaagcggg cgcgaaacgt gcactgccac tgccggtgtc agtgccttca   600
cactgcgcgc tgatgaaacc tgcagcagaa aaactggctg tggcgctaga agcgcttgag   660
ttcaacgcgc cgcaaatccc agtgattaac aacgtggacg ttgcgacaga aacggatcca   720
gcgaaaatca aagatgcgtt ggttcgtcaa ctacacagcc agtccgctg acagaaggc    780
gtggagaaga tggcagcaca aggcattgaa aaactaattg aagttggccc aggcaaagta   840
ctgactggtt tgactaaacg tattgtgaaa acgcttgatg cagcagcagt gaacgacatc   900
```

```
gcttcactgg aagccgttaa gtaa                                            924
```

<210> SEQ ID NO 11
<211> LENGTH: 747
<212> TYPE: DNA
<213> ORGANISM: Vibrio furnisii

<400> SEQUENCE: 11

```
atgagtaatt tcatgaacct ggaaggcaaa attgtcctgg ttactggcgc aagccgtggt     60
atcggtaaag caatcgcgga actattggtt gaacgtggtg ccacagtgat tggtacagcg    120
accagcgaaa gcggcgcaga tgcgatcagt gcgtacctag cgacaacggc aaaggtctg    180
gcgttgaatg tgacagatgt agcgtctatc gaatccgtgc tgaaaagcat taacgatgaa    240
ttcggcggtt ttgatattct ggtgaacaac gcgggtatca cgcgtgacaa cctgctgatg    300
cgtatgaaag atgacgagtg gaccgatatt ctggatacca acttgacgtc gatcttccgt    360
ctgtctaaag ctgtacttcg tggcatgatg aaaaaacgcc aaggccgtat cattaatgtc    420
ggttctgttg tcggtacaat gggtaacgcg ggtcaaacaa actacgcagc cgcaaaagcg    480
ggcgtaatcg gctttacgaa gtcaatggca cgtgaagttg catcccgtgg cgtgaccgtg    540
aacacagttg caccaggttt catcgaaacg gatatgacaa aagcgctgaa tgacgaccaa    600
cgtgctgcta cacttgcaca agtgccagca ggtcgtctgg gtgatccacg tgaaatcgca    660
tccgcggttg cattcttggc atctccagaa gcagcgtaca ttaccggtga aactctgcac    720
gttaacggcg gaatgtacat ggtttaa                                         747
```

<210> SEQ ID NO 12
<211> LENGTH: 525
<212> TYPE: DNA
<213> ORGANISM: Vibrio furnisii

<400> SEQUENCE: 12

```
gaagtgaacg gaacttgttc ggtaaaatgt tgacttcgtc caaaacttgt caatgaaatg     60
cgcaagattt gtgcatgata tatgtcaaaa atggtgtgaa tttcggttaa aatcgccaaa    120
tttgtggttt gaccagcaag gtccccttg caactttcac tagtttgaat aaactacgga    180
atcatcgcat taggcgaaat ctgtaaagga aagaaaaaa tgagcaacat cgaagaacgc    240
gtaaagaaaa tcatcgttga acagctaggc gtagacgaag cagaagtgaa aaacgaagct    300
tctttcgttg aagacctagg tgcggattct ctagacactg ttgagcttgt tatggctctg    360
gaagaagaat tcgacactga gattcctgat gaagaagcag agaaaatcac tactgttcaa    420
gctgcgatcg attacgtaaa cagcgctcag taatgtctct ccccaggcgg ccctctggcc    480
gcctgagttt ttctcactca tctataatct ctcatagaat tttca                     525
```

<210> SEQ ID NO 13
<211> LENGTH: 1251
<212> TYPE: DNA
<213> ORGANISM: Vibrio furnisii

<400> SEQUENCE: 13

```
atgatcgtgt ccaagcgtcg tgtcgttgtc actggcatgg gtatgttgtc accggtaggc     60
aacactgtag aatcttcttg gaaagccctg ctagctggtc aaagtggtat cgtgaatatc    120
gaacactttg atacaacaaa tttctcaact cgtttcgcag gtctggtaaa agatttcaac    180
tgcgaagagt acatgtctaa aaaagatgcc cgtaaaatgg atttatttat ccagtacggt    240
```

```
attgctgcgg gcatccaagc gctagacgat tctggtctgg tgatcactga agaaaacgcg    300
ccacgcgtcg gtgttgcaat cggctcgggc atcggtggtc ttgatttgat cgaaaaaggt    360
catcaagcgc ttatggagaa aggtccacgt aaagtgagcc cattcttcgt cccttcaacc    420
atcgtgaaca tggttgccgg taacttatct atcatgcgtg gtcttcgtgg tcctaacatc    480
gcgatttcaa ctgcatgtac cacaggttta cataacatcg ccacgcggc gcgtatgatt     540 gcatacggcg atgcggaagc gatggttgct ggtggtagtg aaaaagcgtc taccctctg     600 ggtatggctg gcttcggtgc cgctaaagcg ctgtctacac gcaacgatga acctgcaaaa    660
gcttctcgcc cttgggacaa agaccgtgac ggttttgttc tgggtgacgg cgcaggcgtg    720
atggttctgg aaggatacga acacgcaaaa gcgcgtggcg cgaaaatcta cgcagaaatc    780
gtaggcttcg gtatgtccgg tgacgcgtac cacatgactt cgccaagcga agatggttca    840
ggtggcgcgc tggctatgga agcggcgatg cgtgatgcag cactagcggg tacacaaatc    900
ggctacgtga acgcgcacgg tacgtcaaca ccagcaggtg acgtagcgga agtgaaaggt    960
atcaaacgtg cacttggcga agacggtgcg aaacaagtac tgatctcttc aaccaaatcg   1020
atgaccggtc acctactggg tgctgcaggc tcggtagaag ccatcattac cgtgatgtct   1080
ctggttgacc aaatcgttcc gccaaccatc aacctgata atccagaaga aggtttgggc    1140
gtggatttgg ttccgcacac agcacgtaaa gtggaaggca tggaatacgc gatgtgtaac   1200
tcgtttggct ttggtggcac aaacggttca ctgatcttca agcgcgtata a             1251
```

<210> SEQ ID NO 14
<211> LENGTH: 1035
<212> TYPE: DNA
<213> ORGANISM: Vibrio furnisii

<400> SEQUENCE: 14

```
atgactgatt cacacacaaa caatgcttac ggtaaagcga tcgccatgac cgtcattggc     60
gcgggttcgt acggcacatc tctggccatt tctttggctc gcaacggcgc caatgttgtc    120
ctgtggggac acgatccggt ccacatggcg cgtttggaag cggaacgtgc taaccacgaa    180
ttcctccctg catcgatttt ccaccgtcg ctgatcattg aatccgattt gcaaaaagcg     240
gtgcaagcga gccgcgatct gctggtggtg gtgccaagcc atgtgtttgc gattgtgctc    300
aacagcctgc aaccttactt gcgagaagat acccgtatct gctgggcaac caagggttg     360 gaaccggaca caggacgttt gctgcaagat gtggcgcatg acgtgctggg tgaatcccat    420
ccattggcgg tgctgtctgg cccgacgttt gcgaaagagc tggcgatggg tatgcccact    480
gcgatttcag tggcatcgcc tgacgcgcag tttgtcgccg atctgcagga aaagattcac    540
tgcagcaaaa ccttccgtgt ttatgccaac agcgatttca tcggcatgca actgggggc     600 gctgtgaaga acgtgattgc cattggtgcg gggatgtcgg atggcatcgg ctttggtgcc    660
aacgctcgta cggcgctgat tacccgtggt ttggcggaaa tgacccgtct gggcgcggcg    720
ctgggcgcgc agccggaaac cttcatggc atggcggggc tgggtgatt ggtgctgacg     780 tgtaccgata accaatcgcg caaccgtcgt tttggtttgg ccttgggcca aggcaaagat    840
gtcgatacgg cgcaacaaga tatcggtcaa gtggtgaag ggtatcggaa caccaaagag     900
gtgtggctac tggcgcaacg catgggcgtg agatgccaa tagttgaaca aatttatcaa     960
gtattgtatc aaggaaagga cgcccgcatg gcagcacaag atttgctggc gcgcgataaa   1020
aaagcagaac gataa                                                     1035
```

<210> SEQ ID NO 15
<211> LENGTH: 855
<212> TYPE: DNA
<213> ORGANISM: Vibrio furnisii

<400> SEQUENCE: 15

| | | | | | |
|---|---|---|---|---|---|
| gtggtgtgtg | cgtttgtgaa | cgacgatttg | agtgcgaccg | tgttggaaga | actgtatcaa | 60 |
| gggggcactc | gcctgatcgc | catgcgctgc | gcgggctttg | ataaagtgga | tttagacgcc | 120 |
| gcaaaacgca | ttggcatgca | ggtggttcgc | gtacctgcgt | attcaccaga | agcggtggca | 180 |
| gagcacgcgg | tcgggttgat | gatgtgtctg | aaccgccgtt | accacaaagc | gtatcagcgc | 240 |
| acacgtgagg | ccaacttctc | gttggaaggc | ttggtgggct | taacttcta | tggcaaaacc | 300 |
| gtgggtgtga | ttggttcagg | caagattggc | attgcagcga | tgcgtatcct | caaaggcctt | 360 |
| ggcatgaaca | ttctctgctt | tgacccgtat | gaaaacccat | tggccattga | aatcggcgcg | 420 |
| aaatacgttc | aattgccgga | gctgtatgca | aacagcgaca | tcattacgct | gcactgcccg | 480 |
| atgaccaaag | aaaactacca | cctgctggat | gagcaagcgt | tcgctcaaat | gaaggatggg | 540 |
| gtgatgatca | tcaataccag | ccgtggcgaa | ttgcttgatt | cagtcgcagc | cattgaagcg | 600 |
| ctcaaacgtg | gccgtattgg | cgcgctgggc | ttagacgtat | acgacaacga | aaagatctg | 660 |
| ttcttccaag | acaagtcgaa | cgatgtgatt | gtagatgacg | tgttccgccg | cctgtccgcc | 720 |
| tgccataacg | tgctgtttac | cggccatcag | gcgttttga | cagaagatgc | cctgcacaat | 780 |
| atcgcgcaaa | ccacgcttaa | caacgtgctg | gcgtttgagc | aaggcaccaa | atctggaaac | 840 |
| gaattagtta | actaa | | | | | 855 |

<210> SEQ ID NO 16
<211> LENGTH: 177
<212> TYPE: PRT
<213> ORGANISM: Vibrio furnisii
<220> FEATURE:
<221> NAME/KEY: MOD_RES
<222> LOCATION: (2)..(2)
<223> OTHER INFORMATION: Any naturally occurring amino acid

<400> SEQUENCE: 16

Phe Xaa Asn Leu Glu Lys Pro Ile Val Glu Leu Glu Ala Lys Ile Gln
1               5                   10                  15

Ala Leu Arg Asp Val Ser Arg His Gly Gly Gly Thr Ser Val Asp Leu
            20                  25                  30

Glu Lys Glu Ile Glu Gln Leu Glu Lys Lys Ser Leu Glu Leu Lys Lys
        35                  40                  45

Lys Ile Phe Gly Asp Leu Gly Ala Trp Gln Val Ala Gln Met Ala Arg
    50                  55                  60

His Pro Gln Arg Pro Tyr Thr Leu Asp Tyr Ile Asn Asn Met Phe Thr
65                  70                  75                  80

Glu Phe Asp Glu Leu Ala Gly Asp Arg Ala Phe Ala Asp Lys Ala
                85                  90                  95

Ile Val Gly Gly Met Ala Arg Leu Asp Gly Arg Pro Val Met Val Ile
            100                 105                 110

Gly His Gln Lys Gly Arg Glu Thr Arg Glu Lys Val Lys Arg Asn Phe
        115                 120                 125

Gly Met Pro Lys Pro Glu Gly Tyr Arg Lys Ala Leu Arg Leu Met Glu
    130                 135                 140

Met Ala Glu Arg Phe Asn Met Pro Ile Ile Thr Phe Ile Asp Thr Ala
145                 150                 155                 160

```
Gly Ala Tyr Pro Gly Val Gly Ala Glu Glu Arg Gly Gln Ser Glu Ala
                165                 170                 175
Ile

<210> SEQ ID NO 17
<211> LENGTH: 187
<212> TYPE: PRT
<213> ORGANISM: Vibrio furnisii

<400> SEQUENCE: 17

Met Asn Ser Leu Cys Arg Gln Pro Phe Ala Arg Cys Lys Gln Ser Lys
1               5                   10                  15

Pro Lys His Ser Ala Ala Gln Leu Ser Cys Leu Ile His Lys Ile Lys
            20                  25                  30

Glu Lys Glu Thr Met Asp Ile Arg Lys Ile Lys Lys Leu Ile Glu Leu
        35                  40                  45

Val Glu Glu Ser Gly Ile Ala Glu Leu Glu Ile Ser Glu Gly Glu Glu
    50                  55                  60

Ser Val Arg Ile Ser Arg His Gly Val Ala Pro Val Ala Pro Ile Gln
65                  70                  75                  80

Tyr Ala Ala Pro Ala Pro Met Ala Ala Pro Val Ala Pro Ala Ala
                85                  90                  95

Ala Pro Val Ala Glu Ala Pro Ala Ala Lys Thr Pro Ala Gly His
            100                 105                 110

Met Val Leu Ser Pro Met Val Gly Thr Phe Tyr Arg Ser Pro Ser Pro
            115                 120                 125

Asp Ala Lys Ser Phe Ile Glu Val Gly Gln Thr Val Lys Ala Gly Asp
130                 135                 140

Thr Leu Cys Ile Val Glu Ala Met Lys Met Met Asn Gln Ile Glu Ala
145                 150                 155                 160

Asp Lys Ser Gly Val Val Thr Glu Ile Leu Val Glu Asp Gly Gln Ala
                165                 170                 175

Val Glu Phe Asp Gln Pro Leu Val Val Ile Glu
            180                 185

<210> SEQ ID NO 18
<211> LENGTH: 447
<212> TYPE: PRT
<213> ORGANISM: Vibrio furnisii

<400> SEQUENCE: 18

Met Leu Asp Lys Leu Val Ile Ala Asn Arg Gly Glu Ile Ala Leu Arg
1               5                   10                  15

Ile Leu Arg Ala Cys Lys Glu Leu Gly Ile Lys Thr Val Ala Val His
            20                  25                  30

Ser Thr Ala Asp Arg Asp Leu Lys His Val Leu Leu Ala Asp Glu Thr
        35                  40                  45

Val Cys Ile Gly Pro Ala Lys Gly Ile Asp Ser Tyr Leu Asn Ile Pro
    50                  55                  60

Arg Ile Ile Ser Ala Ala Glu Val Thr Gly Ala Val Ala Ile His Pro
65                  70                  75                  80

Gly Tyr Gly Phe Leu Ser Glu Asn Ala Asp Phe Ala Glu Gln Val Glu
                85                  90                  95

Arg Ser Gly Phe Ile Phe Val Gly Pro Lys Ala Asp Thr Ile Arg Leu
            100                 105                 110

Met Gly Asp Lys Val Ser Ala Ile Thr Ala Met Lys Lys Ala Gly Val
```

```
            115                 120                 125
Pro Cys Val Pro Gly Ser Asp Gly Pro Leu Asp Asn Asp Glu Val Lys
            130                 135                 140

Asn Arg Ala His Ala Lys Arg Ile Gly Tyr Pro Val Ile Ile Lys Ala
145                 150                 155                 160

Ser Gly Gly Gly Gly Arg Gly Met Arg Val Val Arg Ser Glu Ala
            165                 170                 175

Glu Leu Val Asn Ala Ile Ser Met Thr Arg Ala Glu Ala Lys Ala Ala
            180                 185                 190

Phe Asn Asn Asp Met Val Tyr Met Glu Lys Tyr Leu Glu Asn Pro Arg
            195                 200                 205

His Val Glu Val Gln Val Leu Ala Asp Gly Gln Gly Ser Ala Ile His
            210                 215                 220

Leu Gly Glu Arg Asp Cys Ser Met Gln Arg Arg His Gln Lys Val Val
225                 230                 235                 240

Glu Glu Ala Pro Ala Pro Gly Ile Thr Glu Glu Met Arg Lys Tyr Ile
            245                 250                 255

Gly Glu Arg Cys Thr Arg Ala Cys Ile Glu Ile Gly Tyr Arg Gly Ala
            260                 265                 270

Gly Thr Phe Glu Phe Leu Tyr Glu Asn Gly Glu Phe Tyr Phe Ile Glu
            275                 280                 285

Met Asn Thr Arg Ile Gln Val Glu His Pro Val Thr Glu Met Val Thr
290                 295                 300

Gly Val Asp Leu Ile Lys Glu Gln Leu Arg Ile Ala Ala Gly Gln Pro
305                 310                 315                 320

Leu Ser Phe Thr Gln Asp Asp Ile Lys Ile Arg Gly His Ala Met Glu
            325                 330                 335

Cys Arg Ile Asn Ala Glu Asp Pro Glu Arg Phe Leu Pro Cys Pro Gly
            340                 345                 350

Lys Ile Thr Arg Phe His Ser Pro Gly Gly Met Gly Val Arg Trp Glu
            355                 360                 365

Ser His Ile Tyr Ser Gly Tyr Thr Val Pro Ala Tyr Tyr Asp Ser Met
370                 375                 380

Ile Gly Lys Leu Ile Thr Phe Gly Glu Asn Arg Asp Val Ala Ile Ala
385                 390                 395                 400

Arg Met Arg Asn Ala Leu Asp Glu Met Ile Val Glu Gly Ile Lys Thr
            405                 410                 415

Asn Ile Pro Leu Gln Gln Val Ile Met Lys Asp Glu Asn Phe Gln His
            420                 425                 430

Gly Gly Thr Asn Ile His Tyr Leu Glu Lys Lys Leu Gly Leu Gln
            435                 440                 445

<210> SEQ ID NO 19
<211> LENGTH: 308
<212> TYPE: PRT
<213> ORGANISM: Vibrio furnisii

<400> SEQUENCE: 19

Met Ser Trp Leu Glu Lys Ile Leu Glu Lys Ser Asn Ile Gly Ser Ser
1               5                   10                  15

Arg Lys Ala Ser Ile Pro Glu Gly Val Trp Thr Lys Cys Thr Ser Cys
            20                  25                  30

Glu Gln Val Leu Tyr Tyr Ala Glu Leu Glu Arg Asn Leu Glu Val Cys
        35                  40                  45
```

```
Pro Lys Cys Asn His His Met Arg Met Lys Ala Arg Arg Leu Glu
 50                  55                  60

Thr Phe Leu Asp Glu Ala Asn Arg Tyr Glu Ile Ala Asp Glu Leu Glu
 65                  70                  75                  80

Pro Gln Asp Lys Leu Lys Phe Lys Asp Ser Lys Arg Tyr Lys Glu Arg
                 85                  90                  95

Leu Ala Thr Ala Gln Lys Ser Ser Gly Glu Lys Asp Ala Leu Ile Val
                100                 105                 110

Met Lys Gly Glu Leu Met Thr Ile Pro Val Val Ala Cys Ala Phe Glu
            115                 120                 125

Phe Ser Phe Met Gly Ser Met Gly Ser Val Gly Ala Arg Phe
130                 135                 140

Val Arg Ala Val Glu Ala Ala Ile Glu Ala Asn Cys Gly Leu Val Cys
145                 150                 155                 160

Phe Ser Ala Ser Gly Gly Ala Arg Met Gln Glu Ala Leu Met Ser Leu
                165                 170                 175

Met Gln Met Ala Lys Thr Ser Ala Ala Leu Glu Arg Leu Thr Ala Lys
                180                 185                 190

Gly Leu Pro Phe Ile Ser Val Met Thr Asp Pro Thr Met Gly Gly Val
            195                 200                 205

Ser Ala Ser Leu Ala Met Leu Gly Asp Ile Asn Ile Gly Glu Pro Lys
210                 215                 220

Ala Leu Ile Gly Phe Ala Gly Arg Arg Val Ile Glu Gln Thr Val Arg
225                 230                 235                 240

Glu Glu Leu Pro Glu Gly Phe Gln Arg Ser Glu Phe Leu Leu Glu His
                245                 250                 255

Gly Ala Ile Asp Met Ile Val Asp Arg Arg Glu Met Arg Gln Arg Val
                260                 265                 270

Ala Gly Leu Leu Ala Lys Met Thr Arg Gln Glu Ser Pro Leu Val Val
            275                 280                 285

Ser Val Asn Asp Ala Pro Asn Glu Ala Ala Tyr Ser Val Pro Glu Ala
    290                 295                 300

Asn Lys Lys Gly
305

<210> SEQ ID NO 20
<211> LENGTH: 814
<212> TYPE: PRT
<213> ORGANISM: Vibrio furnisii

<400> SEQUENCE: 20

Met Asp Ile Leu Leu Ser Ile Leu Gly Phe Val Val Leu Ser Gly
1               5                   10                  15

Cys Leu Tyr His Arg Thr Ser Leu Met Thr Ala Leu Ala Ala Leu Thr
                20                  25                  30

Val Thr Met Leu Val Leu Ser Leu Phe Gly Pro Val Gly Ile Ile Ser
            35                  40                  45

Trp Ala Leu Tyr Leu Ala Ala Ile Ala Val Leu Ala Val Pro Ser Ile
 50                  55                  60

Arg Gln Ser Leu Ile Ser Gly Lys Thr Leu Lys Val Phe Lys Lys Val
 65                  70                  75                  80

Leu Pro Ala Met Ser Gln Thr Glu Lys Glu Ala Leu Asp Ala Gly Thr
                 85                  90                  95

Val Trp Trp Glu Ala Glu Leu Phe Lys Gly Lys Pro Asp Trp Gln Gln
                100                 105                 110
```

```
Leu Ser His Ile Lys Ala Pro Thr Leu Ser Ala Glu Glu Gln Ala Phe
        115                 120                 125

Leu Asp Gly Pro Val Asn Glu Val Cys Ala Met Val Asn Asp Tyr Gln
130                 135                 140

Val Thr His Glu Leu Ala Asp Leu Pro Pro Glu Val Trp Gln Tyr Leu
145                 150                 155                 160

Lys Asp His Lys Phe Phe Ala Met Ile Ile Lys Lys Gln Tyr Gly Gly
                165                 170                 175

Leu Glu Phe Ser Ala Tyr Ala Gln Ser Leu Val Leu Gln Lys Leu Thr
            180                 185                 190

Gly Val Ser Gly Val Leu Ser Ser Thr Val Gly Val Pro Asn Ser Leu
        195                 200                 205

Gly Pro Gly Glu Leu Leu Gln His Tyr Gly Thr Asp Asp Gln Lys Asp
    210                 215                 220

Tyr Tyr Leu Pro Arg Leu Ala Glu Gly Lys Glu Ile Pro Cys Phe Ala
225                 230                 235                 240

Leu Thr Ser Pro Glu Ala Gly Ser Asp Ala Gly Ser Ile Pro Asp Tyr
                245                 250                 255

Gly Ile Val Cys Lys Asp Glu Trp Glu Gly Lys Glu Val Leu Gly Met
                260                 265                 270

Arg Leu Thr Trp Asn Lys Arg Tyr Ile Thr Leu Ala Pro Val Ala Thr
            275                 280                 285

Val Leu Gly Leu Ala Phe Lys Leu Arg Asp Pro Asp Gly Leu Leu Gly
    290                 295                 300

Asp Gln Lys Glu Ile Gly Ile Thr Cys Ala Leu Ile Pro Thr His Leu
305                 310                 315                 320

Lys Gly Val Glu Ile Gly Asn Arg His Phe Pro Leu Asn Val Pro Phe
                325                 330                 335

Gln Asn Gly Pro Thr Arg Ala Asn Asp Leu Phe Val Pro Leu Asp Phe
            340                 345                 350

Ile Ile Gly Gly Pro Ser Met Ala Gly Gln Gly Trp Arg Met Leu Val
        355                 360                 365

Glu Cys Leu Ser Val Gly Arg Gly Ile Thr Leu Pro Ser Asn Ser Thr
    370                 375                 380

Gly Gly Ile Lys Ala Ala Ala Met Ala Thr Gly Ala Tyr Ala Arg Ile
385                 390                 395                 400

Arg Arg Gln Phe Lys Gln Pro Ile Gly His Met Glu Gly Ile Glu Glu
                405                 410                 415

Pro Leu Ala Arg Leu Ala Gly Asn Ala Tyr Val Met Asp Ala Ala Ser
            420                 425                 430

Asn Leu Thr Val Ala Gly Ile Asp Ala Gly Glu Lys Pro Ser Val Ile
        435                 440                 445

Ser Ala Ile Val Lys Tyr His Cys Thr His Arg Gly Gln Arg Ser Ile
    450                 455                 460

Ile Asp Ala Met Asp Ile Val Gly Gly Lys Gly Ile Cys Leu Gly Pro
465                 470                 475                 480

Ser Asn Phe Leu Ala Arg Gly Tyr Gln Gly Ser Pro Ile Ala Ile Thr
                485                 490                 495

Val Glu Gly Ala Asn Ile Leu Thr Arg Ser Met Ile Ile Phe Gly Gln
            500                 505                 510

Gly Ala Ile Arg Cys His Pro Tyr Val Leu Lys Glu Met Glu Ala Ala
        515                 520                 525
```

-continued

```
Tyr Ser Asp Ser Ala Asn Ala Val Glu Gln Phe Asp Ala Ala Leu Ala
            530                 535                 540

Gly His Val Ser Phe Thr Met Ser Asn Leu Val Arg Cys Ile Trp Phe
545                 550                 555                 560

Gly Leu Thr Asp Gly Leu Gly Ser Ala Ala Pro Thr Lys Asp Ala Thr
                565                 570                 575

Lys Arg Tyr Tyr Gln Gln Leu Asn Arg Tyr Ser Ala Asn Leu Ala Leu
            580                 585                 590

Leu Ala Asp Ile Ser Met Ala Val Leu Gly Gly Ser Leu Lys Arg Lys
        595                 600                 605

Glu Arg Leu Ser Ala Arg Leu Gly Asp Ile Leu Ser Gln Leu Tyr Leu
610                 615                 620

Ser Ser Ala Thr Leu Lys Arg Phe Glu Asn Asp Gly Arg Pro Ala Glu
625                 630                 635                 640

Asp Leu Ala Leu Val His Trp Gly Leu Gln Asp Ser Leu Lys Gln Thr
                645                 650                 655

Glu Val Ala Ile Asp Glu Phe Leu Ala Asn Phe Pro Asn Lys Val Ile
            660                 665                 670

Gly Lys Ala Leu Arg Val Leu Ile Met Pro Phe Gly Arg Val Arg Lys
        675                 680                 685

Ala Pro Asn Asp Lys Leu Asp Ser Lys Val Ala Gln Ile Ile Gln Thr
690                 695                 700

Pro Ser Ala Thr Arg Ser Arg Ile Gly Arg His Gln Tyr Leu Glu Pro
705                 710                 715                 720

Thr Ala His Asn Ala Val Gly Lys Ile Glu Leu Ala Leu Asn Val Ile
                725                 730                 735

Leu Gln Ala Glu Pro Val Phe Asp Lys Val Cys Lys Ala Leu Asn Glu
            740                 745                 750

Arg Arg Pro Phe Thr Gln Leu Asp Gln Val Ala Gln Cys Gly Leu Glu
        755                 760                 765

Gln Lys Leu Ile Thr Glu Gln Glu Ala Glu Leu Ile Glu Ala Glu
770                 775                 780

Gln His Arg Leu Tyr Thr Ile Asn Val Asp Asp Phe Ala Pro Gln Glu
785                 790                 795                 800

Leu Ala Ala Lys Lys Ser Gln Pro Lys Leu Val Glu Val Ala
                805                 810

<210> SEQ ID NO 21
<211> LENGTH: 807
<212> TYPE: PRT
<213> ORGANISM: Vibrio furnisii

<400> SEQUENCE: 21

Met Ser Ser Gly His Ser Phe Ser Arg Ser Leu Leu Lys Leu Pro Leu
1               5                   10                  15

Ser Val Leu Val Lys Gly Thr Val Ile Pro Ser Asn Pro Ile Asp Asp
            20                  25                  30

Leu Glu Ile Asp Ile Asn Lys Pro Ile Val Tyr Ala Leu Pro Phe Arg
        35                  40                  45

Ser Asn Val Asp Leu Leu Thr Leu Gln Thr His Ala Leu Gln Ala Gly
    50                  55                  60

Leu Pro Asp Pro Leu Glu Pro Leu Thr Ile His Ser His Thr Leu Lys
65                  70                  75                  80

Arg Tyr Val Phe Ile Ser Ser Arg Pro Thr Leu Leu Gln Asp Asp Asn
                85                  90                  95
```

-continued

```
Gln Val Pro Thr Asp Ser Ile Ala Thr Phe Ser Glu Met Leu Ser Leu
                100                 105                 110

His Gln Glu Asp Ser Glu Leu Asp Val Gln Val Ile Pro Ala Thr Val
            115                 120                 125

Leu Trp Gly Arg Lys Pro Gly Lys Gly Arg Glu Arg Pro Tyr Leu
        130                 135                 140

Gln Ala Leu Asn Gly Pro Gln Lys Ala Lys Ala Val Phe Ala Ala Gly
145                 150                 155                 160

Arg Asp Cys Leu Val Arg Phe Ser Pro Val Val Ser Leu Arg Tyr Met
                165                 170                 175

Ala Asp Ser His Gly Thr Asp Ala Ser Ile Ala His Lys Leu Ala Arg
            180                 185                 190

Val Ala Arg Ile His Phe Ser Arg Gln Lys Leu Ala Ala Ser Gly Pro
        195                 200                 205

Asn Leu Pro Gln Arg His Gln Leu Phe Gln Arg Leu Met Asn Ser Pro
    210                 215                 220

Ala Ile Glu Lys Ala Ile Ala Asp Glu Ala Ala Lys Asn Ile Ser
225                 230                 235                 240

Leu Glu Lys Ala Arg Lys Glu Ala His Asp Met Leu Asp Glu Ile Ala
                245                 250                 255

Ala Asp Phe Ser Tyr Ser Leu Val Arg Lys Gly Asp Arg Ile Leu Gly
            260                 265                 270

Trp Leu Trp Asn Arg Ile Tyr Gln Gly Leu Asn Ile Asn Asn Ala Ala
        275                 280                 285

Thr Val Arg Arg Leu Ala Gln Asp Gly His Glu Ile Val Tyr Val Pro
    290                 295                 300

Cys His Arg Ser His Met Asp Tyr Leu Leu Leu Ser Tyr Val Leu Tyr
305                 310                 315                 320

His Glu Gly Met Val Pro Pro His Ile Ala Ala Gly Ile Asn Leu Asn
                325                 330                 335

Phe Phe Pro Ala Gly Pro Ile Phe Arg Arg Gly Gly Ala Phe Phe Ile
            340                 345                 350

Arg Arg Ser Phe Lys Gly Asn Lys Leu Tyr Ser Thr Ile Phe Arg Glu
        355                 360                 365

Tyr Leu Ala Glu Leu Phe Ala Lys Gly Tyr Ser Val Glu Tyr Phe Ser
    370                 375                 380

Glu Gly Gly Arg Ser Arg Thr Gly Arg Leu Leu Gln Ala Lys Thr Gly
385                 390                 395                 400

Met Leu Ala Met Thr Ile Gln Ala Met Leu Arg Gly Leu Asn Arg Pro
                405                 410                 415

Val Thr Leu Val Pro Val Tyr Ile Gly Tyr Glu His Val Met Glu Val
            420                 425                 430

Gly Thr Tyr Ala Lys Glu Leu Arg Gly Lys Arg Lys Glu Lys Glu Asn
        435                 440                 445

Ala Ser Leu Val Leu Arg Thr Ile Arg Lys Leu Arg Asn Phe Gly Gln
    450                 455                 460

Gly Tyr Val Asn Phe Gly Glu Pro Ile Pro Leu Asn Gln Phe Leu Asn
465                 470                 475                 480

Glu Gln Val Pro Glu Trp Thr Gln Asp Ile Asp Ala Met Gly Ala Ser
                485                 490                 495

Lys Pro Gln Trp Met Thr Pro Val Asn Lys Leu Ala Thr Lys Met
            500                 505                 510
```

Met Thr His Ile Asn Asp Ala Ala Ala Asn Ala Met Thr Leu Cys
            515                 520                 525

Ala Thr Ala Leu Leu Ala Ser Arg Gln Arg Ala Leu Ala Arg Asp Asn
530                 535                 540

Leu Val Lys Gln Ile Asp Cys Tyr Leu Gln Leu Leu Arg Asn Val Pro
545                 550                 555                 560

Tyr Ser Asn Thr Tyr Thr Val Pro Ser Asp Ser Ala Glu Ser Leu Val
                565                 570                 575

Gln His Ala Glu Ser Leu Asp Lys Phe Val Val Glu Thr Asp Thr Met
            580                 585                 590

Gly Asp Ile Ile Ser Leu Asp Arg Asn Gln Ser Ile Leu Met Thr Tyr
        595                 600                 605

Tyr Arg Asn Asn Ile Ile His Leu Leu Ala Leu Pro Ser Leu Ile Ala
610                 615                 620

Gln Met Leu Ile Arg Gln Gln Gln Met Pro Val Glu Gln Ile Gln Thr
625                 630                 635                 640

Cys Val Ala Lys Val Tyr Pro Phe Leu Lys Gln Glu Leu Phe Leu Ser
                645                 650                 655

His Asp Glu Thr Gln Leu Asp Glu Val Val Met His Tyr Leu Ala Glu
            660                 665                 670

Leu Gln Arg Gln Gln Leu Val Thr Leu Asp Asp Gly Ile Ala Thr Ile
        675                 680                 685

Asn Gln Ala Gln Thr Gln Val Leu Met Leu Leu Gly Arg Thr Ile Ser
690                 695                 700

Glu Thr Leu Gln Arg Tyr Ala Ile Thr Leu Asn Leu Leu Val Ala Asn
705                 710                 715                 720

Pro Glu Leu Gly Lys Ser Asp Leu Glu Ser Lys Ser Gln Glu Ile Ala
                725                 730                 735

Gln Arg Leu Gly Arg Leu His Gly Ile Asn Ala Pro Glu Phe Phe Asp
            740                 745                 750

Lys Gly Val Phe Ser Ser Met Phe Val Thr Leu Lys Gln Gln Gly Tyr
        755                 760                 765

Leu Asp Ser Asp Gly Asn Cys His Leu Asp Gln Thr Lys His Phe Ser
770                 775                 780

Arg Met Leu Tyr Thr Met Leu Tyr Pro Glu Val Arg Leu Thr Ile Gln
785                 790                 795                 800

Glu Ser Ile Cys Gln Val Glu
                805

<210> SEQ ID NO 22
<211> LENGTH: 886
<212> TYPE: PRT
<213> ORGANISM: Vibrio furnisii

<400> SEQUENCE: 22

Met Ser Asp Met Lys His Asp Val Asp Ala Leu Glu Thr Gln Glu Trp
1               5                   10                  15

Leu Ala Ala Leu Glu Ser Val Val Arg Glu Glu Gly Val Glu Arg Ala
            20                  25                  30

Gln Tyr Leu Leu Glu Glu Val Leu Glu Lys Ala Arg Leu Asp Gly Val
        35                  40                  45

Asp Met Pro Thr Gly Ile Thr Thr Asn Tyr Ile Asn Thr Ile Pro Ala
    50                  55                  60

Ala Gln Glu Pro Ala Tyr Pro Gly Asp Thr Thr Ile Glu Arg Arg Ile
65                  70                  75                  80

```
Arg Ser Ile Ile Arg Trp Asn Ala Ile Met Ile Val Leu Arg Ala Ser
                85                  90                  95

Lys Lys Asp Leu Asp Leu Gly Gly His Met Ala Ser Phe Gln Ser Ser
            100                 105                 110

Ala Ala Phe Tyr Glu Thr Cys Phe Asn His Phe Phe Arg Ala Pro Asn
        115                 120                 125

Glu Lys Asp Gly Gly Asp Leu Val Tyr Tyr Gln Gly His Ile Ser Pro
    130                 135                 140

Gly Ile Tyr Ala Arg Ala Phe Val Glu Gly Arg Leu Thr Glu Glu Gln
145                 150                 155                 160

Leu Asp Asn Phe Arg Gln Glu Val Asp Gly Lys Gly Ile Pro Ser Tyr
                165                 170                 175

Pro His Pro Lys Leu Met Pro Glu Phe Trp Gln Phe Pro Thr Val Ser
            180                 185                 190

Met Gly Leu Gly Pro Ile Ala Ser Ile Tyr Gln Ala Arg Phe Leu Lys
        195                 200                 205

Tyr Leu Glu Gly Arg Gly Met Lys Asp Thr Ala Glu Gln Arg Val Tyr
    210                 215                 220

Ala Phe Leu Gly Asp Gly Glu Met Asp Glu Pro Glu Ser Arg Gly Ala
225                 230                 235                 240

Ile Ser Phe Ala Ala Arg Glu Lys Leu Asp Asn Leu Cys Phe Leu Ile
                245                 250                 255

Asn Cys Asn Leu Gln Arg Leu Asp Gly Pro Val Met Gly Asn Gly Lys
            260                 265                 270

Ile Ile Gln Glu Leu Glu Gly Leu Phe Lys Gly Ala Gly Trp Asn Val
        275                 280                 285

Val Lys Val Ile Trp Gly Asn Asn Trp Asp Ser Leu Leu Ala Lys Asp
    290                 295                 300

Thr Ser Gly Lys Leu Leu Gln Leu Met Asn Glu Thr Ile Asp Gly Asp
305                 310                 315                 320

Tyr Gln Thr Phe Lys Ala Lys Asp Gly Ala Tyr Val Arg Glu His Phe
                325                 330                 335

Phe Gly Lys Tyr Pro Glu Thr Ala Ala Leu Val Ala Asp Met Thr Asp
            340                 345                 350

Asp Glu Val Phe Ala Leu Lys Arg Gly Gly His Glu Ser Ser Lys Leu
        355                 360                 365

Tyr Ala Ala Phe Lys Asn Ala Gln Asp Thr Lys Gly Arg Pro Thr Val
    370                 375                 380

Ile Leu Ala Lys Thr Val Lys Gly Tyr Gly Met Gly Asp Ala Ala Gln
385                 390                 395                 400

Gly Lys Asn Ile Ala His Gln Val Lys Lys Met Asp Met Thr His Val
                405                 410                 415

Ile Ala Met Arg Asn Arg Leu Gly Leu Gln Asp Ile Ile Ser Asp Glu
            420                 425                 430

Glu Val Asn Asn Leu Pro Tyr Leu Lys Leu Glu Glu Gly Ser Lys Glu
        435                 440                 445

Phe Glu Tyr Leu His Ala Arg Arg Lys Ala Leu His Gly Tyr Thr Pro
    450                 455                 460

Gln Arg Leu Pro Lys Phe Thr Gln Glu Leu Val Ile Pro Glu Leu Glu
465                 470                 475                 480

Glu Phe Lys Pro Leu Leu Glu Glu Gln Lys Arg Glu Ile Ser Ser Thr
                485                 490                 495
```

-continued

Met Ala Tyr Val Arg Ala Leu Asn Ile Leu Lys Asp Lys Asn Ile
            500                 505                 510

Gly Lys Asn Ile Val Pro Ile Ile Ala Asp Glu Ala Arg Thr Phe Gly
        515                 520                 525

Met Glu Gly Leu Phe Arg Gln Ile Gly Ile Tyr Asn Pro His Gly Gln
    530                 535                 540

Thr Tyr Thr Pro Glu Asp Arg Gly Val Val Ser Tyr Lys Glu Asp
545                 550                 555                 560

Thr Ala Gly Gln Val Leu Gln Glu Gly Ile Asn Glu Leu Gly Ala Met
                565                 570                 575

Ser Ser Trp Val Ala Ala Thr Ser Tyr Ser Thr Asn Asn Leu Pro
            580                 585                 590

Met Ile Pro Phe Tyr Ile Tyr Tyr Ser Met Phe Gly Phe Gln Arg Val
            595                 600                 605

Gly Asp Met Ala Trp Met Ala Gly Asp Gln Gln Ala Arg Gly Phe Leu
        610                 615                 620

Leu Gly Ala Thr Ala Gly Arg Thr Thr Leu Asn Gly Glu Gly Leu Gln
625                 630                 635                 640

His Glu Asp Gly His Ser His Ile Gln Ala Ala Thr Ile Pro Asn Cys
                645                 650                 655

Ile Ser Tyr Asp Pro Thr Phe Ala Tyr Glu Val Ala Val Ile Met Gln
            660                 665                 670

Asp Gly Ile Arg Arg Met Tyr Gly Asp Gln Glu Asn Val Phe Tyr Tyr
        675                 680                 685

Met Thr Leu Met Asn Glu Asn Tyr Ala His Pro Ala Met Pro Glu Gly
    690                 695                 700

Ala Glu Glu Gly Ile Arg Lys Gly Ile Tyr Lys Leu Glu Thr Leu Ser
705                 710                 715                 720

Gly Ser Lys Gly Lys Val Gln Leu Met Ser Ser Gly Thr Ile Met Asn
                725                 730                 735

Glu Val Arg Lys Ala Ala Val Ile Leu Ser Glu Tyr Gly Ile Ala
            740                 745                 750

Ser Asp Val Tyr Ser Val Thr Ser Phe Asn Glu Leu Ala Arg Asp Gly
        755                 760                 765

Gln Asn Val Glu Arg Tyr Asn Met Leu His Pro Glu Ala Glu Ala Gln
    770                 775                 780

Val Pro Tyr Ile Ala Ser Val Met Gly Thr Glu Pro Ala Ile Ala Ala
785                 790                 795                 800

Thr Asp Tyr Met Lys Asn Tyr Ala Asp Gln Val Arg Ala Phe Ile Pro
                805                 810                 815

Ala Glu Ser Tyr Lys Val Leu Gly Thr Asp Gly Phe Gly Arg Ser Asp
            820                 825                 830

Ser Arg Glu Asn Leu Arg Arg His Phe Glu Val Asn Ala Gly Tyr Val
        835                 840                 845

Val Val Ala Ala Leu Asn Glu Leu Ala Lys Arg Gly Glu Val Glu Lys
    850                 855                 860

Ser Val Val Ala Glu Ala Ile Lys Lys Phe Asp Ile Asp Thr Glu Lys
865                 870                 875                 880

Thr Asn Pro Leu Tyr Ala
                885

<210> SEQ ID NO 23
<211> LENGTH: 630
<212> TYPE: PRT

<213> ORGANISM: Vibrio furnisii

<400> SEQUENCE: 23

```
Met Ala Ile Glu Ile Tyr Val Pro Asp Ile Gly Ala Asp Glu Val Glu
1               5                  10                  15

Val Thr Glu Ile Leu Val Ser Val Gly Asp Lys Val Glu Glu Glu Gln
            20                  25                  30

Ser Leu Ile Thr Val Glu Gly Asp Lys Ala Ser Met Glu Val Pro Ala
        35                  40                  45

Ser Gln Ala Gly Ile Val Lys Glu Ile Lys Val Val Thr Gly Asp Lys
    50                  55                  60

Val Thr Thr Gly Ser Leu Ile Met Val Phe Glu Ala Glu Gly Ala Ala
65                  70                  75                  80

Ala Ala Ala Pro Ala Pro Ala Ala Glu Ala Ala Pro Val Ala Ala Ala
                85                  90                  95

Pro Ala Ala Val Glu Leu Lys Glu Val Asn Val Pro Asp Ile Gly Gly
            100                 105                 110

Asp Glu Val Glu Val Thr Glu Ile Met Val Ala Val Gly Asp Thr Val
        115                 120                 125

Ser Glu Glu Gln Ser Leu Ile Thr Val Glu Gly Asp Lys Ala Ser Met
    130                 135                 140

Glu Val Pro Ala Pro Phe Ala Gly Thr Val Lys Glu Ile Lys Ile Ala
145                 150                 155                 160

Ser Gly Asp Lys Val Thr Thr Gly Ser Leu Ile Met Val Phe Glu Val
                165                 170                 175

Ala Gly Ser Gly Ala Pro Ala Ala Ala Pro Ala Gln Ala Ala Ala
            180                 185                 190

Pro Ala Ala Ala Pro Ala Val Ala Ala Asp Lys Glu Val Asn Val Pro
        195                 200                 205

Asp Ile Gly Gly Asp Glu Val Glu Val Thr Glu Ile Met Val Ala Val
    210                 215                 220

Gly Asp Met Val Ser Glu Glu Gln Ser Leu Ile Thr Val Glu Gly Asp
225                 230                 235                 240

Lys Ala Ser Met Glu Val Pro Ala Pro Phe Ala Gly Lys Val Lys Ala
                245                 250                 255

Ile Lys Val Ala Ala Gly Asp Lys Val Ser Thr Gly Ser Leu Ile Met
            260                 265                 270

Val Phe Glu Val Ala Gly Ala Ala Pro Ala Val Ser Ala Pro Ala
        275                 280                 285

Gln Ala Ala Ala Pro Ala Ala Ala Pro Lys Ala Glu Ala Pro Ala
    290                 295                 300

Ala Ala Ala Pro Ala Ala Ala Thr Gly Asp Phe Gln Glu Asn Asn Glu
305                 310                 315                 320

Tyr Ala His Ala Ser Pro Val Val Arg Arg Leu Ala Arg Glu Phe Gly
                325                 330                 335

Val Asn Leu Ser Lys Val Lys Gly Ser Gly Arg Lys Ser Arg Ile Leu
            340                 345                 350

Lys Glu Asp Val Gln Asn Tyr Val Lys Glu Ala Leu Lys Arg Leu Glu
        355                 360                 365

Ser Gly Ala Ala Ser Ala Ala Ser Gly Lys Gly Asp Gly Ala Ala Leu
    370                 375                 380

Gly Leu Leu Pro Trp Pro Lys Val Asp Phe Ser Lys Phe Gly Asp Thr
385                 390                 395                 400
```

Glu Ile Gln Pro Leu Ser Arg Ile Lys Lys Ile Ser Gly Ala Asn Leu
            405                 410                 415

His Arg Asn Trp Val Met Ile Pro His Val Thr Gln Trp Asp Asn Ala
        420                 425                 430

Asp Ile Thr Glu Leu Glu Ala Phe Arg Lys Glu Gln Asn Ala Ile Glu
        435                 440                 445

Ala Lys Lys Asp Thr Gly Met Lys Ile Thr Pro Leu Val Phe Ile Met
    450                 455                 460

Lys Ala Ala Lys Ala Leu Glu Ala Phe Pro Ala Phe Asn Ser Ser
465                 470                 475                 480

Leu Ser Glu Asp Gly Glu Ser Leu Ile Leu Lys Lys Tyr Val Asn Ile
                485                 490                 495

Gly Ile Ala Val Asp Thr Pro Asn Gly Leu Val Val Pro Val Phe Lys
                500                 505                 510

Asp Val Asn Lys Lys Gly Ile Tyr Glu Leu Ser Glu Glu Leu Ala Val
            515                 520                 525

Val Ser Lys Lys Ala Arg Ala Gly Lys Leu Thr Ala Ser Asp Met Gln
        530                 535                 540

Gly Gly Cys Phe Thr Ile Ser Ser Leu Gly Gly Ile Gly Gly Thr Ala
545                 550                 555                 560

Phe Thr Pro Ile Val Asn Ala Pro Glu Val Gly Ile Leu Gly Val Ser
                565                 570                 575

Lys Ser Glu Met Lys Pro Val Trp Asn Gly Lys Glu Phe Ala Pro Arg
                580                 585                 590

Leu Gln Leu Pro Leu Ser Leu Ser Tyr Asp His Arg Val Ile Asp Gly
            595                 600                 605

Ala Glu Gly Ala Arg Phe Ile Thr Tyr Leu Asn Gly Cys Leu Ser Asp
        610                 615                 620

Ile Arg Arg Leu Val Leu
625                 630

<210> SEQ ID NO 24
<211> LENGTH: 316
<212> TYPE: PRT
<213> ORGANISM: Vibrio furnisii

<400> SEQUENCE: 24

Met Tyr Ser Lys Ile Leu Gly Thr Gly Ser Tyr Leu Pro Ser Gln Val
1               5                   10                  15

Arg Thr Asn Ala Asp Leu Glu Lys Met Val Asp Thr Ser Asp Glu Trp
            20                  25                  30

Ile Val Thr Arg Thr Gly Ile Arg Glu Arg Arg Ile Ala Ala Asp Asn
        35                  40                  45

Glu Thr Val Ala Asp Met Gly Phe Tyr Ala Ala Gln Asn Ala Ile Glu
    50                  55                  60

Met Ala Gly Ile Asp Lys Asn Asp Ile Asp Leu Ile Ile Leu Ala Thr
65                  70                  75                  80

Thr Ser Ser Ser His Thr Phe Pro Ser Ala Cys Gln Val Gln Ala
                85                  90                  95

Lys Leu Gly Ile Lys Gly Cys Pro Ala Phe Asp Leu Ala Ala Cys
            100                 105                 110

Ser Gly Phe Ile Tyr Gly Leu Ser Val Ala Asp Gln His Ile Lys Ser
        115                 120                 125

Gly Met Cys Lys Asn Val Leu Val Ile Gly Ala Asp Ala Leu Ser Lys
    130                 135                 140

Thr Cys Asp Pro Thr Asp Arg Ser Thr Ile Ile Leu Phe Gly Asp Gly
145                 150                 155                 160

Ala Gly Ala Val Val Gly Ala Ser Glu Glu Pro Gly Ile Leu Ser
            165                 170                 175

Thr His Val Tyr Ala Asp Gly Gln Phe Gly Asp Leu Leu Ser Leu Glu
            180                 185                 190

Val Pro Glu Arg Gly Gly Asp Val Asp Lys Trp Leu Tyr Met Ala Gly
        195                 200                 205

Asn Glu Val Phe Lys Val Ala Val Thr Gln Leu Ser Lys Leu Val Lys
    210                 215                 220

Asp Thr Leu Ala Ala Asn Asn Met His Lys Ser Glu Leu Asp Trp Leu
225                 230                 235                 240

Val Pro His Gln Ala Asn Tyr Arg Ile Ile Ser Ala Thr Ala Lys Lys
                245                 250                 255

Leu Ser Met Ser Leu Asp Gln Val Val Ile Thr Leu Asp Arg His Gly
            260                 265                 270

Asn Thr Ser Ala Ala Thr Val Pro Thr Ala Leu Asp Glu Ala Val Arg
        275                 280                 285

Asp Gly Arg Ile Lys Arg Gly Gln Thr Leu Leu Leu Gly Ala Phe Gly
    290                 295                 300

Gly Gly Phe Thr Trp Gly Ser Ala Leu Val Lys Phe
305                 310                 315

<210> SEQ ID NO 25
<211> LENGTH: 307
<212> TYPE: PRT
<213> ORGANISM: Vibrio furnisii

<400> SEQUENCE: 25

Met Ser Lys Phe Ala Ile Val Phe Pro Gly Gln Gly Ser Gln Ala Val
1               5                   10                  15

Gly Met Leu Ala Glu Leu Gly Glu Gln Tyr Asp Val Val Lys Gln Thr
            20                  25                  30

Phe Ala Glu Ala Ser Asp Ala Leu Gly Tyr Asp Leu Trp Ala Leu Val
        35                  40                  45

Gln Asn Gly Pro Val Glu Asp Leu Asn Gln Thr Phe Arg Thr Gln Pro
    50                  55                  60

Ala Leu Leu Ala Ser Ser Val Ala Ile Trp Arg Val Trp Gln Ala Leu
65                  70                  75                  80

Gly Leu Glu Gln Pro Glu Val Leu Ala Gly His Ser Leu Gly Glu Tyr
                85                  90                  95

Ser Ala Leu Val Cys Ala Gly Val Ile Asp Phe Lys Ala Ala Ile Lys
            100                 105                 110

Leu Val Glu Leu Arg Gly Gln Leu Met Gln Glu Ala Val Pro Ala Gly
        115                 120                 125

Thr Gly Ala Met Tyr Ala Ile Ile Gly Leu Asp Asp Ala Ala Ile Ala
    130                 135                 140

Lys Ala Cys Glu Asp Ala Ala Gln Gly Asp Val Val Ser Pro Val Asn
145                 150                 155                 160

Phe Asn Ser Pro Gly Gln Val Val Ile Ala Gly Gln Lys Asp Ala Val
                165                 170                 175

Glu Arg Ala Gly Ala Leu Cys Lys Glu Ala Gly Ala Lys Arg Ala Leu
            180                 185                 190

Pro Leu Pro Val Ser Val Pro Ser His Cys Ala Leu Met Lys Pro Ala

```
                195                 200                 205
Ala Glu Lys Leu Ala Val Ala Leu Glu Ala Leu Glu Phe Asn Ala Pro
            210                 215                 220

Gln Ile Pro Val Ile Asn Asn Val Asp Val Ala Thr Glu Thr Asp Pro
225                 230                 235                 240

Ala Lys Ile Lys Asp Ala Leu Val Arg Gln Leu His Ser Pro Val Arg
                245                 250                 255

Trp Thr Glu Gly Val Glu Lys Met Ala Ala Gln Gly Ile Glu Lys Leu
                260                 265                 270

Ile Glu Val Gly Pro Gly Lys Val Leu Thr Gly Leu Thr Lys Arg Ile
                275                 280                 285

Val Lys Thr Leu Asp Ala Ala Ala Val Asn Asp Ile Ala Ser Leu Glu
            290                 295                 300

Ala Val Lys
305

<210> SEQ ID NO 26
<211> LENGTH: 248
<212> TYPE: PRT
<213> ORGANISM: Vibrio furnisii

<400> SEQUENCE: 26

Met Ser Asn Phe Met Asn Leu Glu Gly Lys Ile Val Leu Val Thr Gly
1               5                   10                  15

Ala Ser Arg Gly Ile Gly Lys Ala Ile Ala Glu Leu Leu Val Glu Arg
                20                  25                  30

Gly Ala Thr Val Ile Gly Thr Ala Thr Ser Glu Ser Gly Ala Asp Ala
            35                  40                  45

Ile Ser Ala Tyr Leu Gly Asp Asn Gly Lys Gly Leu Ala Leu Asn Val
        50                  55                  60

Thr Asp Val Ala Ser Ile Glu Ser Val Leu Lys Ser Ile Asn Asp Glu
65                  70                  75                  80

Phe Gly Gly Val Asp Ile Leu Val Asn Asn Ala Gly Ile Thr Arg Asp
                85                  90                  95

Asn Leu Leu Met Arg Met Lys Asp Asp Glu Trp Thr Asp Ile Leu Asp
            100                 105                 110

Thr Asn Leu Thr Ser Ile Phe Arg Leu Ser Lys Ala Val Leu Arg Gly
        115                 120                 125

Met Met Lys Lys Arg Gln Gly Arg Ile Ile Asn Val Gly Ser Val Val
130                 135                 140

Gly Thr Met Gly Asn Ala Gly Gln Thr Asn Tyr Ala Ala Ala Lys Ala
145                 150                 155                 160

Gly Val Ile Gly Phe Thr Lys Ser Met Ala Arg Glu Val Ala Ser Arg
                165                 170                 175

Gly Val Thr Val Asn Thr Val Ala Pro Gly Phe Ile Glu Thr Asp Met
            180                 185                 190

Thr Lys Ala Leu Asn Asp Asp Gln Arg Ala Ala Thr Leu Ala Gln Val
        195                 200                 205

Pro Ala Gly Arg Leu Gly Asp Pro Arg Glu Ile Ala Ser Ala Val Ala
    210                 215                 220

Phe Leu Ala Ser Pro Glu Ala Ala Tyr Ile Thr Gly Glu Thr Leu His
225                 230                 235                 240

Val Asn Gly Gly Met Tyr Met Val
                245
```

<210> SEQ ID NO 27
<211> LENGTH: 77
<212> TYPE: PRT
<213> ORGANISM: Vibrio furnisii

<400> SEQUENCE: 27

Met Ser Asn Ile Glu Glu Arg Val Lys Lys Ile Ile Val Glu Gln Leu
1               5                   10                  15

Gly Val Asp Glu Ala Glu Val Lys Asn Glu Ala Ser Phe Val Glu Asp
            20                  25                  30

Leu Gly Ala Asp Ser Leu Asp Thr Val Glu Leu Val Met Ala Leu Glu
        35                  40                  45

Glu Glu Phe Asp Thr Glu Ile Pro Asp Glu Glu Ala Glu Lys Ile Thr
    50                  55                  60

Thr Val Gln Ala Ala Ile Asp Tyr Val Asn Ser Ala Gln
65                  70                  75

<210> SEQ ID NO 28
<211> LENGTH: 416
<212> TYPE: PRT
<213> ORGANISM: Vibrio furnisii

<400> SEQUENCE: 28

Met Ile Val Ser Lys Arg Val Val Thr Gly Met Gly Met Leu
1               5                   10                  15

Ser Pro Val Gly Asn Thr Val Glu Ser Ser Trp Lys Ala Leu Leu Ala
            20                  25                  30

Gly Gln Ser Gly Ile Val Asn Ile Glu His Phe Asp Thr Thr Asn Phe
        35                  40                  45

Ser Thr Arg Phe Ala Gly Leu Val Lys Asp Phe Asn Cys Glu Glu Tyr
    50                  55                  60

Met Ser Lys Lys Asp Ala Arg Lys Met Asp Leu Phe Ile Gln Tyr Gly
65                  70                  75                  80

Ile Ala Ala Gly Ile Gln Ala Leu Asp Asp Ser Gly Leu Val Ile Thr
                85                  90                  95

Glu Glu Asn Ala Pro Arg Val Gly Val Ala Ile Gly Ser Gly Ile Gly
            100                 105                 110

Gly Leu Asp Leu Ile Glu Lys Gly His Gln Ala Leu Met Glu Lys Gly
        115                 120                 125

Pro Arg Lys Val Ser Pro Phe Phe Val Pro Ser Thr Ile Val Asn Met
    130                 135                 140

Val Ala Gly Asn Leu Ser Ile Met Arg Gly Leu Arg Gly Pro Asn Ile
145                 150                 155                 160

Ala Ile Ser Thr Ala Cys Thr Thr Gly Leu His Asn Ile Gly His Ala
                165                 170                 175

Ala Arg Met Ile Ala Tyr Gly Asp Ala Glu Ala Met Val Ala Gly Gly
            180                 185                 190

Ser Glu Lys Ala Ser Thr Pro Leu Gly Met Ala Gly Phe Gly Ala Ala
        195                 200                 205

Lys Ala Leu Ser Thr Arg Asn Asp Glu Pro Ala Lys Ala Ser Arg Pro
    210                 215                 220

Trp Asp Lys Asp Arg Asp Gly Phe Val Leu Gly Asp Gly Ala Gly Val
225                 230                 235                 240

Met Val Leu Glu Gly Tyr Glu His Ala Lys Ala Arg Gly Ala Lys Ile
                245                 250                 255

-continued

```
Tyr Ala Glu Ile Val Gly Phe Gly Met Ser Gly Asp Ala Tyr His Met
            260                 265                 270

Thr Ser Pro Ser Glu Asp Gly Ser Gly Gly Ala Leu Ala Met Glu Ala
        275                 280                 285

Ala Met Arg Asp Ala Ala Leu Ala Gly Thr Gln Ile Gly Tyr Val Asn
    290                 295                 300

Ala His Gly Thr Ser Thr Pro Ala Gly Asp Val Ala Glu Val Lys Gly
305                 310                 315                 320

Ile Lys Arg Ala Leu Gly Glu Asp Gly Ala Lys Gln Val Leu Ile Ser
                325                 330                 335

Ser Thr Lys Ser Met Thr Gly His Leu Leu Gly Ala Ala Gly Ser Val
            340                 345                 350

Glu Ala Ile Ile Thr Val Met Ser Leu Val Asp Gln Ile Val Pro Pro
        355                 360                 365

Thr Ile Asn Leu Asp Asn Pro Glu Glu Gly Leu Gly Val Asp Leu Val
    370                 375                 380

Pro His Thr Ala Arg Lys Val Glu Gly Met Glu Tyr Ala Met Cys Asn
385                 390                 395                 400

Ser Phe Gly Phe Gly Gly Thr Asn Gly Ser Leu Ile Phe Lys Arg Val
                405                 410                 415

<210> SEQ ID NO 29
<211> LENGTH: 344
<212> TYPE: PRT
<213> ORGANISM: Vibrio furnisii

<400> SEQUENCE: 29

Met Thr Asp Ser His Thr Asn Asn Ala Tyr Gly Lys Ala Ile Ala Met
1               5                   10                  15

Thr Val Ile Gly Ala Gly Ser Tyr Gly Thr Ser Leu Ala Ile Ser Leu
            20                  25                  30

Ala Arg Asn Gly Ala Asn Val Val Leu Trp Gly His Asp Pro Val His
        35                  40                  45

Met Ala Arg Leu Glu Ala Glu Arg Ala Asn His Glu Phe Leu Pro Asp
    50                  55                  60

Ile Asp Phe Pro Pro Ser Leu Ile Ile Glu Ser Asp Leu Gln Lys Ala
65                  70                  75                  80

Val Gln Ala Ser Arg Asp Leu Leu Val Val Pro Ser His Val Phe
                85                  90                  95

Ala Ile Val Leu Asn Ser Leu Gln Pro Tyr Leu Arg Glu Asp Thr Arg
            100                 105                 110

Ile Cys Trp Ala Thr Lys Gly Leu Glu Pro Asp Thr Gly Arg Leu Leu
        115                 120                 125

Gln Asp Val Ala His Asp Val Leu Gly Glu Ser His Pro Leu Ala Val
    130                 135                 140

Leu Ser Gly Pro Thr Phe Ala Lys Glu Leu Ala Met Gly Met Pro Thr
145                 150                 155                 160

Ala Ile Ser Val Ala Ser Pro Asp Ala Gln Phe Val Ala Asp Leu Gln
                165                 170                 175

Glu Lys Ile His Cys Ser Lys Thr Phe Arg Val Tyr Ala Asn Ser Asp
            180                 185                 190

Phe Ile Gly Met Gln Leu Gly Gly Ala Val Lys Asn Val Ile Ala Ile
        195                 200                 205

Gly Ala Gly Met Ser Asp Gly Ile Gly Phe Gly Ala Asn Ala Arg Thr
    210                 215                 220
```

```
Ala Leu Ile Thr Arg Gly Leu Ala Glu Met Thr Arg Leu Gly Ala Ala
225                 230                 235                 240

Leu Gly Ala Gln Pro Glu Thr Phe Met Gly Met Ala Gly Leu Gly Asp
            245                 250                 255

Leu Val Leu Thr Cys Thr Asp Asn Gln Ser Arg Asn Arg Arg Phe Gly
            260                 265                 270

Leu Ala Leu Gly Gln Gly Lys Asp Val Asp Thr Ala Gln Gln Asp Ile
            275                 280                 285

Gly Gln Val Val Glu Gly Tyr Arg Asn Thr Lys Glu Val Trp Leu Leu
            290                 295                 300

Ala Gln Arg Met Gly Val Glu Met Pro Ile Val Glu Gln Ile Tyr Gln
305                 310                 315                 320

Val Leu Tyr Gln Gly Lys Asp Ala Arg Met Ala Ala Gln Asp Leu Leu
                325                 330                 335

Ala Arg Asp Lys Lys Ala Glu Arg
            340
```

<210> SEQ ID NO 30
<211> LENGTH: 284
<212> TYPE: PRT
<213> ORGANISM: Vibrio furnisii

<400> SEQUENCE: 30

```
Val Val Cys Ala Phe Val Asn Asp Asp Leu Ser Ala Thr Val Leu Glu
1               5                   10                  15

Glu Leu Tyr Gln Gly Gly Thr Arg Leu Ile Ala Met Arg Cys Ala Gly
            20                  25                  30

Phe Asp Lys Val Asp Leu Asp Ala Ala Lys Arg Ile Gly Met Gln Val
            35                  40                  45

Val Arg Val Pro Ala Tyr Ser Pro Glu Ala Val Ala Glu His Ala Val
        50                  55                  60

Gly Leu Met Met Cys Leu Asn Arg Arg Tyr His Lys Ala Tyr Gln Arg
65                  70                  75                  80

Thr Arg Glu Ala Asn Phe Ser Leu Glu Gly Leu Val Gly Phe Asn Phe
                85                  90                  95

Tyr Gly Lys Thr Val Gly Val Ile Gly Ser Gly Lys Ile Gly Ile Ala
            100                 105                 110

Ala Met Arg Ile Leu Lys Gly Leu Gly Met Asn Ile Leu Cys Phe Asp
            115                 120                 125

Pro Tyr Glu Asn Pro Leu Ala Ile Glu Ile Gly Ala Lys Tyr Val Gln
            130                 135                 140

Leu Pro Glu Leu Tyr Ala Asn Ser Asp Ile Ile Thr Leu His Cys Pro
145                 150                 155                 160

Met Thr Lys Glu Asn Tyr His Leu Leu Asp Glu Gln Ala Phe Ala Gln
                165                 170                 175

Met Lys Asp Gly Val Met Ile Ile Asn Thr Ser Arg Gly Glu Leu Leu
            180                 185                 190

Asp Ser Val Ala Ala Ile Glu Ala Leu Lys Arg Gly Arg Ile Gly Ala
            195                 200                 205

Leu Gly Leu Asp Val Tyr Asp Asn Glu Lys Asp Leu Phe Phe Gln Asp
            210                 215                 220

Lys Ser Asn Asp Val Ile Val Asp Asp Val Phe Arg Arg Leu Ser Ala
225                 230                 235                 240

Cys His Asn Val Leu Phe Thr Gly His Gln Ala Phe Leu Thr Glu Asp
```

```
                        245                 250                 255
Ala Leu His Asn Ile Ala Gln Thr Thr Leu Asn Asn Val Leu Ala Phe
            260                 265                 270

Glu Gln Gly Thr Lys Ser Gly Asn Glu Leu Val Asn
        275                 280

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tcatatgcgc ccattacatc cg                                            22

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tcctaggagg gctaatttag ccctttagtt                                    30
```

PRODUCTION OF FATTY ACIDS AND DERIVATIVES THEREOF

CROSS-REFERENCE TO RELATED APPLICATIONS

This application is a continuation of U.S. patent application Ser. No. 13/870,426, filed Apr. 25, 2013, which is a continuation of copending U.S. patent application Ser. No. 13/302,957, filed Nov. 22, 2011, which is a continuation of copending U.S. patent application Ser. No. 12/278,957, filed Apr. 20, 2010, as the U.S. national phase of Patent Cooperation Treaty Application No. PCT/US2007/11923, filed May 18, 2007, which claims benefit to U.S. Provisional Application Nos. 60/908,547 filed Mar. 28, 2007; U.S. Provisional Application No. 60/801,995 filed May 19, 2006, and U.S. Provisional Application No. 60/802,016 fled May 19, 2006, and, all of which are herein incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 80,354 Byte ASCII (Text) file named "PCT_SeqLstgAs-Filed_05.18.07" created on May 18, 2007. It is understood that the Patent and Trademark Office will make the necessary changes in application number and filing date for the instant application.

FIELD

Compositions and methods for production of fatty alcohols using recombinant microorganisms e are provided as well as fatty alcohol compositions produced by such methods.

BACKGROUND

Developments in technology have been accompanied by an increased reliance on fuel sources and such fuel sources are becoming increasingly limited and difficult to acquire. With the burning of fossil fuels taking place at an unprecedented rate, it has likely that the world's fuel demand will soon outweigh the current fuel supplies.

As a result, efforts have been directed toward harnessing sources of renewable energy, such as sunlight, water, wind, and biomass. The use of biomasses to produce new sources of fuel which are not derived from petroleum sources, (i.e. biofuel) has emerged as one alternative option. Biofuel (biodiesel) is a biodegradable, clean-burning combustible fuel made of long chain alkanes and esters, Biodiesel can be used in most internal combustion diesel engines in either a pure form, which is referred to as "neat" biodiesel, or as a mix in any concentration with regular petroleum diesel. Current methods of making biodiesel involve transesterification of triacylglycerides (mainly vegetable oil) which leads to a mixture of fatty acid esters and the unwanted side product glycerin, thus, providing a product that is heterogeneous and a waste product that causes economic inefficiencies.

SUMMARY

Disclosed herein are recombinant microorganisms that are capable of synthesizing products derived from the fatty acid biosynthetic pathway (fatty alcohols), and optionally releasing such products into the fermentation broth. Such fatty alcohols are useful, inter alio, specialty chemicals. These specialty chemicals can be used to make additional products, such as nutritional supplements, polymers, paraffin replacements, and personal care products.

The recombinant microorganisms disclosed herein can be engineered to yield various fatty alcohol compositions.

In one example, the disclosure provides a method for modifying a microorganism so that it produces, and optionally releases, fatty alcohols generated from a renewable carbon source. Such microorganisms are genetically engineered, for example, by introducing an exogenous DNA sequence encoding one or more proteins capable of metabolizing a renewable carbon source to produce, and in some examples secrete, a fatty alcohol composition. The modified microorganisms can then be used in a fermentation process to produce useful fatty alcohols using the renewable carbon source (biomass) as a starting material. In some examples, an existing genetically tractable microorganism is used because of the ease of engineering its pathways for controlling growth, production and reducing or eliminating side reactions that reduce biosynthetic pathway efficiencies.

Provided herein are microorganisms that produce fatty alcohols having defined carbon chain length, branching, and saturation levels. In particular examples, the production of homogeneous products decreases the overall cost associated with fermentation and separation Microorganisms expressing one or more exogenous nucleic acid sequences encoding at least one thioesterase (EC 3.1.2.14) and at least one fatty alcohol forming acyl-CoA reductase (1.1.1.*) are provided. The thioesterase peptides encoded by the exogenous nucleic acid sequences can be chosen to provide homogeneous products.

In some examples the microorganism that is engineered to produce the fatty acid derivative is *E. coli, Z. mobilis, Rhodococcus opacus, Ralstonia eutropha, Saccharomyces cerevisiae, Lactococcus lochs, Streptomycetes, Stenotrophomonas maltophila, Pseudomonas* or *Micrococus leuteus* and their relatives.

In addition to being engineered to express exogenous nucleic acid sequences that allow for the production of fatty alcohols, the microorganism can additionally have one or more endogenous genes functionally deleted or attenuated.

In addition to being engineered to express exogenous nucleic acid sequences that allow for the production of fatty alcohols, the microorganism can additionally have one or more additional genes over-expressed.

In some examples, the microorganisms described herein produce at least 1 mg of fatty alcohol per liter fermentation broth. In other examples the microorganisms produce at least 100 mg/L, 500 mg/L, 1 g/L, 5 g/L, 10 g/L, 20 g/L, 25 g/L, 30 g/L, 35 g/L, 40 g/L, 50 g/L, 100 g/L, or 120 g/L of fatty alcohol per liter fermentation broth. In some examples, the fatty alcohol is produced and released from the microorganism and in yet other examples the microorganism is lysed prior to separation of the product.

In some examples, the fatty alcohol includes a carbon chain that is at least 8, 10, 12, 14, 16, 18, 20, 22, 24, 26, 28, 30, 32, or 34 carbons long. In some examples at least 50%, 60%, 70%, 80%, 85%, 90%, or 95% of the fatty alcohol product made contains a carbon chain that is 8, 10, 12, 14, 16, 18, 20, 22, 24, 26, 28, 30, 32, or 34 carbons long. In yet other examples, at least 60%, 70%, 80%, 85%, 90%, or 95% of the fatty alcohol product contain 1, 2, 3, 4, or 5, points of unsaturation Also provided are methods of producing alcohol. These methods include culturing the microorganisms described herein and separating the product from the fermentation broth.

These and other examples are described further in the following detailed description.

BRIEF DESCRIPTION OF THE FIGURES

FIGS. 7A-7D show GS-MS spectrum of octyl octanoate (C8C8) produced by a production hosts expressing alcohol acetyl transferase (AATs, EC 2.3.1.84) and production hosts expressing wax synthase (EC 2.3.1.75). FIG. 7A shows acetyl acetate extract of strain C41(DE3, ΔfadE/pHZ1.43)/pRSET B+pAS004.114B) wherein the pHZ1.43 plasmid expressed ADP1 (wax synthase). FIG. 7B shows acetyl acetate extract of strain C41(DE3, ΔfadE/pHZ1.43)/pRSET B+FpAS004.114B) wherein the pHZ1.43 plasmid expressed SAAT. FIG. 7C shows acetyl acetate extract of strain C41 (DE3, ΔfadE/pHZ1.43)/pRSET B+pAS004.114B) wherein the pHZ1.43 plasmid did not contain ADP1 (wax synthase) or SAAT. FIG. 7D shows the mass spectrum and fragmentation pattern of C8C8 produced by C41(DE3, ΔfadE/pHZ1.43)/pRSET B+pAS004.114B) wherein the pHZ1.43 plasmid expressed SAAT).

FIG. 9A shows a chromatogram of the ethyl extract of the culture of *E. coli* LS9001 strain transformed with plasmids pCDFDuet-1-fadD-WSadp1, pETDuet-1-'tesA. Ethanol was fed to fermentations. FIG. 9B shows a chromatogram of ethyl hexadecanoate and ethyl oleate used as reference.

FIG. 10 shows a table that identifies various genes that can be over-expressed or attenuated to increase fatty acid derivative production. The table also identifies various genes that can be modulated to alter the structure of the fatty acid derivative product. One of ordinary skill in the art will appreciate that some of the genes that are used to alter the structure of the fatty acid derivative will also increase the production of fatty acid derivatives.

ABBREVIATIONS AND TERMS

Figure 1:
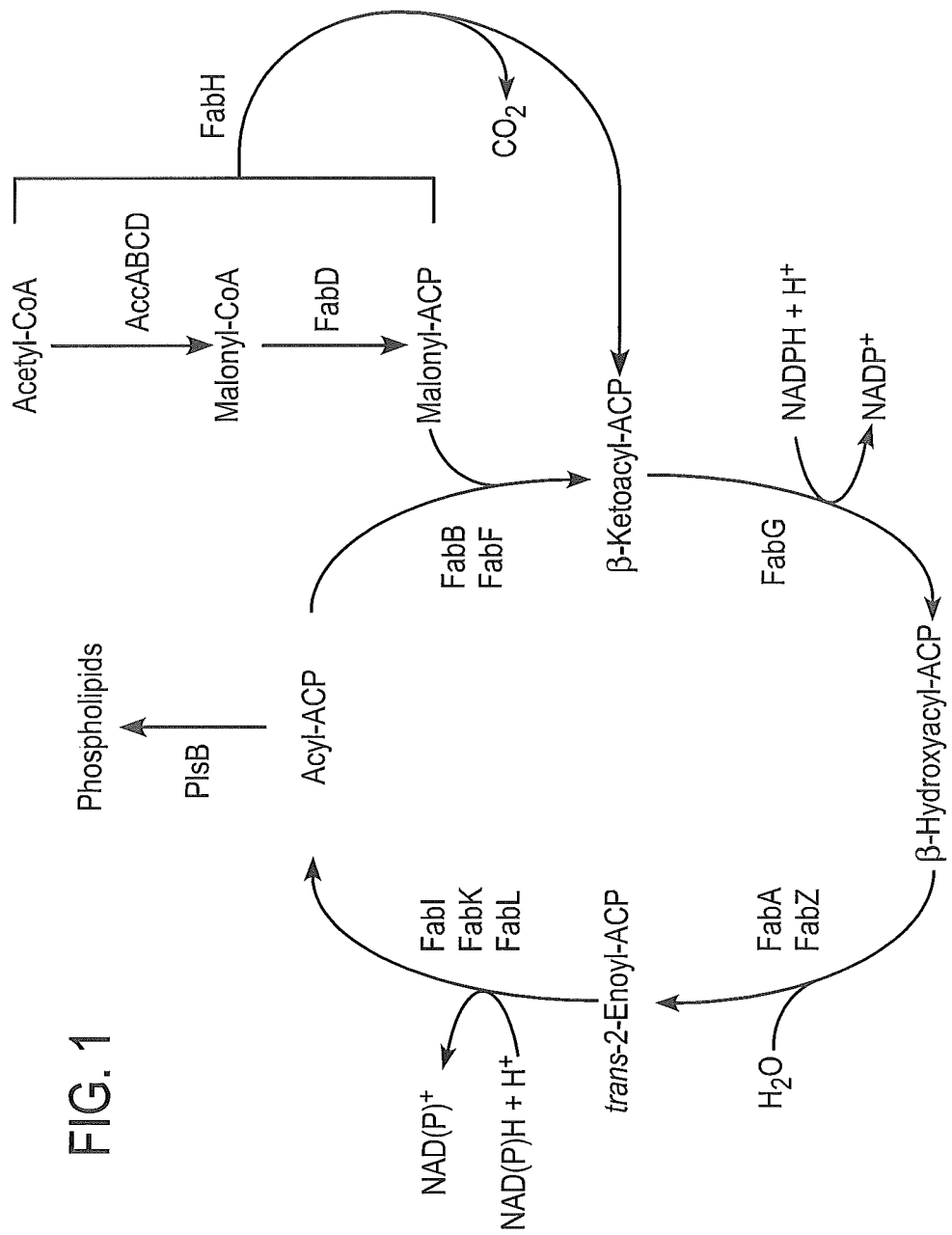
FIG. 1 shows the FAS biosynthetic pathway.

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a cell" includes one or a plurality of such cells, and reference to "comprising the thioesterase" includes reference to one or more thioesterase peptides and equivalents thereof known to those of ordinary skill in the art, and so forth. The term "or" refers to a single element of stated alternative elements or a combination of two or more elements, unless the context clearly indicates otherwise. For example, the phrase "thioesterase activity or fatty alcohol-forming acyl-CoA reductase activity" refers to thioesterase activity, fatty alcohol forming acyl-CoA reductase activity, or a combination of both fatty alcohol forming acyl-CoA reductase activity, and thioesterase activity.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Accession Numbers: The accession numbers throughout this description are derived from the NCBI database (National Center for Biotechnology Information) maintained by the National Institute of Health, U.S.A. The accession numbers are as provided in the database on Mar. 27, 2007.

Enzyme Classification Numbers (EC): The EC numbers provided throughout this description are derived from the KEGG Ligand database, maintained by the Kyoto Encyclopedia of Genes and Genomics, sponsored in part by the University of Tokyo. The EC numbers are as provided in the database on Mar. 27, 2007.

Attenuate: To lessen the impact, activity or strength of something. In one example, the sensitivity of a particular enzyme to feedback inhibition or inhibition caused by a composition that is not a product or a reactant (non-pathway specific feedback) is lessened such that the enzyme activity is not impacted by the presence of a compound. For example, the fabH gene and its corresponding amino acid sequence are temperature sensitive and can be altered to decrease the sensitivity to temperature fluctuations. The attenuation of the fabH gene can be used when branched amino acids are desired. In another example, an enzyme that has been altered to be less active can be referred to as attenuated.

A functional deletion of an enzyme can be used to attenuate an enzyme. A functional deletion is a mutation, partial or complete deletion, insertion, or other variation made to a gene sequence or a sequence controlling the transcription of a gene sequence, which reduces or inhibits production of the gene product, or renders the gene product non-functional (i.e. the mutation described herein for the plsB gene). For example, functional deletion of fabR in *E. coli* reduces the repression of the fatty acid biosynthetic pathway and allows *E. coli* to produce more unsaturated fatty acids (UFAs). In some instances a functional deletion is described as a knock-out mutation.

One of ordinary skill in the art will appreciate that there are many methods of attenuating enzyme activity. For example, attenuation can be accomplished by introducing amino acid sequence changes via altering the nucleic acid sequence, placing the gene under the control of a less active promoter, expressing interfering RNA, ribozymes or antisense sequences that targeting the gene of interest, or through any other technique known in the art.

Carbon source: Generally refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, etc. These include, for example, various monosaccharides such as glucose, oligosaccharides, polysaccharides, cellulosic material, xylose, and arabinose, disaccharides, such sucrose, saturated or unsaturated fatty acids, succinate, lactate, acetate, ethanol, etc., or mixtures thereof. The carbon source can additionally be a product of photosynthesis, including, but not limited to glucose.

cDNA (complementary DNA): A piece of DNA lacking internal, non-coding segments (introns) and regulatory sequences which determine transcription. cDNA can be synthesized by reverse transcription from messenger RNA extracted from cells.

Deletion: The removal of one or more nucleotides from a nucleic acid molecule or one or more amino acids from a protein, the regions on either side being joined together.

Detectable: Capable of having an existence or presence ascertained. For example, production of a product from a reactant, for example, the production of C18 fatty acids, is detectable using the method provided in Example 11 below.

DNA: Deoxyribonucleic acid. DNA is a long chain polymer which includes the genetic material of most living organisms (some viruses have genes including ribonucleic acid, RNA). The repeating units in DNA polymers are four different nucleotides, each of which includes one of the four bases, adenine, guanine, cytosine and thymine bound to a deoxyribose sugar to which a phosphate group is attached. Triplets of nucleotides, referred to as codons, in DNA molecules code for amino acid in a peptide. The term codon is also used for the corresponding (and complementary) sequences of three nucleotides in the mRNA into which the DNA sequence is transcribed.

Endogenous: As used herein with reference to a nucleic acid molecule and a particular cell or microorganism refers to a nucleic acid sequence or peptide that is in the cell and was not introduced into the cell using recombinant engineering techniques. For example, a gene that was present in the cell when the cell was originally isolated from nature. A gene is still considered endogenous if the control sequences, such as a promoter or enhancer sequences that activate transcription or translation have been altered through recombinant techniques.

Exogenous: As used herein with reference to a nucleic acid molecule and a particular cell refers to any nucleic acid molecule that does not originate from that particular cell as found in nature. Thus, a non-naturally-occurring nucleic acid molecule is considered to be exogenous to a cell once introduced into the cell. A nucleic acid molecule that is naturally-occurring also can be exogenous to a particular cell. For example, an entire coding sequence isolated from cell X is an exogenous nucleic acid with respect to cell Y once that coding sequence is introduced into cell Y, even if X and Y are the same cell type.

Expression: The process by which a gene's coded information is converted into the structures and functions of a cell, such as a protein, transfer RNA, or ribosomal RNA. Expressed genes include those that are transcribed into mRNA and then translated into protein and those that are transcribed into RNA but not translated into protein (for example, transfer and ribosomal RNAs).

Fatty ester: Includes any ester made from a fatty acid. The carbon chains in fatty acids can contain any combination of the modifications described herein. For example, the carbon chain can contain one or more points of unsaturation, one or more points of branching, including cyclic branching, and can be engineered to be short or long. Any alcohol can be used to form fatty acid esters, for example alcohols derived from the fatty acid biosynthetic pathway, alcohols produced by the production host through non-fatty acid biosynthetic pathways, and alcohols that are supplied in the fermentation broth.

Fatty acid derivative: Includes products made in part from the fatty acid biosynthetic pathway of the host organism. The fatty acid biosynthetic pathway includes fatty acid synthase enzymes which can be engineered as described herein to produce fatty acid derivatives, and in some examples can be expressed with additional enzymes to produce fatty acid derivatives having desired carbon chain characteristics. Exemplary fatty acid derivatives include for example, short and long chain alcohols, hydrocarbons, and fatty acid esters including waxes.

Fermentation Broth: Includes any medium which supports microorganism life (i.e. a microorganism that is actively metabolizing carbon). A fermentation medium usually contains a carbon source. The carbon source can be anything that can be utilized, with or without additional enzymes, by the microorganism for energy.

Hydrocarbon: includes chemical compounds that containing the elements carbon (C) and hydrogen (H). All hydrocarbons consist of a carbon backbone and atoms of hydrogen attached to that backbone. Sometimes, the term is used as a shortened form of the term "aliphatic hydrocarbon." There are essentially three types of hydrocarbons: (1) aromatic hydrocarbons, which have at least one aromatic ring; (2) saturated hydrocarbons, also known as alkanes, which lack double, triple or aromatic bonds; and (3) unsaturated hydrocarbons, which have one or more double or triple bonds between carbon atoms, are divided into: alkenes, alkynes, and dienes. Liquid geologically-extracted hydrocarbons are referred to as petroleum (literally "rock oil") or mineral oil, while gaseous geologic hydrocarbons are referred to as natural gas. All are significant sources of fuel and raw materials as a feedstock for the production of organic chemicals and are commonly found in the Earth's subsurface using the tools of petroleum geology. Oil reserves in sedimentary rocks are the principal source of hydrocarbons for the energy and chemicals industries. Hydrocarbons are of prime economic importance because they encompass the constituents of the major fossil fuels (coal, petroleum, natural gas, etc.) and biofuels, as well as plastics, waxes, solvents and oils.

Isolated: An "isolated" biological component (such as a nucleic acid molecule, protein, or cell) has been substantially separated or purified away from other biological components in which the component naturally occurs, such as other chromosomal and extrachromosomal DNA and RNA, and proteins. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

In one example, isolated refers to a naturally-occurring nucleic acid molecule that is not immediately contiguous with both of the sequences with which it is immediately contiguous (one on the 5' end and one on the 3' end) in the naturally-occurring genome of the organism from which it is derived.

Microorganism: Includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

Nucleic Acid Molecule: Encompasses both RNA and DNA molecules including, without limitation, cDNA, genomic DNA, and mRNA. Includes synthetic nucleic acid molecules, such as those that are chemically synthesized or recombinantly produced. The nucleic acid molecule can be double-stranded or single-stranded. Where single-stranded, the nucleic acid molecule can be the sense strand or the antisense strand. In addition, nucleic acid molecule can be circular or linear.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame. Configurations of separate genes that are transcribed in tandem as a single messenger RNA are denoted as operons. Thus placing genes in close proximity, far example in a plasmid vector, under the transcriptional regulation of a single promoter, constitutes a synthetic operon.

ORF (open reading frame): A series of nucleotide triplets (codons) coding for amino acids without any termination codons. These sequences are usually translatable into a peptide.

Over-expressed: When a gene is caused to be transcribed at an elevated rate compared to the endogenous transcription rate for that gene. In some examples, over-expression additionally includes an elevated rate of translation of the gene compared to the endogenous translation rate for that gene. Methods of testing for over-expression are well known in the art, for example transcribed RNA levels can be assessed using rtPCR and protein levels can be assessed using SDS page gel analysis.

Purified: The term purified does not require absolute purity; rather, it is intended as a relative term. Thus, for example, a purified fatty acid derivative preparation, such as a wax, or a fatty acid ester preparation, is one in which the product is more concentrated than the product is in its environment within a cell. For example, a purified wax is one that is substantially separated from cellular components (nucleic acids, lipids, carbohydrates, and other peptides) that can accompany it. In another example, a purified wax preparation is one in which the wax is substantially-free from contaminants, such as those that might be present following fermentation.

In one example, a fatty acid ester is purified when at least about 50% by weight of a sample is composed of the fatly acid ester, for example when at least about 60%, 70%, 80%, 85%, 90%, 92%, 95%, 98%, or 99% or more of a sample is composed of the fatty acid ester. Examples of methods that can be used to purify a waxes, fatty alcohols, and fatty acid esters, include the methods described in Example 11 below.

Recombinant: A recombinant nucleic acid molecule or protein is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or proteins, such as genetic engineering techniques. Recombinant is also used to describe nucleic acid molecules that have been artificially manipulated, but contain the same regulatory sequences and coding regions that are found in the organism from which the nucleic acid was isolated. A recombinant cell or microorganism is one that contains an exogenous nucleic acid molecule, such as a recombinant nucleic acid molecule.

Release: The movement of a compound from inside a cell (intracellular) to outside a cell (extracellular). The movement can be active or passive. When release is active it can be facilitated by one or more transporter peptides and in some examples it can consume energy. When release is passive, it can be through diffusion through the membrane and can be facilitated by continually collecting the desired compound from the extracellular environment, thus promoting further diffusion. Release of a compound can also be accomplished by lysing a cell.

Surfactants: Substances capable of reducing the surface tension of a liquid in which they are dissolved. They are typically composed of a water-soluble head and a hydrocarbon chain or tail. The water soluble group is hydrophilic and can be either ionic or nonionic, and the hydrocarbon chain is hydrophobic. Surfactants are used in a variety of products, including detergents and cleaners, and are also used as auxiliaries for textiles, leather and paper, in chemical processes, in cosmetics and pharmaceuticals, in the food industry and in agriculture. In addition, they can be used to aid in the extraction and isolation of crude oils which are found hard to access environments or as water emulsions.

There are four types of surfactants characterized by varying uses. Anionic surfactants have detergent-like activity and are generally used for cleaning applications. Cationic surfactants contain long chain hydrocarbons and are often used to treat proteins and synthetic polymers or are components of fabric softeners and hair conditioners. Amphoteric surfactants also contain long chain hydrocarbons and are typically used in shampoos. Non-ionic surfactants are generally used in cleaning products.

Transformed or recombinant cell: A cell into which a nucleic acid molecule has been introduced, such as an acyl-CoA synthase encoding nucleic acid molecule, for example by molecular biology techniques. Transformation encompasses all techniques by which a nucleic acid molecule can be introduced into such a cell, including, but not limited to, transfection with viral vectors, conjugation, transformation with plasmid vectors, and introduction of naked DNA by electroporation, lipofection, and particle gun acceleration.

Under conditions that permit product production: Any fermentation conditions that allow a microorganism to produce a desired product, such as fatty acids, hydrocarbons, fatty alcohols, waxes, or fatty acid esters. Fermentation conditions usually include temperature ranges, levels of aeration, and media selection, which when combined allow the microorganism to grow. Exemplary mediums include broths or gels. Generally, the medium includes a carbon source such as glucose, fructose, cellulose, or the like that can be metabolized by the microorganism directly, or enzymes can be used in the medium to facilitate metabolizing the carbon source. To determine if culture conditions permit product production, the microorganism can be cultured for 24, 36, or 48 hours and a sample can be obtained and analyzed. For example, the cells in the sample or the medium in which the cells were grown can be tested for the presence of the desired product. When testing for the presence of a product assays, such as those provided in the Examples below, can be used.

Vector: A nucleic acid molecule as introduced into a cell, thereby producing a transformed cell. A vector can include nucleic acid sequences that permit it to replicate in the cell, such as an origin of replication. A vector can also include one or more selectable marker genes and other genetic elements known in the alt.

Wax: A variety of fatty acid esters which form solids or pliable substances under an identified set of physical conditions. Fatty acid esters that are termed waxes generally have longer carbon chains than fatty acid esters that are not waxes. For example, a wax generally forms a pliable substance at room temperature.

DETAILED DESCRIPTION

I. Production of Fatty Acid Derivatives

The host organism that exogenous DNA sequences are transformed into can be a modified host organism, such as an organism that has been modified to increase the production of acyl-ACP or acyl-CoA, reduce the catabolism of fatty acid derivatives and intermediates, or to reduce feedback inhibition at specific points in the biosynthetic pathway. In addition to modifying the genes described herein additional cellular resources can be diverted to over produce fatty acids, for example the lactate, succinate and/or acetate pathways can be attenuated, and acetyl-CoA carboxylase (ACC) can be over expressed. The modifications to the production host described herein can be through genomic alterations, extrachromosomal expression systems, or combinations thereof. An overview of the pathway is provided in FIGS. 1 and 2.

A. Acetyl-CoA-Malonyl-CoA to Acyl-ACP

Fatty acid synthase (FAS) is a group of peptides that catalyze the initiation and elongation of acyl chains (Marrakchi et al., *Biochemical Society*, 30:1050-1055, 2002). The acyl carrier protein (ACP) along with the enzymes in the FAS pathway control the length, degree of saturation and branching of the fatty acids produced. Enzymes that can be included in FAS include AccABCD, FabD, FabH, FabG, FabA, FabZ, FabI, FabK, FabL, FabM, FabB, and FabF. Depending upon the desired product one or more of these genes can be attenuated or over-expressed.

For example, the fatty acid biosynthetic pathway in the production host uses the precursors acetyl-CoA and malonyl-CoA (FIG. 2). *E. coli* or other host organisms engineered to overproduce these components can serve as the starting point for subsequent genetic engineering steps to provide the specific output product (such as, fatty acid esters, hydrocarbons, fatty alcohols). Several different modifications can be made, either in combination or individually, to the host strain to obtain increased acetyl CoA/malonyl CoA/fatty acid and fatty acid derivative production. For example, to increase acetyl CoA production, a plasmid with pdh, panK, aceEF, (encoding the E1p dehydrogenase component and the E2p dihydrolipoamide acyltransferase component of the pyruvate and 2-oxoglutarate dehydrogenase complexes), fAbH/fabD/fabG/acpP/fabF, and in some examples additional DNA encoding fatty-acyl-CoA reductases and aldehyde decarbonylases, all under the control of a constitutive, or otherwise controllable promoter, can be constructed. Exemplary Genbank accession numbers for these genes are: pdh (BAB34380, AAC73227, AAC73226), panK (also known as coaA, AAC76952), aceEF (AAC73227, AAC73226), fabH (AAC74175), fabD (AAC74176), AbG (AAC74177), acpP (AAC74178), fAbF (AAC74179).

Additionally, fadE, gpsA, ldhA, pflb, adhE, pta, poxB, ackA, and/or ackB can be knocked-out, or their expression levels can be reduced, in the engineered microorganism by transformation with conditionally replicative or non-replicative plasmids containing null or deletion mutations of the corresponding genes, or by substituting promoter or enhancer sequences. Exemplary Genbank accession numbers for these genes are; fadE (AAC73325), gspA (AAC76632), kihA (AAC74462), pflb (AAC73989), adhE (AAC74323), pta (AAC75357), poxB (AAC73958), ackA (AAC75356), and ackB (BAB81430).

The resulting engineered microorganisms can be grown in a desired environment, for example one with limited glycerol (less than 1% w/v in the culture medium). As such, these microorganisms will have increased acetyl-CoA production levels. Malonyl-CoA overproduction can be effected by engineering the microorganism as described above, with DNA encoding accABCD (acetyl CoA carboxylase, for example accession number AAC73296, EC 6.4.1.2) included in the plasmid synthesized de novo. Fatty acid overproduction can be achieved by further including DNA encoding lipase (for example Accessions numbers CAA89087, CAA98876) in the plasmid synthesized de nova In some examples, acetyl-CoA carboxylase (ACC) is over-expressed to increase the intracellular concentration thereof by at least 2-fold, such as at least 5-fold, or at least 10-fold, for example relative to native expression levels.

In addition, the plsB (for example Accession number AAC77011) D311E mutation can be used to remove limitations on the pool of acyl-CoA.

In addition, over-expression of an sfa gene (suppressor of FabA, for example Accession number AAN79592) can be included in the production host to increase production of monounsaturated fatty acids (Rock et al., *J. Bacteriology* 178:5382-5387, 1996).

B. Acyl-ACP to Fatty Acid

To engineer a production host for the production of a homogeneous population of fatty acid derivatives, one or more endogenous genes can be attenuated or functionally deleted and one or more thioesterases can be expressed. For example, C10 fatty acid derivatives can be produced by attenuating thioesterase C18 (for example accession numbers AAC73596 and P0ADA1), which uses C18:1-ACP and expressing thioesterase C10 (for example accession number Q39513), which uses C10-ACP. Thus, resulting in a relatively homogeneous population of fatty acid derivatives that have a carbon chain length of 10. In another example, C14 fatty acid derivatives can be produced by attenuating endogenous thioesterases that produce non-C14 fatty acids and expressing the thioesterase accession number Q39473 (which uses C14-ACP). In yet another example, C12 fatty acid derivatives can be produced by expressing thioesterases that use C12-ACP (for example accession number Q41635) and attenuating thioesterases that produce non-C12 fatty acids. Acetyl CoA, malonyl CoA, and fatty acid overproduction can be verified using methods known in the art, for example by using radioactive precursors, HPLC, and GC-MS subsequent to cell lysis.

TABLE 1

Thioesterases

| Accession Number | Source Organism | Gene | Preferential product produced |
|---|---|---|---|
| AAC73596 | E. coli | tesA without leader sequence | C18:1 |
| Q41635 | Umbellularia california | fatB | C12:0 |
| Q39513; | Cuphea hookeriana | fatB2 | C8:0-C10:0 |
| AAC49269 | Cuphea hookeriana | fatB3 | C14:0-C16:0 |
| Q39473 | Cinnamonum camphorum | fatB | C14:0 |
| CAA85388 | Arabidopsis thaliana | fatB[M141T]* | C16:1 |
| NP 189147; NP 193041 | Arabidopsis thaliana | fatA | C18:1 |
| CAC39106 | Bradyrhiizobium japonicum | fatA | C18:1 |
| AAC72883 | Cuphea hookeriana | fatA | C18:1 |

*Mayer et al., *BMC Plant Biology* 7: 1-11, 2007

C. Fatty Acid to Acyl-CoA

Production hosts can be engineered using known peptides to produce fatty acids of various lengths. One method of making fatty acids involves increasing the expression of, or expressing more active forms of, one or more acyl-CoA synthase peptides (EC 2.3.1.86).

As used herein, acyl-CoA synthase includes peptides in enzyme classification number EC 2.3.1.86, as well as any other peptide capable of catalyzing the conversion of a fatty acid to acyl-CoA. Additionally, one of ordinary skill in the art will appreciate that some acyl-CoA synthase peptides will catalyze other reactions as well, for example some acyl-CoA synthase peptides will accept other substrates in addition to fatty acids. Such non-specific acyl-CoA synthase peptides are, therefore, also included. Acyl-CoA synthase peptide sequences are publicly available. Exemplary GenBank Accession Numbers are provided in FIG. 10.

D. Acyl-CoA to Fatty Alcohol

Production hosts can be engineered using known polypeptides to produce fatty alcohols from acyl-CoA. One method of making fatty alcohols involves increasing the expression of or expressing more active forms of fatty alcohol forming acyl-CoA reductase (FAR, EC 1.1.1.1, or acyl-CoA reductases (EC 1.2.1.50) and alcohol dehydrogenase (EC 1.1.1.1). Hereinafter fatty alcohol forming acyl-CoA reductase (FAR, EC 1.1.1.*), acyl-CoA reductases (EC 1.2.1.50) and alcohol dehydrogenase (EC 1.1.1.1) are collectively referred to as fatty alcohol forming peptides. In some examples all three of the fatty alcohol forming genes can be over expressed in a production host, and in yet other examples one or more of the fatty alcohol forming genes can be over-expressed.

As used herein, fatty alcohol forming peptides include peptides in enzyme classification numbers EC 1.1.1.*, 1.2.1.50, and 1.1.1.1, as well as any other peptide capable of catalyzing the conversion of acyl-CoA to fatty alcohol. Additionally, one of ordinary skill in the art will appreciate that some fatty alcohol forming peptides will catalyze other reactions as well, for example some acyl-CoA reductase peptides will accept other substrates in addition to fatty acids. Such non-specific peptides are, therefore, also included. Fatty alcohol forming peptides sequences are publicly available. Exemplary GenBank Accession Numbers are provided in FIG. 10.

Fatty alcohols can also be described as hydrocarbon-based surfactants. For surfactant production the microorganism is modified so that it produces a surfactant from a renewable carbon source. Such a microorganism includes a first exogenous DNA sequence encoding a protein capable of converting a fatty acid to a fatty aldehyde and a second exogenous DNA sequence encoding a protein capable of converting a fatty aldehyde to an alcohol. In some examples, the first exogenous DNA sequence encodes a fatty acid reductase. In one embodiment, the second exogenous DNA sequence encodes mammalian microsomal aldehyde reductase or long-chain aldehyde dehydrogenase. In a further example, the first and second exogenous DNA sequences are from a multienzyme complex from *Arthrobacter* AK 19, *Rhodotorula glutinins, Acinobacter* sp strain M-1, or *Candida lipolytica*. In one embodiment, the first and second heterologous DNA sequences are from a multienzyme complex from *Acinobacter* sp strain M-1 or *Candida lipolytica*.

Additional sources of heterologous DNA sequences encoding fatty acid to long chain alcohol converting proteins that can be used in surfactant production include, but are not limited to, *Mortierella alpina* (ATCC 32222), *Crytococcus curvatus*, (also referred to as *Apiotricum curvatum*), *Alcanivorax jadensis* (T9T=DSM 12718=ATCC 700854), *Acinetobacter* sp. HO1-N, (ATCC 14987) and *Rhodococcus opacus* (PD630 DSMZ 44193).

In one example, the fatty acid derivative is a saturated or unsaturated surfactant product having a carbon atom content limited to between 6 and 36 carbon atoms. In another example, the surfactant product has a carbon atom content limited to between 24 and 32 carbon atoms.

Appropriate hosts for producing surfactants can be either eukaryotic or prokaryotic microorganisms. Exemplary hosts include *Arthrobacter* AK 19, *Rhodotorula glutinins, Acinobacter* sp strain M-1, *Arabidopsis thalania*, or *Candida lipolytica, Saccharomyces cerevisiae*, and *E. coli* engineered to express acetyl CoA carboxylase. Hosts which demonstrate an innate ability to synthesize high levels of surfactant precursors in the form of lipids and oils, such as *Rhodococcus opacus, Arthrobacter* AK 19, *Rhodotorula glutinins E.*

*coli* engineered to express acetyl CoA carboxylase, and other oleaginous bacteria, yeast, and fungi can also be used.

E. Fatty Alcohols to Fatty Esters

Production hosts can be engineered using known polypeptides to produce fatty esters of various lengths. One method of making fatty esters includes increasing the expression of, or expressing more active forms of, one or more alcohol O-acetyltransferase peptides (EC 2.3.1.84). These peptides catalyze the reaction of acetyl-CoA and an alcohol to form CoA and an acetic ester. In some examples the alcohol O-acetyltransferase peptides can be expressed in conjunction with selected thioesterase peptides, FAS peptides and fatty alcohol forming peptides, thus, allowing the carbon chain length, saturation and degree of branching to be controlled. In some cases the bkd operon can be coexpressed to enable branched fatty acid precursors to be produced.

As used herein, alcohol O-acetyltransferase peptides include peptides in enzyme classification number EC 2.3.1.84, as well as any other peptide capable of catalyzing the conversion of acetyl-CoA and an alcohol to form CoA and an acetic ester. Additionally, one of ordinary skill in the art will appreciate that alcohol O-acetyltransferase peptides will catalyze other reactions as well, for example some alcohol O-acetyltransferase peptides will accept other substrates in addition to fatty alcohols or acetyl-CoA thioester i.e., such as other alcohols and other acyl-CoA thioesters. Such non-specific or divergent specificity alcohol O-acetyltransferase peptides are, therefore, also included. Alcohol O-acetyltransferase peptide sequences are publicly available. Exemplary Gen Bank Accession Numbers are provided in FIG. 10. Assays for characterizing the activity of a particular alcohol O-acetyltransferase peptides are well known in the art. Engineered O-acetyltransferases and O-acyltransferases can be also created that have new activities and specificities for the donor acyl group or acceptor alcohol moiety. Engineered enzymes could be generated through rational and evolutionary approaches well documented in the art.

F. Acyl-CoA to Fatty Esters (Biodiesels and Waxes)

Production hosts can be engineered using known peptides to produce fatty acid esters From acyl-CoA and alcohols. In some examples the alcohols are provided in the fermentation media and in other examples the production host can provide the alcohol as described herein. One of ordinary skill in the art will appreciate that structurally, fatty acid esters have an A and a B side. As described herein, the A side of the ester is used to describe the carbon chain contributed by the alcohol, and the B side of the ester is used to describe the carbon chain contributed by the acyl-CoA. Either chain can be saturated or unsaturated, branched or unbranched. The production host can be engineered to produce fatty alcohols or short chain alcohols. The production host can also be engineered to produce specific acyl-CoA molecules. As used herein fatty acid esters are esters derived from a fatty acyl-thioester and an alcohol, wherein the A side and the B side of the ester can vary in length independently. Generally, the A side of the ester is at least 1, 2, 3, 4, 5, 6, 7, or 8 carbons in length, while the B side of the ester is 8, 10, 12, 14, 16, 18, 20, 22, 24, or 26 carbons in length. The A side and the B side can be straight chain or branched, saturated or unsaturated.

The production of fatty esters, including waxes from acyl-CoA and alcohols can be engineered using known polypeptides. As used herein waxes are long chain fatty acid esters, wherein the A side and the B side of the ester can vary in length independently. Generally, the A side of the ester is at least 8, 10, 12, 14, 16, 18, 20, 22, 24, or 26 carbons in length. Similarly the B side of the ester is at least 8, 10, 12, 14, 16, 18, 20, 22, 24, or 26 carbons in length. The A side and the B side can be mono-, di-, tri-unsaturated. The production of fatty esters, including waxes from acyl-CoA and alcohols can be engineered using known polypeptides. One method of making fatty esters includes increasing the expression of or expressing more active forms of one or more wax synthases (EC 2.3.1.75).

As used herein, wax synthases includes peptides in enzyme classification number EC 2.3.1.75, as well as any other peptide capable of catalyzing the conversion of an acyl-thioester to fatty esters. Additionally, one of ordinary skill in the art will appreciate that some wax synthase peptides will catalyze other reactions as well, for example some wax synthase peptides will accept short chain acyl-CoAs and short chain alcohols to produce fatty esters. Such non-specific wax synthases are, therefore, also included. Wax synthase peptide sequences are publicly available. Exemplary GenBank Accession Numbers are provided in FIG. 10. Methods to identify wax synthase activity are provided in U.S. Pat. No. 7,118,896, which is herein incorporated by reference.

In particular examples, if the desired product is a fatty ester based biofuel, the microorganism is modified so that it produces a fatty ester generated from a renewable energy source. Such a microorganism includes an exogenous DNA sequence encoding a wax ester synthase that is expressed so as to confer upon said microorganism the ability to synthesize a saturated, unsaturated, or branched fatty ester from a renewable energy source. In some embodiments, the wax ester synthesis proteins include, but are not limited to: fatty acid elongases, acyl-CoA reductases, acyltransferases or wax synthases, fatty acyl transferases, diacylglycerol acyltransferases, acyl-coA wax alcohol acyltransferases, bifunctional wax ester synthase/acyl-CoA:diacylglycerol acyltransferase selected from a multienzyme complex from *Simmondsia chinensis, Acinetobacter* sp. strain ADP1 (formerly *Acinetobacter calcoaceticus* ADP1), *Pseudomonas aeruginosa, Fundibacter jadensis, Arabidopsis thaliana*, or *Alkaligenes eutrophus*. In one embodiment, the fatty acid elongases, acyl-CoA reductases or wax synthases are from a multienzyme complex from *Alkaligenes eutrophus* and other organisms known in the literature to produce wax and fatty acid esters.

Additional sources of heterologous DNA encoding wax synthesis proteins useful in fatty ester production include, but are not limited to, *Mortierella alpina* (for example ATCC 32222), *Crytococcus curvatus*, (also referred to as *Apiotricum curvatum*), *Alcanivora jadensis* (for example T9T=DSM 12718=ATCC 700854), *Acinetobacter* sp. HO1-N, (for example ATCC 14987) and *Rhodococcus opacus* (for example PD630, DSMZ 44193).

The methods of described herein permit production of fatty esters of varied length. In one example, the fatty ester product is a saturated or unsaturated fatty ester product having a carbon atom content between 24 and 46 carbon atoms. In one embodiment, the fatty ester product has a carbon atom content between 24 and 32 carbon atoms. In another embodiment the fatty ester product has a carbon content of 14 and 20 carbons. In another embodiment the fatty ester is the methyl ester of C18:1. In another embodiment the fatty acid ester is the ethyl ester of C16:1. In another embodiment the fatty ester is the methyl ester of C16:1. In another embodiment the fatty acid ester is octadecyl ester of octanol, Useful hosts for producing fatty esters can be either eukaryotic or prokaryotic microorganisms. In some embodiments such hosts include, but are not limited to, *Saccharomyces cerevisiae, Candida lipolytica, E. coli, Arthrobacter* AK 19, *Rhodotorula glutinins, Acinobacter* sp strain M-1, *Candida lipolytica* and other oleaginous microorganisms.

In one example the wax ester synthase from *Acinetobacter* sp. ADP1 at locus AAO17391 (described in Kalscheuer and Steinbuchel, *J. Biol. Chem.* 278:8075-8082, 2003, herein incorporated by reference) is used. In another example the wax ester synthase from *Simmondsia chinensis*, at locus AAD38041 is used.

Optionally a wax ester exporter such as a member of the FATP family can be used to facilitate the release of waxes or esters into the extracellular environment. One example of a wax ester exporter that can be used is fatty acid (long chain) transport protein CG7400-PA, isoform A from *Drosophila melanogaster*, at locus NP_524723.

G. Acyl-ACP, Acyl-CoA to Hydrocarbon

A diversity of microorganisms are known to produce hydrocarbons, such as alkanes, olefins, and isoprenoids. Many of these hydrocarbons are derived from fatty acid biosynthesis. The production of these hydrocarbons can be controlled by controlling the genes associated with fatty acid biosynthesis in the native hosts. For example, hydrocarbon biosynthesis in the algae *Botryococcus braunii* occurs through the decarbonylation of fatty aldehydes. The fatty aldehydes are produced by the reduction of fatty acyl—thioesters by fatty acyl-CoA reductase. Thus, the structure of the final alkanes can be controlled by engineering *B. braunii* to express specific genes, such as thioesterases, which control the chain length of the fatty acids being channeled into alkane biosynthesis. Expressing the enzymes that result in branched chain fatty acid biosynthesis in *B. braunii* will result in the production of branched chain alkanes. Introduction of genes effecting the production of desaturation of fatty acids will result in the production of olefins. Further combinations of these genes can provide further control over the final structure of the hydrocarbons produced. To produce higher levels of the native or engineered hydrocarbons, the genes involved in the biosynthesis of fatty acids and their precursors or the degradation to other products can be expressed, overexpressed, or attenuated. Each of these approaches can be applied to the production of alkanes in *Vibrio furnissi* M1 and its functional homologues, which produces alkanes through the reduction of fatty alcohols (see above for the biosynthesis and engineering of fatty alcohol production). Each of these approaches can also be applied to the production of the olefins produced by many strains of *Micrococcus leuteus, Stenotrophomonas maltophilia, Jeogalicoccus* sp. (ATCC8456), and related microorganisms. These microorganisms produce long chain internal olefins that are derived from the head to head condensation of fatty acid precursors. Controlling the structure and level of the fatty acid precursors using the methods described herein will result in formation of olefins of different chain length, branching, and level of saturation.

Hydrocarbons can also be produced using evolved oxido/reductases for the reduction of primary alcohols. Primary fatty alcohols are known to be used to produce alkanes in microorganisms such as *Vibrio fitrnissii* M1 (Myong-Ok, *J. Bacteriol.*, 187:1426-1429, 2005). An NAD(P)H dependent oxido/reductase is the responsible catalyst. Synthetic NAD(P)H dependent oxidoreductases can be produced through the use of evolutionary engineering and be expressed in production hosts to produce fatty acid derivatives. One of ordinary skill in the art will appreciate that the process of "evolving" a fatty alcohol reductase to have the desired activity is well known (Kolkman and Stemmer *Nat Biotechnol.* 19:423-8, 2001, Ness et al., *Adv Protein Chem.* 55:261-92, 2000, Minshull and Stemmer *Curr Opin Chem Biol.* 3:284-90, 1999, Huisman and Gray *Curr Opin Biotechnol.* August; 13:352-8, 2002, and see U.S. patent application 2006/0195947). A library of NAD(P)H dependent oxidoreductases is generated by standard methods, such as error prone PCR, site-specific random mutagenesis, site specific saturation mutagenesis, or site directed specific mutagenesis. Additionally, a library can be created through the "shuffling" of naturally occurring NAD(P)H dependent oxidoreductase encoding sequences. The library is expressed in a suitable host, such as *E. coli*. Individual colonies expressing a different member of the oxido/reductase library is then analyzed for its expression of an oxido/reductase that can catalyze the reduction of a fatty alcohol. For example, each cell can be assayed as a whole cell bioconversion, a cell extract, a permeabilized cell, or a purified enzyme. Fatty alcohol reductases are identified by the monitoring the fatty alcohol dependent oxidation of NAD(P)H spectrophotometrically or fluorometrically. Production of alkanes is monitored by GC/MS, TLC, or other methods, An oxido/reductase identified in this manner is used to produce alkalies, alkenes, and related branched hydrocarbons. This is achieved either in vitro or in vivo. The latter is achieved by expressing the evolved fatty alcohol reductase gene in an organism that produces fatty alcohols, such as those described herein. The fatty alcohols act as substrates for the alcohol reductase which would produce alkanes. Other oxidoreductases can be also engineered to catalyze this reaction, such as those that use molecular hydrogen, glutathione, FADH, or other reductive coenzymes.

II Genetic Engineering of Production Strain to increase Fatty Acid Derivative Production Heterologous DNA sequences involved in a biosynthetic pathway for the production of fatty acid derivatives can be introduced stably or transiently into a host cell using techniques well known in the art for example electroporation, calcium phosphate precipitation, DEAE-dextran mediated transfection, liposome-mediated transfection, conjugation, transduction, and the like. For stable transformation, a DNA sequence can further include a selectable marker, such as, antibiotic resistance, for example resistance to neomycin, tetracycline, chloramphenicol, kanamycin, genes that complement auxotrophic deficiencies, and the like.

Various embodiments of this disclosure utilize an expression vector that includes a heterologous DNA sequence encoding a protein involved in a metabolic or biosynthetic pathway. Suitable expression vectors include, but are not limited to, viral vectors, such as baculovirus vectors, phage vectors, such as bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as *E. coli, Pseudomonas pisum* and *Saccharomyces cerevisiae*).

Useful expression vectors can include one or more selectable marker genes to provide a phenotypic trait for selection of transformed host cells. The selectable marker gene encodes a protein necessary for the survival or growth of transformed host cells grown in a selective culture medium. Host cells not transformed with the vector containing the selectable marker gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*. In alternative embodiments, the selectable marker gene is one that encodes dihydrofolate reductase or confers neomycin resistance (for use in eukaryotic cell culture), or one that confers tetracycline or ampicillin resistance (for use in a prokaryotic host cell, such as *E. coli*).

The biosynthetic pathway gene product-encoding DNA sequence in the expression vector is operably linked to an appropriate expression control sequence, (promoters, enhancers, and the like) to direct synthesis of the encoded gene product. Such promoters can be derived from microbial or viral sources, including CMV and SV40. Depending on the host/vector system utilized, any of a number of suitable transcription and translation control elements, including constitutive and inducible promoters, transcription enhancer elements, transcription terminators, etc. can be used in the expression vector (see e.g., Bitter et at, *Methods in Enzymology*, 153:516-544, 1987).

Suitable promoters for use in prokaryotic host cells include, but are not limited to, promoters capable of recognizing the T4, T3, Sp6 and T7 polymerases, the $P_R$ and $P_L$ promoters of bacteriophage lambda, the trp, recA, heat shock, and lacZ promoters of *E. coli*, the alpha-amylase and the sigma-specific promoters of *B. subtilis*, the promoters of the bacteriophages of *Bacillus, Streptomyces* promoters, the int promoter of bacteriophage lambda, the bla promoter of the beta-lactamase gene of pBR322, and the CAT promoter of the chloramphenicol acetyl transferase gene. Prokaryotic promoters are reviewed by Glick, *J. Ind. Microbial.* 1:277, 1987; Watson et al., MOLECULAR BIOLOGY OF THE GENE, 4th Ed., Benjamin Cummins (1987); and Sambrook et al., supra.

Non-limiting examples of suitable eukaryotic promoters for use within a eukaryotic host are viral in origin and include the promoter of the mouse metallothionein 1 gene (Hamer et al., *J. Mol. Appl. Gen.* 1:273, 1982); the TK promoter of Herpes virus (McKnight, Cell 31:355, 1982); the SV40 early promoter (Benoist et al., *Nature (London)* 290:304, 1981); the Rolls sarcoma virus promoter; the cytomegalovirus promoter (Foecking et al., Gene 45:101, 1980); the yeast gal4 gene promoter (Johnston, et al., *PNAS (USA)* 79:6971, 1982; Silver, et al., *PNAS (USA)* 81:5951, 1984); and the IgG promoter (Orlandi et al., *PNAS (USA)* 86:3833, 1989).

The microbial host cell can be genetically modified with a heterologous DNA sequence encoding a biosynthetic pathway gene product that is operably linked to an inducible promoter. Inducible promoters are well known in the art. Suitable inducible promoters include, but are not limited to promoters that are affected by proteins, metabolites, or chemicals. These include: a bovine leukemia virus promoter, a metallothionein promoter, a dexamethasone-inducible MMTV promoter, a SV40 promoter, a MRP polIII promoter, a tetracycline-inducible CMV promoter (such as the human immediate-early CMV promoter) as well as those from the trp and lac operons.

In some examples a genetically modified host cell is genetically modified with a heterologous DNA sequence encoding a biosynthetic pathway gene product that is operably linked to a constitutive promoter. Suitable constitutive promoters are known in the art and include, constitutive adenovirus major late promoter, a constitutive MPSV promoter, and a constitutive CMV promoter.

In some examples a modified host cell is one that is genetically modified with an exogenous DNA sequence encoding a single protein involved in a biosynthesis pathway. In other embodiments, a modified host cell is one that is genetically modified with exogenous DNA sequences encoding two or more proteins involved in a biosynthesis pathway—for example, the first and second enzymes in a biosynthetic pathway.

Where the host cell is genetically modified to express two or more proteins involved in a biosynthetic pathway, those DNA sequences can each be contained in a single or in separate expression vectors. When those DNA sequences are contained in a single expression vector, in some embodiments, the nucleotide sequences will be operably linked to a common control element (e.g., a promoter), e.g., the common control element controls expression of all of the biosynthetic pathway protein-encoding DNA sequences in the single expression vector.

When a modified host cell is genetically modified with heterologous DNA sequences encoding two or more proteins involved in a biosynthesis pathway, one of the DNA sequences can be operably linked to an inducible promoter, and one or more of the DNA sequences can be operably linked to a constitutive promoter.

In some embodiments, the intracellular concentration (e.g., the concentration of the intermediate in the genetically modified host cell) of the biosynthetic pathway intermediate can be increased to further boost the yield of the final product. The intracellular concentration of the intermediate can be increased in a number of ways, including, but not limited to, increasing the concentration in the culture medium of a substrate for a biosynthetic pathway; increasing the catalytic activity of an enzyme that is active in the biosynthetic pathway; increasing the intracellular amount of a substrate (e.g., a primary substrate) for an enzyme that is active in the biosynthetic pathway; and the like.

In some examples the fatty acid derivative or intermediate is produced in the cytoplasm of the cell. The cytoplasmic concentration can be increased in a number of ways, including, but not limited to, binding of the fatty acid to coenzyme A to form an acyl-CoA thioester. Additionally, the concentration of acyl-CoAs can be increased by increasing the biosynthesis of CoA in the cell, such as by over-expressing genes associated with pantothenate biosynthesis (panD) or knocking out the genes associated with glutathione biosynthesis (glutathione synthase).

III. Carbon Chain Characteristics

Using the teachings provided herein a range of products can be produced. These products include hydrocarbons, fatty alcohols, fatty acid esters, and waxes. Some of these products are useful as biofuels and specialty chemicals. These products can be designed and produced in microorganisms. The products can be produced such that they contain branch points, levels of saturation, and carbon chain length, thus, making these products desirable starting materials for use in many applications (FIG. 10 provides a description of the various enzymes that can be used alone or in combination to make various fatty acid derivatives).

In other examples, the expression of exogenous FAS genes originating from different species or engineered variants can be introduced into the host cell to result in the biosynthesis of fatty acid metabolites structurally different (in length, branching, degree of unsaturation, etc.) as that of the native host. These heterologous gene products can be also chosen or engineered so that they are unaffected by the natural complex regulatory mechanisms in the host cell and, therefore, function in a manner that is more controllable for the production of the desired commercial product. For example the FAS enzymes from *Bacillus subtilis, Saccharomyces cerevisiae, Streptomyces* spp, *Ralstonia, Rhodococcus, Corynebacteria, Brevibacteria, Mycobacteria*, oleaginous yeast, and the like can be expressed in the production host.

One of ordinary skill in the art will appreciate that when a production host is engineered to produce a fatty acid from the fatty acid biosynthetic pathway that contains a specific level of unsaturation, branching, or carbon chain length the resulting engineered fatty acid can be used in the production of the fatty acid derivatives. Hence, fatty acid derivatives generated from the production host can display the characteristics of the engineered fatty acid. For example, a production host can be engineered to make branched, short chain fatty acids, and then using the teachings provided herein relating to fatty alcohol production (i.e. including alcohol forming enzymes such as FAR) the production host produce branched, short chain fatty alcohols. Similarly, a hydrocarbon can be produced by engineering a production host to produce a fatty acid having a defined level of branching, unsaturation, and/or carbon chain length, thus, producing a homogenous hydrocarbon population. Moreover, when an unsaturated alcohol, fatty acid ester, or hydrocarbon is desired the fatty acid biosynthetic pathway can be engineered to produce low levels of saturated fatty acids and an additional desaturase can be expressed to lessen the saturated product production.

A. Saturation

Production hosts can be engineered to produce unsaturated fatty acids by engineering the production host to over-express fabB, or by growing the production host at low temperatures (for example less than 37° C.). FabB has preference to cis-$\delta^3$ decenoyl-ACP and results in unsaturated fatty acid production in *E. coli*, Over-expression of FabB resulted in the production of a significant percentage of unsaturated fatty acids (de Mendoza et al., *J. Biol. Chem.*, 258:2098-101, 1983). These unsaturated fatty acids can then be used as intermediates in production hosts that are engineered to produce fatty acid derivatives, such as fatty alcohols, esters, waxes, olefins, alkanes, and the like. One of ordinary skill in the art will appreciate that by attenuating fabA, or over-expressing FabB and expressing specific thioesterases (described below), unsaturated fatty acid derivatives having a desired carbon chain length can be produced. Alternatively, the repressor of fatty acid biosynthesis, FabR (Genbank accession NP_418398), can be deleted, which will also result in increased unsaturated fatty acid production in *E. coli* (Zhang et al., *J. Biol. Chem.* 277: pp. 15558, 2002.). Further increase in unsaturated fatty acids may be achieved by over-expression of FabM (trans-2, cis-3-decenoyl-ACP isomerase, Genbank accession DAA05501) and controlled expression of FabK (trans-2-enoyl-ACP reductase 11, Genbank accession NP_357969) from *Streptococcus pneumoniae* (Marrakchi et al., *J. Biol. Chem.* 277: 44809, 2002), while deleting *E. coli* Fab I ((trans-2-enoyl-ACP reductase, Genbank accession NP_415804). Additionally, to increase the percentage of unsaturated fatty acid esters, the microorganism can also have fabB (encoding β-ketoacyl-ACP synthase I, Accessions: BAA16180, EC:2.3.1.41), Sja (encoding a suppressor of fabA, Accession: AAC44390) and gnsA and gnsB (both encoding secG null mutant suppressors, a.k.a. cold shock proteins, Accession: ABD18647.1, AAC74076.1) over-expressed.

In some examples, the endogenous fabF gene can be attenuated, thus, increasing the percentage of palmitoleate (C16:1) produced.

B. Branching Including Cyclic Moieties

Fatty acid derivatives can be produced that contain branch points, cyclic moieties, and combinations thereof, using the teachings provided herein.

Microorganisms that naturally produce straight fatty acids (sFAs) can be engineered to produce branched chain fatty acids (brFAs) by expressing one or more exogenous nucleic acid sequences. For example, *E. coli* naturally produces straight fatty acids (sFAs). To engineer *E. coli* to produce brFAs, several genes can be introduced and expressed that provide branched precursors (bkd operon) and allow initiation of fatty acid biosynthesis from branched precursors (fabH). Additionally, the organism can express genes for the elongation of brFAs (e.g. ACP, FabF) and/or deleting the corresponding *E. coli* genes that normally lead to sFAs and would compete with the introduced genes (e.g. FabH, FabF).

The branched acyl-CoAs 2-methyl-buturyl-CoA, isovaleryl-CoA and isobuturyl-CoA are the precursors of brFA. In most brFA-containing microorganisms they are synthesized in two steps (described in detail below) from branched amino acids (isoleucine, leucine and valine) (Kadena, *Microbiol. Rev.* 55: pp. 288, 1991). To engineer a microorganism to produce brFAs, or to overproduce brFAs, expression or over-expression of one or more of the enzymes in these two steps can be engineered. For example, in some instances the production host may have an endogenous enzyme that can accomplish one step and therefore, only enzymes involved in the second step need to be expressed recombinantly.

The first step in forming branched fatty acids is the production of the corresponding α-keto acids by a branched-chain amino acid aminotransferase. *E. coli* has such an enzyme, IlvE (EC 2.6.1.42; Genbank accession YP_026247). In some examples, a heterologous branched-chain amino acid aminotransferase may not be expressed. However, *E. coli* IlvE or any other branched-chain amino acid aminotransferase, e.g. ilvE from *Lactococcus lactis* (Genbank accession AAF34406), ilvE from *Pseudomonas putida* (Genbank accession NP_745648) or ilvE from *Streptomyces coelicolor* (Genbank accession NP_629657) can be over-expressed in a host microorganism, should the aminotransferase reaction turn out to be rate limiting in brFA biosynthesis in the host organism chosen for fatty acid derivative production.

The second step, the oxidative decarboxylation of the α-ketoacids to the corresponding branched-chain acyl-CoA, is catalyzed by a branched-chain. α-keto acid dehydrogenase complexes (bkd; EC 1.2.4.4.) (Denoya et al. *J. Bacterial.* 177: pp. 3504, 1995), which consist of E1α/β (decarboxylase), E2 (dihydrolipoyl transacylase) and E3 (dihydrolipoyl dehydrogenase) subunits and are similar to pyruvate and α-ketoglutarate dehydrogenase complexes. Table 2 shows potential bkd genes from several microorganisms, that can be expressed in a production host to provide branched-chain acyl-CoA precursors. Basically, every microorganism that possesses brFAs and/or grows on branched-chain amino acids can be used as a source to isolate bkd genes for expression in production hosts such as, for example, *E. coli*. Furthermore, *E. coli* has the E3 component (as part of its pyruvate dehydrogenase complex; lpd, EC 1.8.1.4, Genbank accession NP_414658), it can therefore, be sufficient to only express the E1α/β and E2 bkd genes.

TABLE 2

Bkd genes from selected microorganisms

| Organism | Gene | Genbank Accession # |
|---|---|---|
| Streptomyces coelicolor | bkdA1 (E1α) | NP_628006 |
|  | bkdB1 (E1α) | NP_628005 |
|  | bkdC1 (E2) | NP_638004 |
| Streptomyces coelicolor | bkdA2 (E1α) | NP_733618 |
|  | bkdB2 (E1α) | NP_628019 |
|  | bkdC2 (E2) | NP_628018 |
| Streptomyces avermitilis | bkdA (E1a) | BAC72074 |
|  | bkdB (E1b) | BAC72075 |
|  | bkdC (E2) | BAC72076 |
| Streptomyces avermitilis | bkdF (E1α) | BAC72088 |
|  | bkdG (E1α) | BAC72089 |
|  | bkdH (E2) | BAC72090 |
| Bacillus subtilis | bkdAA (E1α) | NP_390288 |
|  | bkdAB (E1α) | NP_390288 |
|  | bkdB (E2) | NP_390288 |
| Pseudomonas putida | bkdA1 (E1α) | AAA65614 |
|  | bkdA2 (E1α) | AAA65615 |
|  | bkdC (E2) | AAA65617 |

In another example, isobuturyl-CoA can be made in a production host, for example in *E. coli* through the coexpression of a crotonyl-CoA reductase (Ccr, EC 1.1.1.9) and isobuturyl-CoA mutase (large subunit IcmA, EC 5.4.99.2; small subunit IcmB, EC 5.4.99.13) (Han and Reynolds *J. Bacteriol.* 179: pp. 5157, 1997). Crotonyl-CoA is an intermediate in fatty acid biosynthesis in *E. coli* and other microorganisms. Examples for ccr and icm genes from selected microorganisms are given in Table 3.

TABLE 3

Ccr and icm genes from selected microorganisms

| Organism | Gene | Genbank Accession # |
|---|---|---|
| Streptomyces coelicolor | ccr | NP_630556 |
|  | icmA | NP_629554 |
|  | icmB | NP_630904 |
| Streptomyces cinnamonensis | ccr | AAD53915 |
|  | icmA | AAC08713 |
|  | icmB | AJ246005 |

In addition to expression of the bkd genes (see above), the initiation of brFA biosynthesis utilizes β-ketoacyl-acyl-carrier-protein synthase Iii (FabH, EC 2.3.1.41) with specificity for branched chain acyl CoAs (Li et al. *J. Bacteriol.* 187: pp, 3795, 2005). Examples of such FabHs are listed in Table 4. FabH genes that are involved in fatty acid biosynthesis of any brFA-containing microorganism can be expressed in a production host. The Bkd and FabH enzymes from production hosts that do not naturally make brFA may not support brFA production and therefore, Bkd and FabH can be expressed recombinantly. Similarly, the endogenous level of Bkd and FabH production may not be sufficient to produce brFA, therefore, they can be over-expressed. Additionally, other components of fatty acid biosynthesis machinery can be expressed such as acyl carrier proteins (ACPs) and β-ketaacyl-acyl-carrier-protein synthase II candidates are acyl carrier proteins (ACPs) and β-ketoacyl-acyl-carrier-protein synthase II (fabF, EC 2.3.1.41) (candidates are listed in Table 4). In addition to expressing these genes, some genes in the endogenous fatty acid biosynthesis pathway may be attenuated in the production host. For example, in *E. coli* the most likely candidates to interfere with brFA biosynthesis are fabH (Genbank accession # NP_415609) and/or fabF genes (Genbank accession # NP_415613).

As mentioned above, through the combination of expressing genes that support brFA synthesis and alcohol synthesis branched chain alcohols can be produced. For example, when an alcohol reductase such as Acr1 from *Acinetobacter baylyi* ADP1 is coexpressed with a bkd operon, *E. coli* can synthesize isopentanol, isobutanol or 2-methyl butanol. Similarly, when Acr1 is coexpressed with ccr/icm genes, *E. coli* can synthesize isobutanol.

In order to convert a production host such as *E. coli* into an organism capable of synthesizing co-cyclic fatty acids (cyFAs), several genes need to be introduced and expressed that provide the cyclic precursor cyclohexylcarbonyl-CoA (Cropp et al. *Nature Biotech.* 18: pp. 980, 2000). The genes listed in Table 4 (fabH, ACP and fabF) can then be expressed to allow initiation and elongation of co-cyclic fatty acids. Alternatively, the homologous genes can be isolated from microorganisms that make cyFAs and expressed in *E. coli*.

TABLE 4

FabH, ACP and fabF genes from selected microorganisms with brFAs

| Organism | Gene | Genbank Accession # |
|---|---|---|
| Streptomyces coelicolor | fabH1 | NP_626634 |
|  | ACP | NP_626635 |
|  | fabF | NP_626636 |
| Streptomyces avermitilis | fabH3 | NP_823466 |
|  | fabC3 (ACP) | NP_823467 |
|  | fabF | NP_823468 |
| Bacillus subtilis | fabH_A | NP_389015 |
|  | fabH_B | NP_388898 |
|  | ACP | NP_389474 |
|  | fabF | NP_389016 |
| Stenotrophomonas maltophilia | SmalDRAFT_0818 (FabH) | ZP_01643059 |
|  | SmalDRAFT_0821 (ACP) | ZP_01643063 |
|  | SmalDRAFT_0822 (FabF) | ZP_01643064 |
| Legionella pneumophila | FabH | YP_123672 |
|  | ACP | YP_123675 |
|  | fabF | YP_123676 |

Expression of the following genes are sufficient to provide cyclohexylcarbonyl-CoA in *E. coli*: ansJ, ansK, ansL, chcA and ansM from the ansatrienin gene cluster of *Streptomyces collinus* (Chen et al., *Eur. J. Biochem.* 261: pp. 1999, 1999) or phnJ, phnK, phnL, chcA and plinM from the phoslactomycin B gene cluster of *Streptomyces* sp. HK803 (Palaniappan et al., *J. Biol. Chem.* 278: pp. 35552, 2003) together with the chcB gene (Patton et al. Biochem., 39: pp. 7595, 2000) from *S. collinus, S. avermitilis* or *S. coelicolor* (see Table 5 for Genbank accession numbers).

TABLE 5

Genes for the synthesis of cyclohexylcarbonyl-CoA

| Organism | Gene | Genbank Accession # |
|---|---|---|
| Streptomyces collinus | ansJK | U72144* |
|  | ansL |  |
|  | chcA |  |
|  | ansL |  |
|  | chcB | AF268489 |
| Streptomyces sp. HK803 | pmlJK | AAQ84158 |
|  | pmlL | AAQ84159 |
|  | chcA | AAQ84160 |
|  | pmlM | AAQ84161 |

TABLE 5-continued

Genes for the synthesis of cyclohexylcarbonyl-CoA

| Organism | Gene | Genbank Accession # |
|---|---|---|
| *Streptomyces coelicolor* | chcB/caiD | NP_629292 |
| *Streptomyces avermitilis* | chcB/caiD | NP_629292 |

*Only chcA is annotated in Genbank entry U72144, ansJKLM are according to Chen et al. (*Eur. J. Biochem.* 261: pp. 1999, 1999)

The genes listed in Table 4 (fabH, ACP and fabF) are sufficient to allow initiation and elongation of co-cyclic fatty acids, because they can have broad substrate specificity. In the event that coexpression of any of these genes with the ansJKLM/chcAB or pm1JKLM/chcAB genes from Table 5 does not yield cyFAs, fabH, ACP and/or fabF homologs from microorganisms that make cyFAs can be isolated (e.g. by using degenerate PCR primers or heterologous DNA probes) and coexpressed. Table 6 lists selected microorganisms that contain co-cyclic fatty acids.

TABLE 6

Examples of microorganisms that contain ω-cyclic fatty acids

| Organism | Reference |
|---|---|
| *Curtobacterium pusillum* | ATCC19096 |
| *Alicyclobacillus acidoterrestris* | ATCC49025 |
| *Alicyclobacillus acidocaldarius* | ATCC27009 |
| *Alicyclobacillus cycloheptanicum\** | Moore, *J. Org. Chem.* 62: pp. 2173, 1997. |

*uses cycloheptylcarbonyl-CoA and not cyclohexylcarbonyl-CoA as precursor for cyFA biosynthesis C. Ester Characteristics One of ordinary skill in the art will appreciate that an ester includes an A side and a B side. As described herein, the B side is contributed by a fatty acid produced from de novo synthesis in the host organism. In some instances where the host is additionally engineered to make alcohols, including fatty alcohols, the A side is also produced by the host organism. In yet other examples the A side can be provided in the medium. As described herein, by selecting the desired thioesterase genes the B side, and when fatty alcohols are being made the A side, can be designed to be have certain carbon chain characteristics. These characteristics include points of unsaturation, branching, and desired carbon chain lengths. Exemplary methods of making long chain fatly acid esters, wherein the A and B side are produced by the production host are provided in Example 6, below. Similarly, Example 5 provides methods of making medium chain fatty acid esters. When both the A and B side are contributed by the production host and they are produced using fatty acid biosynthetic pathway intermediates they will have similar carbon chain characteristics. For example, at least 50%, 60%, 70%, or 80% of the fatty acid esters produced will have A sides and B sides that vary by 6, 4, or 2 carbons in length. The A side and the B side will also display similar branching and saturation levels.

In addition to producing fatty alcohols for contribution to the A side, the host can produce other short chain alcohols such as ethanol, propanol, isopropanol, isobutanol, and butanol for incorporation on the A side using techniques well known in the art. For example, butanol can be made by the host organism. To create butanol producing cells, the LS9001 strain (described in Example 1, below) can be further engineered to express atoB (acetyl-CoA acetyltransferase) from *Escherichia coli* K12, p-hydroxybutyryl-CoA dehydrogenase from *Butyrivibrio fibrisolvens*, crotonase from *Clostridium beijerinckii*, butyryl CoA dehydrogenase from *Clostridium beijerinckii*, CoA-acylating aldehyde dehydrogenase (ALDH) from *Cladosporium fulvum*, and adhE encoding an aldehyde-alchol dehydrogenase of *Clostridium acetobutylicum* in the pBAD24 expression vector under the prpBCDE promoter system. Similarly, ethanol can be produced in a production host using the methods taught by Kalscheuer et al., *Microbiology* 152:2529-2536, 2006, which is herein incorporated by reference.

IV. Fermentation

The production and isolation of fatty acid derivatives can be enhanced by employing specific fermentation techniques. One method for maximizing production while reducing costs is increasing the percentage of the carbon source that is converted to hydrocarbon products. During normal cellular lifecycles carbon is used in cellular functions including producing lipids, saccharides, proteins, organic acids, and nucleic acids. Reducing the amount of carbon necessary for growth-related activities can increase the efficiency of carbon source conversion to output. This can be achieved by first growing microorganisms to a desired density, such as a density achieved at the peak of the log phase of growth. At such a point, replication checkpoint genes can be harnessed to stop the growth of cells. Specifically, quorum sensing mechanisms (reviewed in Camilli and Bassler *Science* 311: 1113, 2006; Venturi *FEMS Microbio Rev* 30:274-291, 2006; and Reading and Sperandio *FEMS Microbial Lett* 254:1-11, 2006) can be used to activate genes such as p53, p21, or other checkpoint genes. Genes that can be activated to stop cell replication and growth in *E. coli* include umuDC genes, the over-expression of which stops the progression from stationary phase to exponential growth (Murli et al., *J. of Bact.* 182:1127, 2000). UmuC is a DNA polymerase that can carry out translesion synthesis over non-coding lesions—the mechanistic basis of most UV and chemical mutagenesis. The zanuDC gene products are used for the process of translesion synthesis and also serve as a DNA damage checkpoint. UmuDC gene products include UmuC, UmuD, UmuD', UmuD'$_2$ and UmuD$_2$. Simultaneously, the product producing genes would be activated, thus minimizing the need for replication and maintenance pathways to be used while the fatty acid derivative is being made.

The percentage of input carbons converted to hydrocarbon products is a cost driver. The more efficient (i.e. the higher the percentage), the less expensive the process. For oxygen-containing carbon sources (i.e. glucose and other carbohydrate based sources), the oxygen must be released in the form of carbon dioxide. For every 2 oxygen atoms released, a carbon atom is also released leading to a maximal theoretical metabolic efficiency of about 34% (w/w) (for fatty acid derived products). This figure, however, changes for other hydrocarbon products and carbon sources. Typical efficiencies in the literature are about <5%. Engineered microorganisms which produce hydrocarbon products can have greater than 1, 3, 5, 10, 15, 20, 25, and 30% efficiency. In one example microorganisms will exhibit an efficiency of about 10% to about 25%. In other examples, such microorganisms will exhibit an efficiency of about 25% to about 30%, and in other examples such microorganisms will exhibit >30% efficiency.

In some examples where the final product is released from the cell, a continuous process can be employed. In this approach, a reactor with organisms producing fatty acid derivatives can be assembled in multiple ways. In one example, a portion of the media is removed and let to sit.

Fatty acid derivatives are separated from the aqueous layer, which will in turn, be returned to the fermentation chamber.

In one example, the fermentation chamber will enclose a fermentation that is undergoing a continuous reduction. In this instance, a stable reductive environment would be created. The electron balance would be maintained by the release of carbon dioxide (in gaseous form). Efforts to augment the NAD/H and NADP/H balance can also facilitate in stabilizing the electron balance.

The availability of intracellular NADPH can be also enhanced by engineering the production host to express an NADH:NADPH transhydrogenase. The expression of one or more NADH:NADPH transhydrogenase converts the NADH produced in glycolysis to NADPH which enhances the production of fatty acid derivatives.

Disclosed herein is a system for continuously producing and exporting fatty acid derivatives out of recombinant host microorganisms via a transport protein. Many transport and efflux proteins serve to excrete a large variety of compounds and can be evolved to be selective for a particular type of fatty acid derivatives. Thus, in some embodiments an exogenous DNA sequence encoding an ABC transporter will be functionally expressed by the recombinant host microorganism, so that the microorganism exports the fatty acid derivative into the culture medium. In one example, the ABC transporter is an ABC transporter from *Caenorhabditis elegans, Arabidopsis thalania, Alkaligenes eutrophus* or *Rhodococcus erythropolis* (locus AAN73268). In another example, the ABC transporter is an ABC transporter chosen from CERS (locuses At1g51500 or AY734542), AtMRP5, AmiS2 and AtPGP1. In some examples, the ABC transporter is CERS. In yet another example, the CERS gene is from *Arabidopsis* (lotuses At1g51500, AY734542, At3g21090 and At1g51460).

The transport protein, for example, can also be an efflux protein selected from: AcrAB, TolC and AcrEF from *E. coli*, or tll1618, tll1619 and tll0139 from Thermosynechococcus elongatus BP-1.

In addition, the transport protein can be, for example, a fatty acid transport protein (FATP) selected from *Drosophila melanogaster, Caenorhabditis elegans, Mycobacterium luberculasis* or *Saccharomyces cerevisiae* or any one of the mammalian FATP's. The FATPs can additionally be resynthesized with the membranous regions reversed in order to invert the direction of substrate flow. Specifically, the sequences of amino acids composing the hydrophilic domains (or membrane domains) of the protein, could be inverted while maintaining the same codons for each particular amino acid. The identification of these regions is well known in the art.

Production hosts can also be chosen for their endogenous ability to release fatty acid derivatives. The efficiency of product production and release into the fermentation broth can be expressed as a ratio intracellular product to extracellular product. In some examples the ratio can be 5:1, 4:1, 3:1, 2:1, 1:1, 1:2, 1:3, 1:4, or 1:5.

The production host can be additionally engineered to express recombinant cellulosomes, such as those described in PCT application number PCT/US2007/003736, which will allow the production host to use cellulosic material as a carbon source. For example, the production host can be additionally engineered to express invertases (EC 3.2.1.26) so that sucrose can be used as a carbon source.

Similarly, the production host can be engineered using the teachings described in U.S. Pat. Nos. 5,000,000, 5,028,539, 5,424,202, 5,482,846, and 5,602,030 to Ingram et al. so that the production host can assimilate carbon efficiently and use cellulosic materials as carbons sources.

IV. Post Production Processing

The fatty acid derivatives produced during fermentation can be separated from the fermentation media. Any technique known for separating fatty acid derivatives from aqueous media can be used. One exemplary separation process provided herein is a two phase (bi-phasic) separation process. This process involves fermenting the genetically engineered production hosts under conditions sufficient to produce a fatty acid derivative, allowing the derivative to collect in an organic phase and separating the organic phase from the aqueous fermentation broth. This method can be practiced in both a batch and continuous fermentation setting.

Bi-phasic separation uses the relative immisiciblity of fatty acid derivatives to facilitate separation. Immiscible refers to the relative inability of a compound to dissolve in water and is defined by the compounds partition coefficient. The partition coefficient, P, is defined as the equilibrium concentration of compound in an organic phase (in a bi-phasic system the organic phase is usually the phase formed by the fatty acid derivative during the production process, however, in some examples an organic phase can be provided (such as a layer of octane to facilitate product separation) divided by the concentration at equilibrium in an aqueous phase (i.e. fermentation broth). When describing a two phase system the P is usually discussed in terms of log P. A compound with a log P of 10 would partition 10:1 to the organic phase, while a compound of log P of 0.1 would partition 10:1 to the aqueous phase. One or ordinary skill in the art will appreciate that by choosing a fermentation broth and the organic phase such that the fatty acid derivative being produced has a high log P value, the fatty acid derivative will separate into the organic phase, even at very low concentrations in the fermentation vessel.

The fatty acid derivatives produced by the methods described herein will be relatively immiscible in the fermentation broth, as well as in the cytoplasm. Therefore, the fatty acid derivative will collect in an organic phase either intracellularly or extracellularly. The collection of the products in an organic phase will lessen the impact of the fatty acid derivative on cellular function and will allow the production host to produce more product. Stated another way, the concentration of the fatty acid derivative will not have as significant of an impact on the host cell.

The fatty alcohols, fatty acid esters, waxes, and hydrocarbons produced as described herein allow for the production of homogeneous compounds wherein at least 60%, 70%, 80%, 90%, or 95% of the fatty alcohols, fatty acid esters, and waxes produced will have carbon chain lengths that vary by less than 4 carbons, or less than 2 carbons. These compounds can also be produced so that they have a relatively uniform degree of saturation, for example at least 60%, 70%, 80%, 90%, or 95% of the fatty alcohols, fatty acid esters, hydrocarbons and waxes will be mono-, di-, or tri-unsaturated. These compounds can be used directly as fuels, personal care additives, nutritional supplements. These compounds can also be used as feedstock for subsequent reactions for example transesterification, hydrogenation, catalytic cracking via either hydrogenation, pyrolisis, or both or epoxidations reactions to make other products.

V. Fuel Compositions

The fatty acid derivatives described herein can be used as fuel. One of ordinary skill in the art will appreciate that depending upon the intended purpose of the fuel different fatty acid derivatives can be produced and used. For example, for automobile fuel that is intended to be used in cold climates a branched fatty acid derivative may be desirable and using the teachings provided herein, branched hydrocarbons, fatty acid esters, and alcohols can be made. Using the methods described herein fuels comprising relatively homogeneous fatty acid derivatives that have desired fuel qualities can be produced. Such fuels can be characterized by carbon fingerprinting, their lack of impurities when compared to petroleum derived fuels or bio-diesel derived from triglycerides and, moreover, the fatty acid derivative based fuels can be combined with other fuels or fuel additives to produce fuels having desired properties.

A. Carbon Fingerprinting

Biologically produced fatty acid derivatives represent a new feedstock for fuels, such as alcohols, diesel and gasoline. Some biofuels made using fatty acid derivatives have not been produced from renewable sources and as such, are new compositions of matter. These new fuels can be distinguished from fuels derived form petrochemical carbon on the basis of dual carbon-isotopic fingerprinting. Additionally, the specific source of biosourced carbon (e.g. glucose vs. glycerol) can be determined by dual carbon-isotopic fingerprinting (see, U.S. Pat. No. 7,169,588, which is herein incorporated by reference).

This method usefully distinguishes chemically-identical materials, and apportions carbon in products by source (and possibly year) of growth of the biospheric (plant) component. The isotopes, $^{14}C$ and $^{13}C$, bring complementary information to this problem. The radiocarbon dating isotope ($^{14}C$), with its nuclear half life of 5730 years, clearly allows one to apportion specimen carbon between fossil ("dead") and biospheric ("alive") feedstocks [Currie, L. A. "Source Apportionment of Atmospheric Particles," Characterization of Environmental Particles, J. Baffle and H. P. van Leeuwen, Eds., 1 of Vol. I of the IUPAC Environmental Analytical Chemistry Series (Lewis Publishers, Inc) (1992) 3 74]. The basic assumption in radiocarbon dating is that the constancy of $^{14}C$ concentration in the atmosphere leads to the constancy of $^{14}C$ in living organisms. When dealing with an isolated sample, the age of a sample can be deduced approximately by the relationship $t=(-5730/0.693)\ln(A/A.sub.O)$ (Equation 5) where t=age, 5730 years is the half-life of radiocarbon, and A and A.sub.O are the specific $^{14}C$ activity of the sample and of the modern standard, respectively [Hsieh, Y., Soil Sci. Soc. Am J., 56, 460, (1992)]. However, because of atmospheric nuclear testing since 1950 and the burning of fossil fuel since 1850, $^{14}C$ has acquired a second, geochemical time characteristic. Its concentration in atmospheric CO2—and hence in the living biosphere—approximately doubled at the peak of nuclear testing, in the mid-1960s. It has since been gradually returning to the steady-state cosmogenic (atmospheric) baseline isotope rate ($^{14}C/^{12}C$) of ca. $1.2 \times 10^{12}$, with an approximate relaxation "half-life" of 7-10 years. (This latter half-life must not be taken literally; rather, one must use the detailed atmospheric nuclear input/decay function to trace the variation of atmospheric and biospheric $^{14}C$ since the onset of the nuclear age.) It is this latter biospheric $^{14}C$ time characteristic that holds out the promise of annual dating of recent biospheric carbon. $^{14}C$ can be measured by accelerator mass spectrometry (AMS), with results given in units of "fraction of modern carbon" ($f_M$). $f_M$ is defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_M$ approx 1.1.

The stable carbon isotope ratio ($^{13}C/^{12}C$) provides a complementary route to source discrimination and apportionment. The $^{13}C/^{12}C$ ratio in a given biosourced material is a consequence of the $^{13}C/^{12}C$ ratio in atmospheric carbon dioxide at the time the carbon dioxide is fixed and also reflects the precise metabolic pathway. Regional variations also occur. Petroleum, C3 plants (the broadleaf), C.sub.4 plants (the grasses), and marine carbonates all show significant differences in $^{13}C/^{12}C$ and the corresponding delta $^{13}C$ values. Furthermore, lipid matter of C3 and C4 plants analyze differently than materials derived from the carbohydrate components of the same plants as a consequence of the metabolic pathway. Within the precision of measurement, $^{13}C$ shows large variations due to isotopic fractionation effects, the most significant of which for the instant invention is the photosynthetic mechanism. The major cause of differences in the carbon isotope ratio in plants is closely associated with differences in the pathway of photosynthetic carbon metabolism in the plants, particularly the reaction occurring during the primary carboxylation, i.e., the initial fixation of atmospheric $CO_2$. Two large classes of vegetation are those that incorporate the "C3" (or Calvin-Benson) photosynthetic cycle and those that incorporate the "C4" (or Hatch-Slack) photosynthetic cycle. C3 plants, such as hardwoods and conifers, are dominant in the temperate climate zones. In C3 plants, the primary $CO_2$ fixation or carboxylation reaction involves the enzyme ribulose-1,5-diphosphate carboxylase and the first stable product is a 3-carbon compound. C4 plants, on the other hand, include such plants as tropical grasses, corn and sugar cane. In C4 plants, an additional carboxylation reaction involving another enzyme, phosphoenol-pyruvate carboxylase, is the primary carboxylation reaction. The first stable carbon compound is a 4-carbon acid which is subsequently decarboxylated. The $CO_2$ thus released is refixed by the C3 cycle.

Both C4 and C3 plants exhibit a range of $^{13}C/^{12}C$ isotopic ratios, but typical values are ca. −10 to −14 per mil (C4) and −21 to −26 per mil (C3) [Weber et al., J. Agric. Food Chem., 45, 2942 (1997)]. Coal and petroleum fall generally in this latter range. The $^{13}C$ measurement scale was originally defined by a zero set by pee dee belemnite (PDB) limestone, where values are given in parts per thousand deviations from this material. The "$\Delta^{13}C$", values are in parts per thousand (per mil), abbreviated ‰, and are calculated as follows:

$$\delta^{13}C = \frac{(^{13}C/^{12}C)_{sample} - (^{13}C/^{12}C)_{standard}}{(^{13}C/^{12}C)_{standard}} \times 100\% \quad \text{(Equation 6)}$$

Since the PDB reference material (RM) has been exhausted, a series of alternative RMs have been developed in cooperation with the IAEA, USGS, NEST, and other selected international isotope laboratories. Notations for the per mil deviations from PDB is $\Delta^{13}C$. Measurements are made on $CO_2$ by high precision stable ratio mass spectrometry (IRMS) on molecular ions of masses 44, 45 and 46.

The fatty acid derivatives and the associated biofuels, chemicals, and mixtures may be completely distinguished from their petrochemical derived counterparts on the basis of $^{13}C$ (fM) and dual carbon-isotopic fingerprinting, indicating new compositions of matter.

The fatty acid derivatives described herein have utility in the production of biofuels and chemicals. The new fatty acid derivative based product compositions provided by the instant invention additionally may be distinguished on the basis of dual carbon-isotopic fingerprinting from those materials derived solely from petrochemical sources. The ability to distinguish these products is beneficial in tracking these materials in commerce. For example, fuels or chemicals comprising both "new" and "old" carbon isotope profiles may be distinguished from fuels and chemicals made only of "old" materials. Hence, the instant materials may be followed in commerce on the basis of their unique profile and for the purposes of defining competition, and for determining shelf life.

In some examples a biofuel composition is made that includes a fatty acid derivative having $\delta^{13}C$ of from about −10.9 to about −15.4, wherein the fatty acid derivative accounts for at least about 85% of biosourced material (derived from a renewable resource such as cellulosic materials and sugars) in the composition. In other examples, the biofuel composition includes a fatty acid derivative having the formula

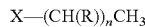

$$X\text{—}(CH(R))_n CH_3$$

wherein X represents $CH_3$, $-CH_2OR^1$; $-C(O)OR^2$; or $-C(O)NR^3R^4$;

R is, for each n, independently absent, H or lower aliphatic;

n is an integer from 8 to 34, such as from 10 to 24; and $R^1$, $R^2$, $R^3$ and $R^4$ independently are selected from H and lower alkyl. Typically, when R is lower aliphatic, R represents a branched, unbranched or cyclic lower alkyl or lower alkenyl moiety. Exemplary R groups include, without limitation, methyl, isopropyl, isobutyl, sec-butyl, cyclopentenyl and the like. The fatty acid derivative is additionally characterized as having a $\delta^{13}C$ of from about −10.9 to about −15.4; and the fatty acid derivative accounts for at least about 85% of biosourced material in the composition. In some examples the fatty acid derivative in the biofuel composition is characterized by having a fraction of modern carbon ($f_M^{14}C$) of at least about 1.003, 1.010, or 1.5.

B. Fatty Acid Derivatives

The centane number (CN), viscosity, melting point, and heat of combustion for various fatty acid esters have been characterized in for example, Knothe, *Fuel Processing Technology* 86:1059-1070, 2005, which is herein incorporated by reference. Using the teachings provided herein a production host can be engineered to produce anyone of the fatty acid esters described in the Knothe, *Fuel Processing Technology* 86:1059-1070, 2005.

Alcohols (short chain, long chain, branched or unsaturated) can be produced by the production hosts described herein. Such alcohols can be used as fuels directly or they can be used to create an ester, i.e. the A side of an ester as described above. Such ester alone or in combination with the other fatty acid derivatives described herein are useful a fuels.

Similarly, hydrocarbons produced from the microorganisms described herein can be used as biofuels. Such hydrocarbon based fuels can be designed to contain branch points, defined degrees of saturation, and specific carbon lengths. When used as biofuels alone or in combination with other fatty acid derivatives the hydrocarbons can be additionally combined with additives or other traditional fuels (alcohols, diesel derived from triglycerides, and petroleum based fuels).

C. Impurities

The fatty acid derivatives described herein are useful for making bio-fuels. These fatty acid derivatives are made directly from fatty acids and not from the chemical processing of triglycerides. Accordingly, fuels comprising the disclosed fatty acid derivatives will contain less of the impurities than are normally associated with bio-fuels derived from triglycerides, such as fuels derived from vegetable oils and fats.

The crude fatty acid derivative bio-fuels described herein (prior to mixing the fatty acid derivative with other fuels such as traditional fuels) will contain less transesterification catalyst than petrochemical diesel or bio-diesel. For example, the fatty acid derivative can contain less than about 2%, 1.5%, 1.0%, 0.5%, 0.3%, 0.1%, 0.05%, or 0% of a transesterification catalyst or an impurity resulting from a transesterification catalyst. Transesterification catalysts include for example, hydroxide catalysts such as NaOH, KOH, LiOH, and acidic catalysts, such as mineral acid catalysts and Lewis acid catalysts. Catalysts and impurities resulting from transesterification catalysts include, without limitation, tin, lead, mercury, cadmium, zinc, titanium, zirconium, hafnium, boron, aluminum, phosphorus, arsenic, antimony, bismuth, calcium, magnesium, strontium, uranium, potassium, sodium, lithium, and combinations thereof.

Similarly, the crude fatty acid derivative bio-fuels described herein (prior to mixing the fatty acid derivative with other fuels such as petrochemical diesel or bio-diesel) will contain less glycerol (or glycerin) than bio-fuels made from triglycerides. For example, the fatty acid derivative can contain less than about 2%, 1.5%, 1.0%, 0.5%, 0.3%, 0.1%, 0.05%, or 0% glycerol.

The crude biofuel derived from fatty acid derivatives will also contain less free alcohol (i.e. alcohol that is used to create the ester) than bio-diesel made from triglycerides. This is in-part due to the efficiency of utilization of the alcohol by the production host. For example, the fatty acid derivative will contain less than about 2%, 1.5%, 1.0%, 0.5%, 0.3%, 0.1%, 0.05%, or 0% free alcohol.

Biofuel derived from the disclosed fatty acid derivatives can be additionally characterized by its low concentration of sulfur compared to petroleum derived diesel. For example, biofuel derived from fatty acid derivatives can have less than about 2%, 1.5%, 1.0%, 0.5%, 0.3%, 0.1%, 0.05%, or 0% sulfur.

D. Additives

Fuel additives are used to enhance the performance of a fuel or engine. For example, fuel additives can be used to alter the freezing/gelling point, cloud point, lubricity, viscosity, oxidative stability, ignition quality, octane level, and flash point. In the United States, all fuel additives must be registered with Environmental Protection Agency and companies that sell the fuel additive and the name of the fuel additive are publicly available on the agency website and also by contacting the agency. One of ordinary skill in the art will appreciate that the fatty acid derivatives described herein can be mixed with one or more such additives to impart a desired quality.

One of ordinary skill in the art will also appreciate that the fatty acid derivatives described herein are can be mixed with other fuels such as bio-diesel derived from triglycerides, various alcohols such as ethanol and butanol, and petroleum derived products such as gasoline. In some examples, a fatty acid derivative, such as C16:1 ethyl ester or C18:1 ethyl ester, is produced which has a low gel point. This low gel point fatty acid derivative is mixed with bio-diesel made from triglycerides to lessen the overall gelling point of the fuel. Similarly, a fatty acid derivative such as C16:1 ethyl ester or C18:1 ethyl ester can be mixed with petroleum derived diesel to provide a mixture that is at least and often greater than 5% biodiesel. In some examples, the mixture includes at least 20% or greater of the fatty acid derivative.

For example, a biofuel composition can be made that includes at least about 20%, 30%, 40%, 50%, 60%, 70%, 80%, 85%, 90% or 95% of a fatty acid derivative that includes a carbon chain that is 8:0, 10:0, 12:0, 14:0, 14:1, 16:0, 16:1, 18:0, 18:1, 18:2, 18:3, 20:0, 20:1, 20:2, 20:3, 22:0, 22:1 or 22:3. Such biofuel compositions can additionally include at least one additive selected from a cloud point lowering additive that can lower the cloud point to less than about 5° C., or 0° C., a surfactant, or a microemulsion, at least about 5%, 10%, 15%, 20%, 30%, 40%, 50%, 60%, 70% or 80%, 85%, 90%, or 95% diesel fuel from triglycerides, petroleum derived gasoline or diesel fuel from petroleum.

EXAMPLES

FIG. 1 is a diagram of the FAS pathway showing the enzymes directly involved in the synthesis of acyl-ACP. To increase the production of waxes/fatty acid esters, and fatty alcohols one or more of the enzymes can be over expressed or mutated to reduce feedback inhibition. Additionally, enzymes that metabolize the intermediates to make non-fatty acid based products (side reactions) can be functionally deleted or attenuated to increase the flux of carbon through the fatty acid biosynthetic pathway. Examples 1, 2, and 8 below provide exemplary production hosts that have been modified to increase fatty acid production.

Figure 2:
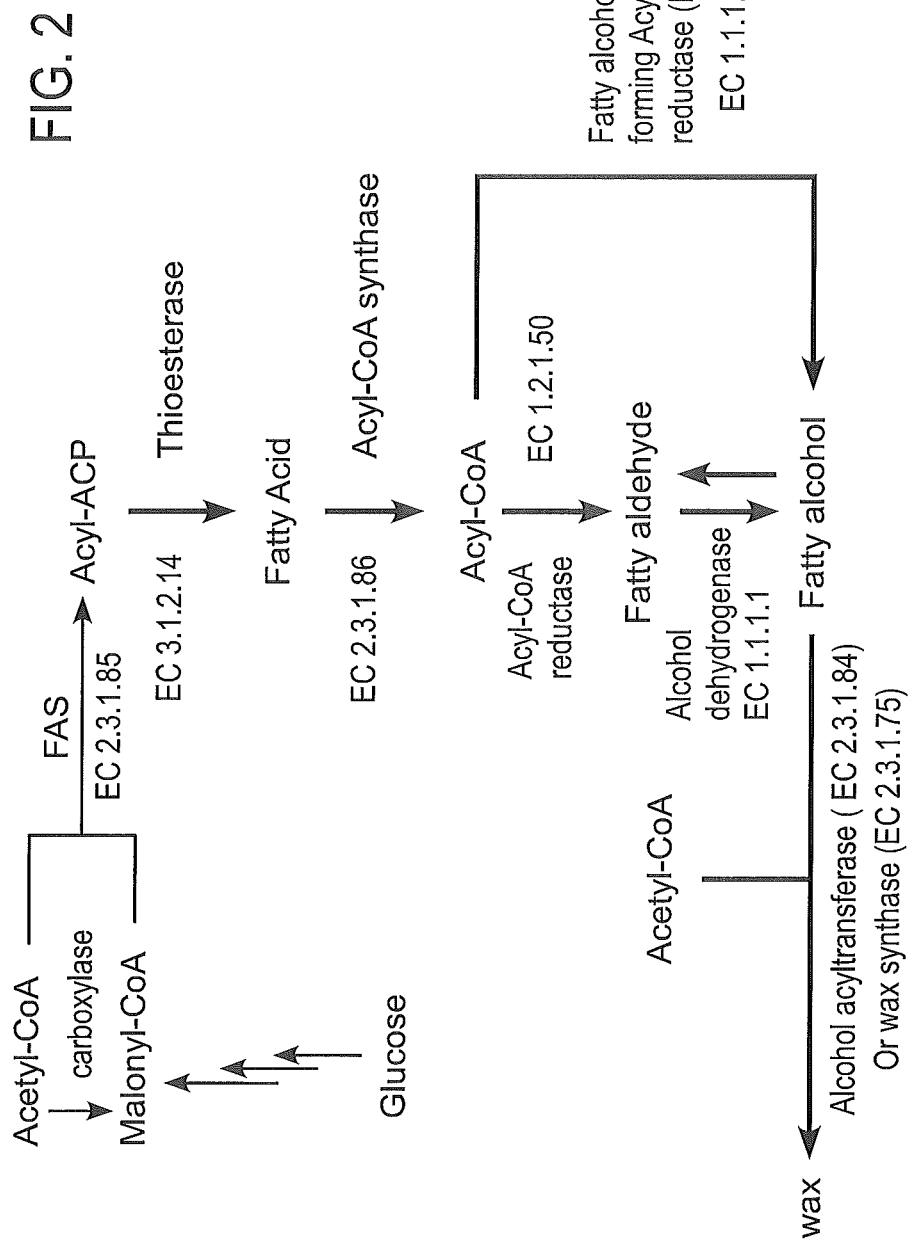
FIG. 2 shows biosynthetic pathways that produce waxes. Waxes can be produced in a host cell using alcohols produced within the host cell or they can be produced by adding exogenous alcohols in the medium. A microorganism designed to produce waxes will produce wax synthase enzymes (EC 2.3.1.75) using exogenous nucleic acid sequences as well as thioesterase (EC 3.1.2.14) sequences. Other enzymes that can be also modulated to increase the production of waxes include enzymes involved in fatty acid synthesis (FAS enzymes EC 2.3.1.85), acyl-CoA synthase (EC 2.3.1.86), fatty alcohol forming acyl-CoA reductase (EC 1.1.1.*), acyl-CoA reductase (1.2.1.50) and alcohol dehydrogenase (EC 1.1.1.1).
Figure 3:
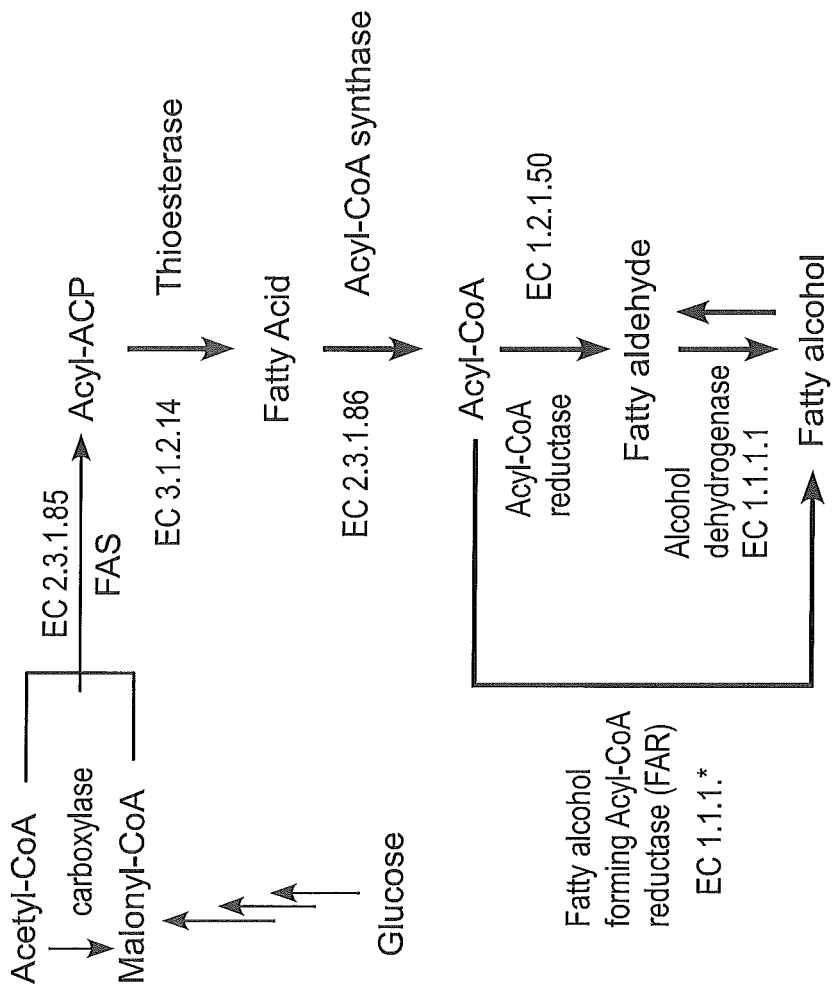
FIG. 3 shows biosynthetic pathways that produce fatty alcohols. Fatty alcohols having defined carbon chain lengths can be produced by expressing exogenous nucleic acid sequences encoding thioesterases (EC 3.1.2.14), and combinations of acyl-CoA reductases (EC 1.2.1.50), alcohol dehydrogenases (EC 1.1.1.1) and fatty alcohol forming acyl-CoA reductases (FAR, EC 1.1.1*). Other enzymes that can be also modulated to increase the production of fatty alcohols include enzymes involved in fatty acid synthesis (FAS enzymes EC 2.3.1.85), and acyl-CoA synthase (EC 2.3.1.86).
Figure 4:
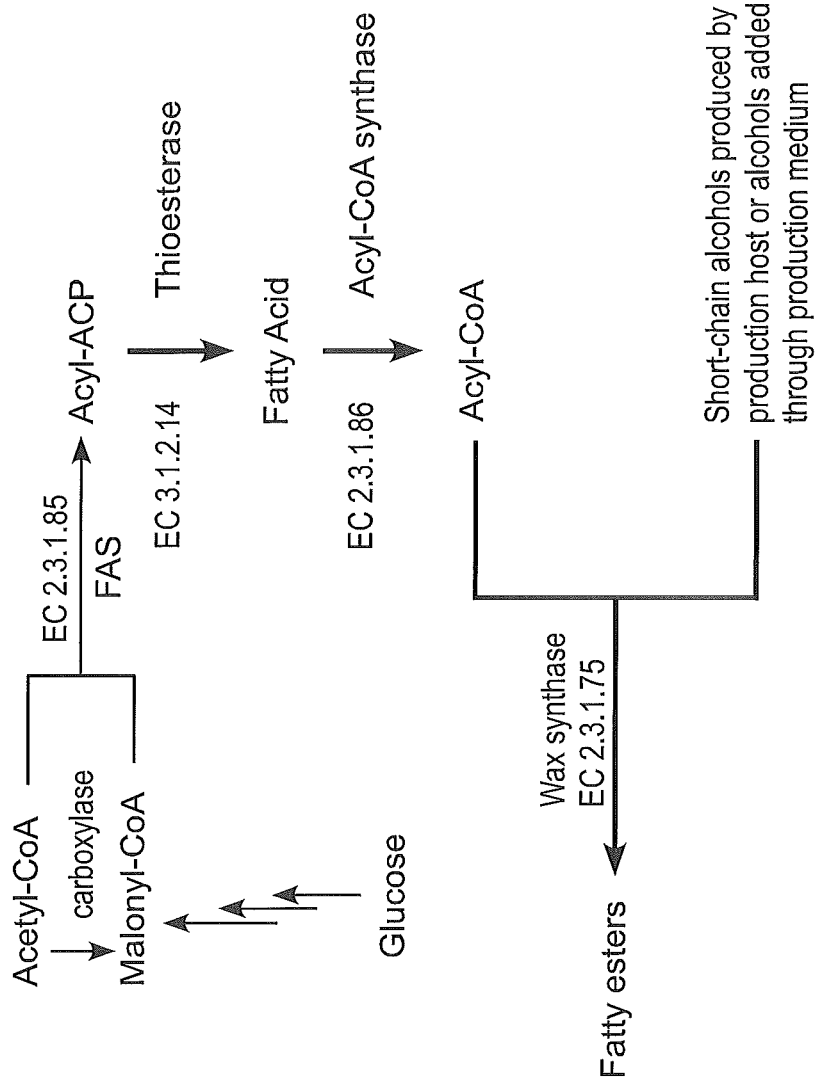
FIG. 4 shows biosynthetic pathways that produce fatty acids esters. Fatty acids esters having defined carbon chain lengths can be produced by exogenously expressing various thioesterases (EC 3.1.2.14), combinations of acyl-CoA reductase (1.23.50), alcohol dehydrogenases (EC 1.1.1.1), and fatty alcohol forming Acyl-CoA reductase (FAR, EC 1.1.1*), as well as, acetyl transferase (EC 2.3.1.84). Other enzymes that can be modulated to increase the production of fatty acid esters include enzymes involved in fatty acid synthesis (FAS enzymes EC 2.3.1.85), and acyl-CoA synthase (EC 2.3.1.86).

FIGS. 2, 3 and 4 show biosynthetic pathways that can be engineered to make fatty alcohols and wax/fatty acid esters, respectively. As illustrated in FIG. 2 the conversion of each substrate (acetyl-CoA, malonyl-CoA, acyl-ACP, fatty acid, and acyl-CoA) to each product (acetyl-CoA, malonyl-CoA, acyl-ACP, fatty acid, and acyl-CoA) can be accomplished using several different polypeptides that are members of the enzyme classes indicated. The Examples below describe microorganisms that have been engineered or can be engineered to produce specific fatty alcohols and waxes/fatty acid esters and hydrocarbons.

Example 1

Production Host Construction

An exemplary production host is LS9001. LS9001 was produced by modifying C41(DE3) from Overexpress.com (Saint Beausine, France) to functionally deleting the fadE gene (acyl-CoA dehydrogenase).

Briefly, the fadE knock-out strain of *E. coli* was made using primers YafV_NotI and Ivry_Ol to amplify about 830 bp upstream of, fadE and primers Lpcaf_ol and LpeaR_Bam to amplify about 960 bp downstream of fadE. Overlap PCR was used to create a construct for in frame deletion of the complete fadE gene. The fadE deletion construct was cloned into the temperature sensitive plasmid pKOV3, which contained a SacB gene for counterselection, and a chromosomal deletion of fadE was made according to the method of Link et al., *J. Bact.* 179:6228-6237, 1997. The resulting strain was not capable of degrading fatty acids and fatty acyl-CoAs (this functional deletion is herein designated as ΔfadE).

Additional modifications that can be included in a production host include introducing a plasmid carrying the four genes which are responsible for acetyl-CoA carboxylase activity in *E. coli* (accA, B, C, and D, Accessions: NP_414727, NP_417721, NP_417722, NP_416819, EC 6.4.1.2). The accABCD genes were cloned in two steps as bicistronic operons into the NcoI/HindIII and NdeI/AwiII sites of pACYCDuet-1 (Novagen, Madison, Wis.) the resulting plasmid was termed pAS004.126.

Additional modifications that can be included in a production host include the following: over-expression of aceEF (encoding the E1p dehydrogase component and the E2p dihydrolipoamide acyltransferase component of the pyruvate and 2-oxoglutarate dehydrogenase complexes); and fabH/fabD/fabG/acpP/fabF (encoding FAS) from any organism known in the art to encode such proteins, including for example *E. coli, Nitrosomonas europaea* (ATCC 19718), *Bacillus subtilis, Saccharomyces cerevisiae, Streptomyces* spp, *Ralstonia, Rhodococcus, Corynebacteria, Brevibacteria, Mycobacteria*, oleaginous yeast, and the like can be expressed in the production host. Similarly, production hosts can be engineered to express accABCD (encoding acetyl co-A carboxylase) from *Pisum savitum* instead of, or in addition to, the *E. coli* homologues. However, when the production host is also producing butanol it is less desirable to express the *Pisum savitum* homologue.

In some exemplary production hosts, genes can be knocked out or attenuated using the method of Link, et al., *J. Bacteriol.* 179:6228-6237, 1997. For example, genes that can be knocked out or attenuated include gpsA (encoding biosynthetic sn-glycerol 3-phosphate dehydrogenase, accession NP_418065, EC: 1.1.1.94); ldhA (encoding lactate dehydrogenase, accession NP_415898, EC: 1.1.1.28); pflb (encoding formate acetyltransferase 1, accessions: P09373, EC: 2.3.1.54); adhE (encoding alcohol dehydrogenase, accessions: CAA47743, EC: 1.1.1.1, 1.2.1.10); pta (encoding phosphotransacetylase, accessions: NP_416800, EC: 2.3.1.8); poxB (encoding pyruvate oxidase, accessions: NP_415392, EC: 1.2.2.2); ackA (encoding acetate kinase, accessions: NP_416799, EC: 2.7.2.1) and combinations thereof.

Similarly, the PlsB[D311E] mutation can be introduced into LS9001 to attenuate PlsB using the method described above for the fadE deletion. Once introduced, this mutation will decrease the amount of carbon being diverted to phospholipid production (see, FIG. 1). Briefly, an allele encoding PlsB[D311E] is made by replacing the GAC codon for aspartate 311 with a GAA codon for glutamate. The altered allele is made by gene synthesis and the chromosomal plsB wildtype allele is exchanged for the mutant plsB[D311E] allele using the method of Link et al. (see above).

Example 2

Production Host Modifications

The following plasmids were constructed for the expression of various proteins that are used in the synthesis of fatty acid derivatives. The constructs were made using standard molecular biology methods and all the cloned genes were put under the control of IPTG-inducible promoters (T7, tac or lac promoters).

The tesA gene (thioesterase A gene accession NP_415027 without leader sequence (Cho and Cronan, *J. Biol. Chem.*, 270:4216-9, 1995, EC: 3.1.1.5, 3.1.2.-) of *E. coli* was cloned into NdeI/AvrII digested pETDuet-1 (pETDuet-1 described herein is available from Novagen, Madison, Wis.). Genes encoding for FatB-type plant thioesterases (TEs) from *Umbellularia california, Cuphea hookeriana* and *Cinnamonum camphortan* (accessions: UcFatB1=AAA34215, ChFatB2=AAC49269, ChFatB3=AAC72881, CcFatB=AAC49151 were individually cloned into three different vectors: (i) NdeI/AvrII digested pETDuet-1, (ii) XhoI/HindIII digested pBluescript KS+(Stratagene, La Jolla, Calif.)(used to create N-terminal lacZ::TE fusion proteins) and (iii) XbaI/HindIII digested pMAL-c2X (New England Lab, Ipswich, Mass.) (used to create n-terminal MalE::TE fusions). The fadD gene (encoding acyl-CoA synthetase) from *E. coli* was cloned into a NcoI/HindIII digested pCDFDuet-1 derivative, which contained the acr1 gene (acyl-CoA reductase) from *Acinetobacter baylyi* ADP1 within its NdeI/AvrII sites. Table 7 provides a summary of the plasmids generated to make several exemplary production strains, one of ordinary skill in the art will appreciate that different plasmids and genomic modifications can be used to achieve similar strains.

TABLE 7

Summary of Plasmids used in Production hosts

| Plasmid | Source Organism Gene Product | Accession No., EC number |
|---|---|---|
| pETDuet-1-tesA | *E. coli* TesA | Accessions: NP_415027, EC: 3.1.1.5, 3.1.2.— |
| pETDuet-1-TEuc pBluescript-TEuc pMAL-c2X-TEuc | *Umbellularia California* UcFatB1 | Q41635 AAA34215 |
| pETDuet-1-TEch pBluescript-TEch pMAL-c2X-TEch | *Cuphea hookeriana* ChFatB2 ChFatB3 | ABB71581 AAC49269 AAC72881 |
| pETDuet-1-TEcc pBluescript-TEcc TEci | *Cinnamonum camphorum* CcFatB | AAC49151 |
| pCDFDuet-1-fadD-acr1 | *E. coli* | fadD: Accessions NP_416319, EC 6.2.1.3 acr1: Accessions YP_047869 |

The chosen expression plasmids contain compatible replicons and antibiotic resistance markers, so that a four-plasmid expression system can be established. Therefore, LS9001 can be co-transformed with (i) any of the TE-expressing plasmids, (ii) the FadD-expressing plasmid, which also expresses acr1 and (iii) wax synthase expression plasmid. When induced with IPTG, the resulting strain will produce increased concentrations of fatty-alcohols from carbon sources such as glucose. The carbon chain length and degree of saturation of the fatty alcohol produced is dependent on the thioesterase gene that is expressed.

Example 3

Production of Fatty Alcohol in the Recombinant *E. coli* Strain

Fatty alcohols were produced by expressing a thioesterase gene and an acyl-CoA reductase gene (FAR) exogenously in a production host. More specifically, plasmids pCDFDuet-1-fadD-acr1 (acyl-CoA reductase) and pETDuet-1-'tesA (thioesterase) were transformed into *E. coli* strain LS9001 (described in Example 1) and corresponding transformants were selected in LB plate supplemented with 100 mg/L of spectinomycin and 50 mg/L of carbenicillin. Four transformants of LS9001/pCDFDuet-1-fadD-acr1 were independently inoculated into 3 mL of M9 medium supplemented with 50 mg/L of carbenicillin and 100 mg/L of spectinomycin). The samples containing the transformants were grown in at 25° C. in a shaker (250 rpm) until they reached 0.5 $OD_{600}$. 1.5 mL of each sample was transferred into a 250 mL flask containing 30 mL of the medium described above. The resulting culture was grown at 25° C. in a shaker until the culture reached between 0.5-1.0 $OD_{600}$. IPTG was then added to a final concentration of 1 mM, and growth continued for 40 hours.

The cells were then spun down at 4000 rpm and the cell pellets were suspended in 1.0 mL of methanol. 3 mL of ethyl acetate was then mixed with the suspended cells. 3 mL of $H_2O$ were then added to the mixture and the mixture was sonicated for 20 minutes. The resulting sample was centrifuged at 4000 rpm for 5 minutes and the organic phase (the upper phase) which contained fatty alcohol and was subjected to GC/MS analysis. Total alcohol (including tetradecanol, hexadecanol, hexadecenol and octadecenol) yield was about 1-10 mg/L. When an *E. coli* strain carrying only empty vectors was cultured in the same way, only 0.2-0.5 mg/L of fatty alcohols were found in the ethyl acetate extract.

Example 4

Production and Release of Fatty Alcohol from Production Host

Acr1 (acyl-CoA reductase) was expressed in *E. coli* grown on glucose as the sole carbon and energy source. The *E. coli* produced small amounts of fatty alcohols such as dodecanol (C12:0-OH), tetradecanol (C14:0-OH) and hexadecanol (C16:0-OH). In other samples, FadD (acyl-CoA synthetase) was expressed together with acr1 in *E. coli* and a five-fold increase in fatty alcohol production was observed.

Figure 5:
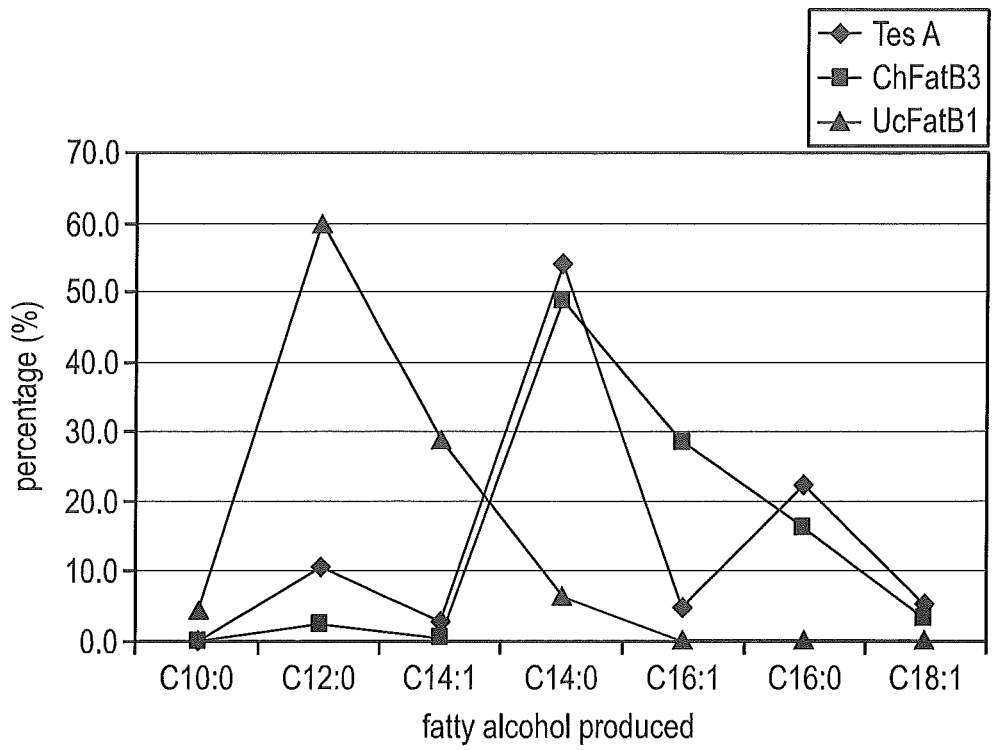
FIG. 5 shows fatty alcohol production by the strain described in Example 4, co-transformed with pCDFDuet-1-fadD-acr1 and plasmids containing various thioesterase genes. The strains were grown aerobically at 25° C. in M9 mineral medium with 0.4% glucose in shake flasks. Saturated C10, C12, C14, C16 and C18 fatty alcohol were identified. Small amounts of C16:1 and C18:1 fatty alcohols were also detected in some samples. Fatty alcohols were extracted from cell pellets using ethyl acetate and derivatized with N-trimethylsilyl (TMS) imidazole to increase detection.

In other samples, acr1, fadD, accABCD (acetyl-CoA Carboxylase) (plasmid carrying accABCD constructed as described in Example 1) were expressed along with various individual thioesterases (TEs) in wildtype *E. coli* C41(DE3) and an *E. coli* C41(DE3) ΔfadE, a strain lacking acyl-CoA dehydrogenase. This resulted in additional increases in fatty alcohol production and modulating the profiles of fatty alcohols (see FIG. 5). For example, over-expression of *E. coli* 'tesA (pETDuet-1-'tesA) in this system achieved approximately a 60-fold increase in C12:0-OH, C14:0-OH and C16:0-OH with C14:0-OH being the major fatty alcohol. A very similar result was obtained when the ChFatB3 enzyme (FatB3 from *Cuphea hookeriana* in pMAL-c2X-TEcu) was expressed. When the UcFatB1 enzyme (FatB1 from *Umbellularia californica*in pMAL-c2X-TEuc) was expressed, fatty alcohol production increased approximately 20-fold and C12:0-OH was the predominant fatty alcohol.

Figure 6:
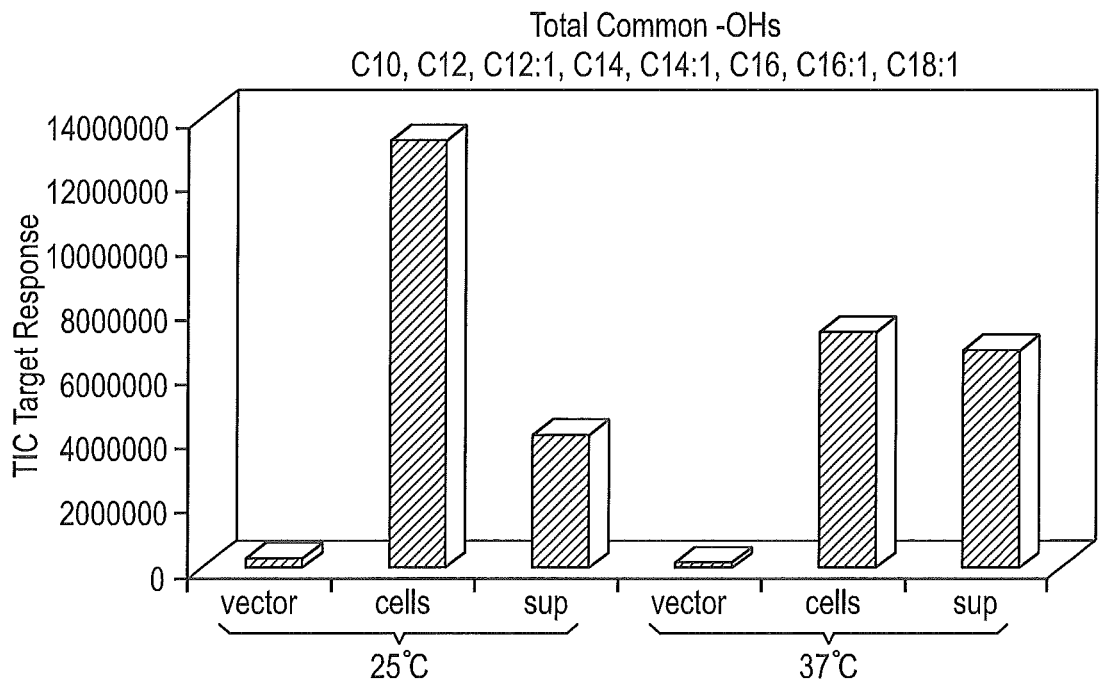
FIG. 6 shows the release of fatty alcohols from the production strain. Approximately 50% of the fatty alcohol produced was released from the cells when they were grown at 37° C.

Expression of ChFatB3 and UcFatB1 also led to the production of significant amounts of the unsaturated fatty alcohols C16:1-OH and C14:1-OH, respectively. The presence of fatty alcohols was also found in the supernatant of samples generated from the expression of tesA (FIG. 6). At 37° C. approximately equal amounts of fatty alcohols were found in the supernatant and in the cell pellet, whereas at 25° C. approximately 25% of the fatty alcohols were found in the supernatant.

Example 5

Medium Chain Fatty Acid Esters

Alcohol acetyl transferases (AATs, EC 2.3.1.84), which is responsible for acyl acetate production in various plants, can be used to produce medium chain length waxes, such as octyl octanoate, decyl octanoate, decyl decanoate, and the like. Fatty esters, synthesized from medium chain alcohol (such as C6, C8) and medium chain acyl-CoA (or fatty acids, such as C6 or C8) have a relative low melting point. For example, hexyl hexanoate has a melting point of −55° C. and octyl octanoate has a melting point of −18 to −17° C. The low melting points of these compounds makes them good candidates for use as biofuels.

In this example, a SAAT gene was co-expressed in a production host C41(DE3, ΔfadE) withfizciD from *E. coli* and acr1 (alcohol reductase from *A. baylyi* ADP1) and octanoic acid was provided in the fermentation broth. This resulted in the production of octyl octanoate. Similarly, when the wax synthase gene from *A. baylyi* ADP1 was expressed in the production host instead of the SAAT gene octyl octanoate was produced.

A recombinant SAAT gene was synthesized using DNA 2.0 (Menlo Park, Calif. 94025). The synthesized DNA was based on the published gene sequence (accession number AF193789) and modified to eliminate the NcoI site. The synthesized SAAT gene (as a BamHI-HindIII fragment) was cloned in pRSET B (Invitrogen, Calsbad, Calif.), linearized with BanHI and HindIII. The resulted plasmid, pHZ1.63A was cotransformed into an *E. coli* production host with pAS004.114B, which carries a fadD gene from *E. coli* and acr1 gene from *A. baylyi* ADP1. The transformants were grown in 3 mL of M9 medium with 2% of glucose. After IPTG induction and the addition of 0.02% of octanoic acid, the culture was continued at 25° C. from 40 hours. After that, 3 mL of acetyl acetate was added to the whole culture and mixed several times with mixer. The acetyl acetate phase was analyzed by GC/MS.

Surprising, in the acetyl acetate extract, there is no acyl acetate found. However, a new compound was found and the compound was octyl octanoate. Whereas the control strain without the SAAT gene [C41(DE3, ΔfadE)/pRSET B+pAS004.11413] did not produce octyl octanoate. Also the strain [C41(DE3, ΔfadE)/pHZ1.43 B+pAS004.11413], in which the wax synthase gene from *A. baylyi* ADP1 was carried by pHZ1.43 produced octyl octanoate (see FIG. 7B).

The finding that SAAT activity produces octyl octanoate has not reported before and makes it possible to produce medium chain waxes such as octyl octanoate, octyl decanoate, which have low melting point and are good candidates to be use for biofuel to replace triglyceride based biodiesel.

Example 6

Production of Wax Ester in *E. coli* Strain LS9001

Wax esters were produced by engineering an *E. coli* production host to express a fatty alcohol forming acyl-CoA reductase, thioesterase, and a wax synthase. Thus, the production host produced both the A and the B side of the ester and the structure of both sides was influenced by the expression of the thioesterase gene.

More specifically, wax synthase from *A. baylyi* ADP1 (termed WSadp1, accessions AA017391, EC: 2.3.175) was amplified with the following primers using genomic DNA from *A. baylyi* ADP1 as the template. The primers were (1) WSadp1_NdeI, 5'-TCATATGCGCCCATTACATCCG-3' and (2) WSadp1_Avr, 5'-TCCTAGGAGGGCTAATT-TAGCCCTTTAGTT-3'. The PCR product was digested with NdeI and AvrII and cloned into pCOALDeut-1 to give pHZ 1.43. The plasmid carrying WSadp1 was then co-transformed into *E. coli* strain LS9001 with both pETDuet-1'tesA and pCDEDuet-1-fadD-acyl and transformants were selected in LB plates supplemented with 50 mg/L of kanamycin, 50 mg/L of carbenicillin and 100 mg/L of spectinomycin. Three transformants were inoculated in 3 mL of LBKCS (LB broth supplement with 50 mg/L of kanamycin, 50 mg/L of carbenicillin, 100 mg/L of spectinomycin and 10 g/L of glucose) and cultured at 37° C. shaker (250 rpm). When the cultures reached 0.5 $OD_{600}$, 1.5 mL of each culture was transferred into 250 mL flasks containing 50 mL of LBKCS and the flasks were grown in a shaker (250 rpm) at 37° C. until the culture reached 0.5-1.0 $OD_{600}$. IPTG was then added to a final concentration of 1 mM. The induced cultures were grown at 37° C. shaker for another 40-48 hours.

The culture was then placed into 50 mL conical tubes and the cells were spun down at 3500×g for 10 minutes. The cell pellet was then mixed with 5 mL of ethyl acetate. The ethyl acetate extract was analyzed with GC/MS. The intracellular yield of waxes (including C16C16, C14:1C16, C18:1C18:1, C2C14, C2C16, C2C16:1, C16C16:1 and C2C18:1) was about 10 mg/L. When an *E. coli* strain only carrying empty vectors was cultured in the same way, only 0.2 mg/L of wax was found in the ethyl acetate extract.

Example 7

Production and Release of Fatty-Ethyl Ester from Production Host

Figure 8:
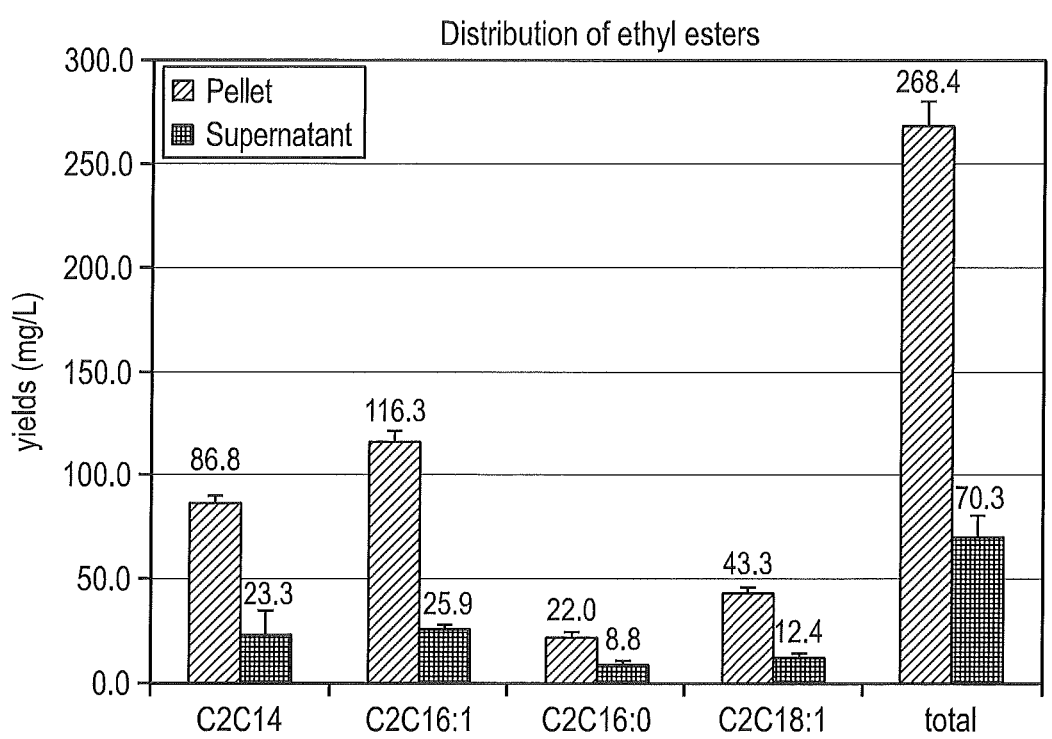
FIG. 8 shows the distribution of ethyl esters made when the wax synthase from *A. baylyi* ADP1 (WSadp1) was co-expressed with thioesterase gene from *Cuphea hookeriana* in a production host.

The LS9001 strain was modified by transforming it with the plasmids carrying a wax synthase gene from *A. baylyi* (plasmid pHZ1.43), a thioesterase gene from *Cuphea hookeriana* (plasmid pMAL-c2X-TEcu) and a fadD gene from *E. coli* (plasmid pCDFDuet-1-fadD). This recombinant strain was grown at 25° C. in 3 mL of M9 medium with 50 mg/L of kanamycin, 100 mg/L of carbenicillin and 100 mg/L of spectinomycin. After IPTG induction, the media was adjusted to a final concentration of 1% ethanol and 2% glucose. The culture was allowed to grow for 40 hours after IPTG induction. The cells were separated from the spent medium by centrifugation at 3500×g for 10 minutes). The cell pellet was re-suspended with 3 mL of M9 medium. The cell suspension and the spent medium were then extracted with 1 volume of ethyl acetate. The resulting ethyl acetate phases from the cells suspension and the supernatant were subjected to GC-MS analysis. The results showed that the C16 ethyl ester was the most prominent ester species (as expected for this thioesterase, see Table 1), and that 20% of the fatty acid ester produced was released from the cell (see FIG. 8). A control *E. coli* strain C41(DE3, ΔfadE) containing pCOLADuet-1 (empty vector for the wax synthase gene), pMAL-c2X-TEuc (containing fatB from *U. california*) and pCDFDuet-1-fadD (fadD gene from *E. coli*) failed to produce detectable amounts of fatty ethyl esters. The fatty acid esters were quantified using commercial palmitic acid ethyl ester as the reference. Fatty acid esters were also made using the methods described herein except that methanol, or isopropanol was added to the fermentation broth and the expected fatty acid esters were produced.

Example 8

The Influence of Various Thioesterases on the Composition of Fatty-Ethyl Esters Produced in Recombinant *E. coli* Strains The thioesterases FatB3 (*C. hookeriana*), TesA (*E. coli*), and FatB (*U. california*) were expressed simultaneously with wax synthase (*A. baylyi*). A plasmid termed pHZ1.61 was constructed by replacing the NotI-AvrII fragment (carrying the acr1 gene) with the NotI-AvrII fragment from pHZ1.43 so that fadD and the ADP1 wax synthase were in one plasmid and both coding sequences were under the control of separate T7 promoter. The construction of pHZ1.61 made it possible to use a two plasmid system instead of the three plasmid system as described in Example 6. pHZ1.61 was then co-transformed into *E. coli* C41(DE3, ΔfadE) with one of the various plasmids carrying the different thioesterase genes stated above.

The total fatty acid ethyl esters (supernatant and intracellular fatty acid ethyl esters) produced by these transformants were evaluated using the technique described herein. The yields and the composition of fatty acid ethyl esters are summarized in Table 8.

TABLE 8

The yields (mg/L) and the composition of fatty acid ethyl esters by recombinant
*E. coli* C41(DE3, ΔfadE)/pHZ1.61 and plasmids carrying various thioesterase genes.

| Thioesterases | C2C10 | C2C12:1 | C2C12 | C2C14:1 | C2C14 | C2C16:1 | C2C16 |
|---|---|---|---|---|---|---|---|
| 'TesA | 0.0 | 0.0 | 6.5 | 0.0 | 17.5 | 6.9 | 21.6 |
| ChFatB3 | 0.0 | 0.0 | 0.0 | 0.0 | 10.8 | 12.5 | 11.7 |
| ucFatB | 6.4 | 8.5 | 25.3 | 14.7 | 0.0 | 4.5 | 3.7 |
| pMAL | 0.0 | 0.0 | 0.0 | 0.0 | 5.6 | 0.0 | 12.8 |

Note:
'TesA, pETDuet-1-'tesA; chFatB3, pMAL-c2X-TEcu; ucFatB, pMAL-c2X-TEuc; pMAL, pMAL-c2X, the empty vector for thioesterase genes used in the study.

Example 9

Production Host Construction

The genes that control fatty acid production are conserved between microorganisms. For example, Table 9 identifies the homologues of many of the genes described herein which are known to be expressed in microorganisms that produce hydrocarbons. To increase fatty acid production and, therefore, hydrocarbon production in microorganisms such as those identified in Table 9, heterologous genes, such as those from *E. coli* can be expressed. One of ordinary skill in the art will also appreciate that genes that are endogenous to the micoorganisms provided in Table 9 can also be over-expressed, or attenuated using the methods described herein. Moreover, genes that are described in FIG. 10 can be expressed or attenuated in microorganisms that endogenously produce hydrocarbons to allow for the production of specific hydrocarbons with defined carbon chain length, saturation points, and branch points.

For example, exogenous nucleic acid sequences encoding acetyl-CoA carboxylase are introduced into *K. radiotolerans*. The following genes comprise the acetyl-CoA carboxylase protein product in *K. radiololerans*; acetyl CoA carboxylase, alpha subunit (accA/ZP_00618306), acetyl-CoA carboxylase, biotin carboxyl carrier protein (accBl ZP_00618387), acetyl-CoA carboxylase, biotin carboxylase subunit (aceC ZP_00618040), and acetyl-CoA carboxylase, beta (carboxyltranferase) subunit (accDl ZP_00618306). These genes are cloned into a plasmid such that they make a synthetic acetyl-CoA carboxylase operon (accABCD) under the control of a *K. radiotolerans* expression system such as the expression system disclosed in Ruyter et al., *Appl Environ Microbial.* 62:3662-3667, 1996. Transformation of the plasmid into *K. radiotolerans* will enhance fatty acid production. The hydrocarbon producing strain of *K. radiotolerans* can also be engineered to make branched, unsaturated hydrocarbons having specific carbon chain lengths using the methods disclosed herein.

TABLE 9

Hydrocarbon Production Hosts

| Organism | Gene Name | Accession No./Seq ID/Loci | EC No. |
|---|---|---|---|
| *Desulfovibrio desulfuricans* G20 | accA | YP_388034 | 6.4.1.2 |
| *Desulfovibrio desulfuricans* G22 | accC | YP_388573/YP_388033 | 6.3.4.14, 6.4.1.2 |
| *Desulfovibrio desulfuricans* G23 | accD | YP_388034 | 6.4.1.2 |
| *Desulfovibrio desulfuricans* G28 | fabH | YP_388920 | 2.3.1.180 |
| *Desulfovibrio desulfuricans* G29 | fabD | YP_388786 | 2.3.1.39 |
| *Desulfovibrio desulfuricans* G30 | fabG | YP_388921 | 1.1.1.100 |
| *Desulfovibrio desulfuricans* G31 | acpP | YP_388922/YP_389150 | 3.1.26.3, 1.6.5.3, 1.6.99.3 |
| *Desulfovibrio desulfuricans* G32 | fabF | YP_388923 | 2.3.1.179 |
| *Desulfovibrio desulfuricans* G33 | gpsA | YP_389667 | 1.1.1.94 |
| *Desulfovibrio desulfuricans* G34 | ldhA | YP_388173/YP_390177 | 1.1.1.27, 1.1.1.28 |
| *Erwinia (micrococcus) amylovora* | accA | 942060-943016 | 6.4.1.2 |
| *Erwinia (micrococcus) amylovora* | accB | 3440869-3441336 | 6.4.1.2 |
| *Erwinia (micrococcus) amylovora* | accC | 3441351-3442697 | 6.3.4.14, 6.4.1.2 |
| *Erwinia (micrococcus) amylovora* | accD | 2517571-2516696 | 6.4.1.2 |
| *Erwinia (micrococcus) amylovora* | fadE | 1003232-1000791 | 1.3.99.— |
| *Erwinia (micrococcus) amylovora* | plsB(D311E) | 333843-331423 | 2.3.1.15 |

TABLE 9-continued

Hydrocarbon Production Hosts

| Organism | Gene Name | Accession No./Seq ID/Loci | EC No. |
|---|---|---|---|
| *Erwinia (micrococcus) amylovora* | aceE | 840558-843218 | 1.2.4.1 |
| *Erwinia (micrococcus) amylovora* | aceF | 843248-844828 | 2.3.1.12 |
| *Erwinia (micrococcus) amylovora* | fabH | 1579839-1580789 | 2.3.1.180 |
| *Erwinia (micrococcus) amylovora* | fabD | 1580826-1581749 | 2.3.1.39 |
| *Erwinia (micrococcus) amylovora* | fabG | CAA74944 | 1.1.1.100 |
| *Erwinia (micrococcus) amylovora* | acpP | 1582658-1582891 | 3.1.26.3, 1.6.5.3, 1.6.99.3 |
| *Erwinia (micrococcus) amylovora* | fabF | 1582983-1584221 | 2.3.1.179 |
| *Erwinia (micrococcus) amylovora* | gpsA | 124800-125810 | 1.1.1.94 |
| *Erwinia (micrococcus) amylovora* | ldhA | 1956806-1957789 | 1.1.1.27, 1.1.1.28 |
| *Kineococcus radiotolerans* SRS30216 | accA | ZP_00618306 | 6.4.1.2 |
| *Kineococcus radiotolerans* SRS30216 | accB | ZP_00618387 | 6.4.1.2 |
| *Kineococcus radiotolerans* SRS30216 | accC | ZP_00618040/ ZP_00618387 | 6.3.4.14, 6.4.1.2 |
| *Kineococcus radiotolerans* SRS30216 | accD | ZP_00618306 | 6.4.1.2 |
| *Kineococcus radiotolerans* SRS30216 | fadE | ZP_00617773 | 1.3.99.— |
| *Kineococcus radiotolerans* SRS30216 | plsB(D311E) | ZP_00617279 | 2.3.1.15 |
| *Kineococcus radiotolerans* SRS30216 | aceE | ZP_00617600 | 1.2.4.1 |
| *Kineococcus radiotolerans* SRS30216 | aceF | ZP_00619307 | 2.3.1.12 |
| *Kineococcus radiotolerans* SRS30216 | fabH | ZP_00618003 | 2.3.1.180 |
| *Kineococcus radiotolerans* SRS30216 | fabD | ZP_00617602 | 2.3.1.39 |
| *Kineococcus radiotolerans* SRS30216 | fabG | ZP_00615651 | 1.1.1.100 |
| *Kineococcus radiotolerans* SRS30216 | acpP | ZP_00617604 | 3.1.26.3, 1.6.5.3, 1.6.99.3 |
| *Kineococcus radiotolerans* SRS30216 | fabF | ZP_00617605 | 2.3.1.179 |
| *Kineococcus radiotolerans* SRS30216 | gpsA | ZP_00618825 | 1.1.1.94 |
| *Kineococcus radiotolerans* SRS30216 | ldhA | ZP_00618879 | 1.1.1.27, 1.1.1.28 |
| *Rhodospirillum rubrum* | accA | YP_425310 | 6.4.1.2 |
| *Rhodospirillum rubrum* | accB | YP_427521 | 6.4.1.2 |
| *Rhodospirillum rubrum* | accC | YP_427522/YP_425144/ YP_427028/ YP_426209/YP_427404 | 6.3.4.14, 6.4.1.2 |
| *Rhodospirillum rubrum* | accD | YP_428511 | 6.4.1.2 |
| *Rhodospirillum rubrum* | fadE | YP_427035 | 1.3.99.— |
| *Rhodospirillum rubrum* | aceE | YP_427492 | 1.2.4.1 |
| *Rhodospirillum rubrum* | aceF | YP_426966 | 2.3.1.12 |
| *Rhodospirillum rubrum* | fabH | YP_426754 | 2.3.1.180 |
| *Rhodospirillum rubrum* | fabD | YP_425507 | 2.3.1.39 |
| *Rhodospirillum rubrum* | fabG | YP_425508/YP_425365 | 1.1.1.100 |
| *Rhodospirillum rubrum* | acpP | YP_425509 | 3.1.26.3, 1.6.5.3, 1.6.99.3 |
| *Rhodospirillum rubrum* | fabF | YP_425510/YP_425510/ YP_425285 | 2.3.1.179 |
| *Rhodospirillum rubrum* | gpsA | YP_428652 | 1.1.1.94 |
| *Rhodospirillum rubrum* | ldhA | YP_426902/YP_428871 | 1.1.1.27, 1.1.1.28 |
| *Vibrio furnissii* | accA | 1, 16 | 6.4.1.2 |
| *Vibrio furnissii* | accB | 2, 17 | 6.4.1.2 |
| *Vibrio furnissii* | accC | 3, 18 | 6.3.4.14, 6.4.1.2 |
| *Vibrio furnissii* | accD | 4, 19 | 6.4.1.2 |

TABLE 9-continued

Hydrocarbon Production Hosts

| Organism | Gene Name | Accession No./Seq ID/Loci | EC No. |
|---|---|---|---|
| *Vibrio furnissii* | fadE | 5, 20 | 1.3.99.— |
| *Vibrio furnissii* | plsB(D311E) | 6, 21 | 2.3.1.15 |
| *Vibrio furnissii* | aceE | 7, 22 | 1.2.4.1 |
| *Vibrio furnissii* | aceF | 8, 23 | 2.3.1.12 |
| *Vibrio furnissii* | fabH | 9, 24 | 2.3.1.180 |
| *Vibrio furnissii* | fabD | 10, 25 | 2.3.1.39 |
| *Vibrio furnissii* | fabG | 11, 26 | 1.1.1.100 |
| *Vibrio furnissii* | acpP | 12, 27 | 3.1.26.3, 1.6.5.3, 1.6.99.3 |
| *Vibrio furnissii* | fabF | 13, 28 | 2.3.1.179 |
| *Vibrio furnissii* | gpsA | 14, 29 | 1.1.1.94 |
| *Vibrio furnissii* | ldhA | 15, 30 | 1.1.1.27, 1.1.1.28 |
| *Stenotrophomonas maltophilia* R551-3 | accA | ZP_01643799 | 6.4.1.2 |
| *Stenotrophomonas maltophilia* R551-3 | accB | ZP_01644036 | 6.4.1.2 |
| *Stenotrophomonas maltophilia* R551-3 | accC | ZP_01644037 | 6.3.4.14, 6.4.1.2 |
| *Stenotrophomonas maltophilia* R551-3 | accD | ZP_01644801 | 6.4.1.2 |
| *Stenotrophomonas maltophilia* R551-3 | fadE | ZP_01645823 | 1.3.99.— |
| *Stenotrophomonas maltophilia* R551-3 | plsB(D311E) | ZP_01644152 | 2.3.1.15 |
| *Stenotrophomonas maltophilia* R551-3 | aceE | ZP_01644724 | 1.2.4.1 |
| *Stenotrophomonas maltophilia* R551-3 | aceF | ZP_01645795 | 2.3.1.12 |
| *Stenotrophomonas maltophilia* R551-3 | fabH | ZP_01643247 | 2.3.1.180 |
| *Stenotrophomonas maltophilia* R551-3 | fabD | ZP_01643535 | 2.3.1.39 |
| *Stenotrophomonas maltophilia* R551-3 | fabG | ZP_01643062 | 1.1.1.100 |
| *Stenotrophomonas maltophilia* R551-3 | acpP | ZP_01643063 | 3.1.26.3, 1.6.5.3, 1.6.99.3 |
| *Stenotrophomonas maltophilia* R551-3 | fabF | ZP_01643064 | 2.3.1.179 |
| *Stenotrophomonas maltophilia* R551-3 | gpsA | ZP_01643216 | 1.1.1.94 |
| *Stenotrophomonas maltophilia* R551-3 | ldhA | ZP_01645395 | 1.1.1.27, 1.1.1.28 |

For Table 9, Accession Numbers are from GenBank, Release 159.0 as of Apr. 15, 2007, EC Numbers are from KEGG, Release 42.0 as of April 2007 (plus daily updates up to and including May 9, 2007), results for *Erwinia amylovora* strain Ea273 are taken from the Sanger sequencing center, completed shotgun sequence as of May 9, 2007, positions for *Erwinia* represent locations on the Sanger psuedo-chromosome, sequences from *Vibrio furnissii* M1 are from the LS9 VFM1 pseudochromosome, v2 build, as of Sep. 28, 2006, and include the entire gene, and may also include flanking sequence.

Example 10

Additional Exemplary Production Strains

Table 10, below provides additional exemplary production strains. Two example biosynthetic pathways are described for producing fatty acids, fatty alcohols, and wax esters. A genetically engineered host can be produced by cloning the expression of the accABCD genes from *E. coli*, the lesA gene from *E. coli*, and fadD gene from *E. coli* into a host cell. Host cells can be selected from *E. coli*, yeast, add to the list. These genes can also be transformed into a host cell that is modified to contain one or more of the genetic manipulations described in Examples 1 and 2, above.

Example 11

Fermentation

Host microorganisms can be also engineered to express umuC and umuD from *E. coli* in pBAD24 under the pipB-CDE promoter system through de novo synthesis of this gene with the appropriate end-product production genes. For small scale hydrocarbon product production, *E. coli* BL21 (DE3) cells harbouring pRAD24 (with ampicillin resistance and the end-product synthesis pathway) as well as pUMVC1 (with kanamycin resistance and the acetyl CoA/malonyl CoA over-expression system) are incubated overnight at at 37° C. shaken at >200 rpm 2 L flasks in 500 ml LB medium supplemented with 75 mg/mL ampicillin and 50 μg/ml kanamycin until cultures reached an $OD_{600}$ of >0.8. Upon achieving an $OD_{600}$ of >0.8, cells are supplemented with 25 mM sodium proprionate (pH 8.0) to activate the engineered gene systems for production as well as to stop cellular proliferation (through activation of umuC and umuD proteins). Induction is performed for 6 hours at 30° C. After incubation, media is examined for product using GC-MS (as described below).

For large scale product production, the engineered microorganisms are grown in 10 L, 100 L or larger batches, fermented and induced to express desired products based on the specific genes encoded in plasmids as appropriate. E. coli BL21(DE3) cells harbouring pBAD24 (with ampicillin resistance and the end-product synthesis pathway) as well as pUMVC1 (with kanamycin resistance and the acetyl-CoA/malonyl-CoA over-expression system) are incubated from a 500 mL seed culture for 10 L fermentations (5 L for 100 L fermentations) in LB media (glycerol free) at 37° C. shaken at >200 rpm until cultures reached an $OD_{600}$ of >0.8 (typically 16 hours) incubated with 50 □ g/mL kanamycin and 75 µg/mL ampicillin. Media is treated with continuously supplemented to maintain a 25 mM sodium proprionate (pH 8.0) to activate the engineered in gene systems for production as well as to stop cellular proliferation (through activation of umuC and umuD proteins). Media is continuously supplemented with glucose to maintain a concentration 90 g/100 mL. After the first hour of induction, aliquots of no more than 10% of the total cell volume are removed each hour and allowed to sit unaggitated so as to allow the hydrocarbon product to rise to the surface and undergo a spontaneous phase separation. The hydrocarbon component is then collected and the aqueous phase returned to the reaction chamber. The reaction chamber is operated continuously. When the OD.sub.600 drops below 0.6, the cells are replaced with a new batch grown from a seed culture.

For wax ester production, subsequent to isolation, the wax esters are washed briefly in 1 M HCl to split the ester bond, and returned to pH 7 with extensive washing with distilled water.

Example 12

Product Characterization

To characterize and quantify the fatty alcohols and fatty acid esters, gas chromatography (GC) coupled with electron impact mass spectra (MS) detection was used. Fatty alcohol samples were first derivatized with an excess of N-trimethylsilyl (TMS) imidazole to increase detection sensitivity. Fatty acid esters did not required derivatization. Both fatty alcohol-TMS derivatives and fatty acid esters were dissolved in an appropriate volatile solvent, like ethyl acetate. The samples were analyzed on a 30 m DP-5 capillary column using the following method. After a 1 µL splitless injection onto the GC/MS column, the oven is held at 100° C. for 3 minutes. The temperature was ramped up to 320° C. at a rate of 20° C./minute. The oven was held at 320° C. for an additional 5 minutes. The flow rate of the carrier gas helium was 1.3 mL/minute. The MS quadrapole scans from 50 to 550 in/z. Retention times and fragmentation patterns of product peaks were compared with authentic references to confirm peak identity.

Figure 9A:
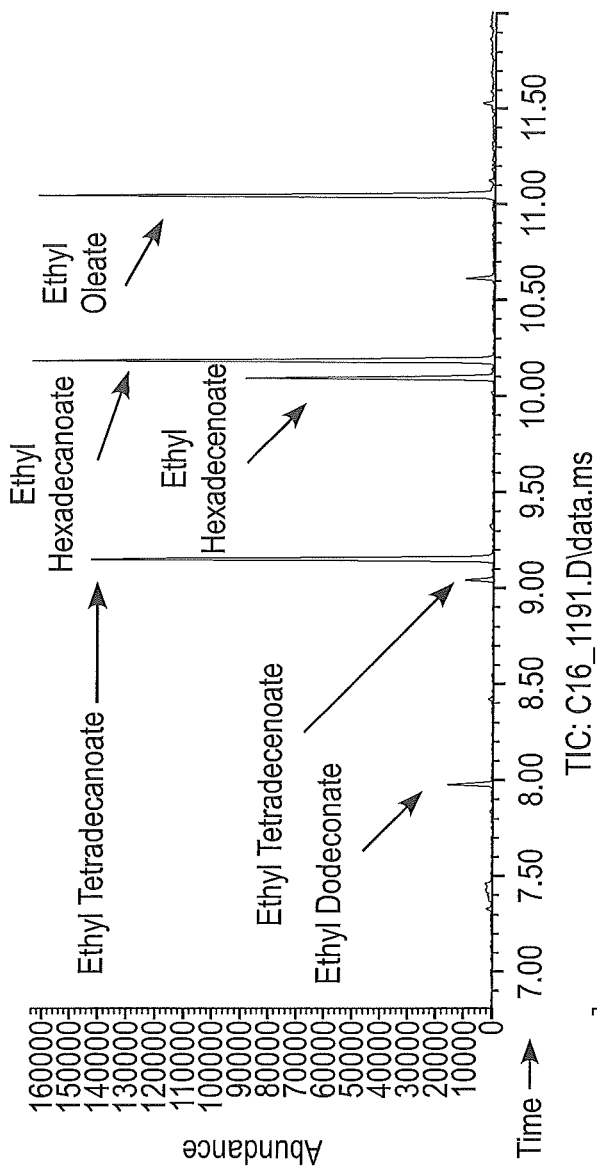
FIGS. 9A and 9B show chromatograms of GC/MS analysis.
Figure 9B:
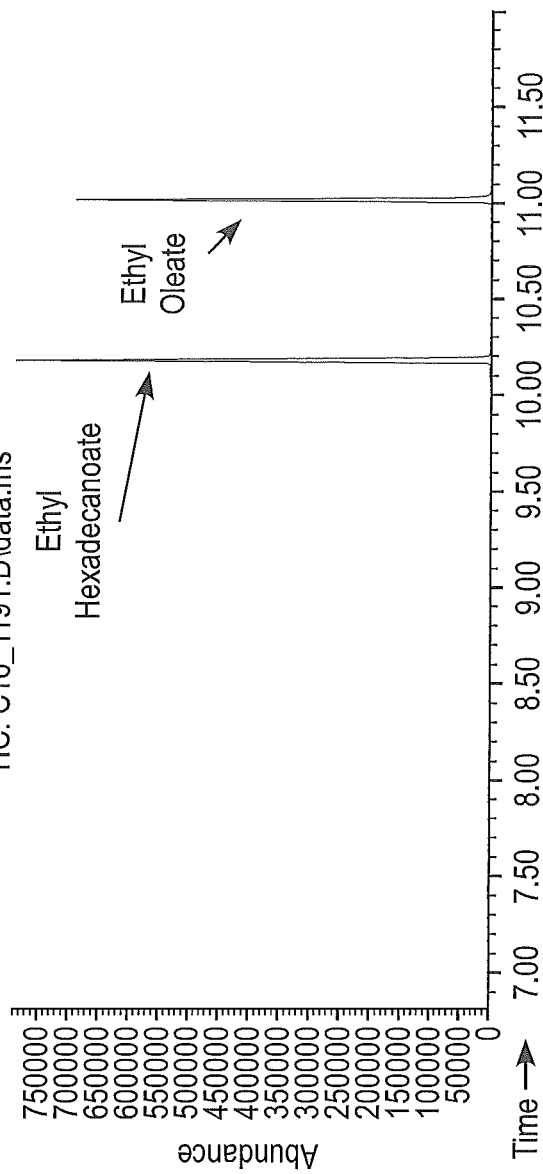

For example, hexadeconic acid ethyl ester eluted at 10.18 minutes (FIGS. 9A and 9B). The parent ion of 284 mass units was readily observed. More abundant were the daughter ions produced during mass fragmentation. This included the most prevalent daughter ion of 80 mass units. The derivatized fatty alcohol hexadecanol-TMS eluted at 10.29 minutes and the parent ion of 313 could be observed. The most prevalent ion was the M-14 ion of 299 mass units.

Quantification was carried out by injecting various concentrations of the appropriate authentic references using the GC/MS method described above. This information was used to generate a standard curve with response (total integrated ion count) versus concentration.

EQUIVALENTS

While specific examples of the subject inventions are explicitly disclosed herein, the above specification and examples herein are illustrative and not restrictive. Many variations of the inventions will become apparent to those skilled in the art upon review of this specification including the examples. The full scope of the inventions should be determined by reference to the examples, along with their full scope of equivalents, and the specification, along with such variations.

What is claimed is:

1. A method of producing a fatty alcohol comprising culturing a genetically engineered *E. coli* comprising exogenous nucleic acids encoding:
   (i) an acetyl-CoA carboxylase (EC 6.4.1.2); and
   (ii) either
   (a) a fatty alcohol forming acyl-CoA reductase (FAR, EC 1.1.1*); or
   (b) an acyl-CoA reductase (EC 1.2.1.50) and an alcohol dehydrogenase (EC 1.1.1.1);
   wherein the *E. coli* is cultured in a medium containing a carbon source under conditions effective to overexpress the exogenous nucleic acids, wherein the genetically engineered *E. coli* produces a fatty alcohol.

2. The method of claim 1, wherein said *E. coli* further comprises an exogenous nucleic acid sequence encoding a thioesterase.

3. The method of claim 1, wherein said *E. coli* comprises an exogenous nucleic acid sequence encoding a fatty alcohol forming acyl-CoA reductase (FAR, EC 1.1.1*).

4. The method of claim 1, wherein the fatty alcohol comprises one or more saturated or unsaturated C12, C14, or C16 fatty alcohols.

5. The method of claim 1, wherein said acyl-CoA reductase (EC 1.2.1.50) is selected from the group consisting of acr1 from *Acinetobacter* baylyi, and jjFAR from *Simmondsia chinensis*.

* * * * *